US010137019B2

(12) United States Patent
Berreklouw

(10) Patent No.: US 10,137,019 B2
(45) Date of Patent: Nov. 27, 2018

(54) MEDICAL INSTRUMENT, RING PROSTHESIS, STENT AND STENTED VALVE

(75) Inventor: Eric Berreklouw, Son (NL)

(73) Assignee: DAIDALOS SOLUTIONS B.V., Son (NL)

( * ) Notice: Subject to any disclaimer, the term of this patent is extended or adjusted under 35 U.S.C. 154(b) by 672 days.

(21) Appl. No.: 14/006,804

(22) PCT Filed: Mar. 23, 2011

(86) PCT No.: PCT/NL2011/050202
§ 371 (c)(1),
(2), (4) Date: Oct. 22, 2013

(87) PCT Pub. No.: WO2012/128613
PCT Pub. Date: Sep. 27, 2012

(65) Prior Publication Data
US 2014/0039599 A1    Feb. 6, 2014

(51) Int. Cl.
*A61F 2/06* (2013.01)
*A61F 2/962* (2013.01)
(Continued)

(52) U.S. Cl.
CPC ............ *A61F 2/962* (2013.01); *A61F 2/2409* (2013.01); *A61F 2/2427* (2013.01); *A61F 2/82* (2013.01);
(Continued)

(58) Field of Classification Search
CPC .................... A61F 2/2409; A61F 2/848; A61F 2220/0008; A61F 2220/0016
(Continued)

(56) References Cited

U.S. PATENT DOCUMENTS 6,485,496 B1 * 11/2002 Suyker ............... A61B 17/0644
227/901
7,972,378 B2 * 7/2011 Tabor ..................... A61F 2/013
623/1.24
(Continued)

FOREIGN PATENT DOCUMENTS

WO         00/24339 A1    5/2000
WO         00/44311 A2    8/2000
(Continued)

OTHER PUBLICATIONS

International Search Report, dated Feb. 9, 2012, corresponds to PCT application.

*Primary Examiner* — Diane Yabut
*Assistant Examiner* — Martin T Ton
(74) *Attorney, Agent, or Firm* — Young & Thompson

(57) ABSTRACT

The medical instrument includes: a first rod; a second rod which extends along the first rod; a longitudinal center line defined by the rods; and a manipulator. The manipulator includes a plurality of fingers, each with a first finger end and a second finger end. The second finger ends are free ends. The first finger ends are supported on the second rod in such a way that the fingers are operable, by moving the second rod in relation to the first rod, in order to be displaced from a first position to a second position. The distance from the free ends of the fingers to the longitudinal center line in the first position is different compared with the second position. A stent, a ring prosthesis and a prosthesis device are also described.

36 Claims, 32 Drawing Sheets

(51) Int. Cl.
*A61F 2/24* (2006.01)
*A61M 39/02* (2006.01)
*A61F 2/82* (2013.01)
*A61F 2/966* (2013.01)

(52) U.S. Cl.
CPC . *A61M 39/0247* (2013.01); *A61F 2002/9665* (2013.01); *A61F 2220/0016* (2013.01)

(58) Field of Classification Search
USPC .................................................. 623/1.11, 1.15
See application file for complete search history.

(56) References Cited

U.S. PATENT DOCUMENTS

| | | | |
|---|---|---|---|
| 8,057,841 B2* | 11/2011 | Reneker | A61F 2/0063 210/503 |
| 8,685,086 B2* | 4/2014 | Navia | A61F 2/2418 623/2.14 |
| 2002/0111620 A1 | 8/2002 | Cooper et al. | |
| 2005/0149160 A1 | 7/2005 | McFerran | |
| 2007/0010877 A1* | 1/2007 | Salahieh | A61F 2/2418 623/2.11 |
| 2008/0208329 A1* | 8/2008 | Bishop | A61B 17/10 623/2.11 |
| 2009/0259305 A1 | 10/2009 | Lane et al. | |
| 2014/0155997 A1* | 6/2014 | Braido | A61F 2/2418 623/2.37 |

FOREIGN PATENT DOCUMENTS

| | | |
|---|---|---|
| WO | 03/003926 A1 | 1/2003 |
| WO | 03/022183 A1 | 3/2003 |
| WO | 03/082121 A2 | 10/2003 |
| WO | 2005/092246 A2 | 10/2005 |
| WO | 2009/045338 A1 | 4/2009 |
| WO | 2009/132187 A1 | 10/2009 |
| WO | 2010/030859 A1 | 3/2010 |
| WO | 2011/025981 A1 | 3/2011 |

* cited by examiner

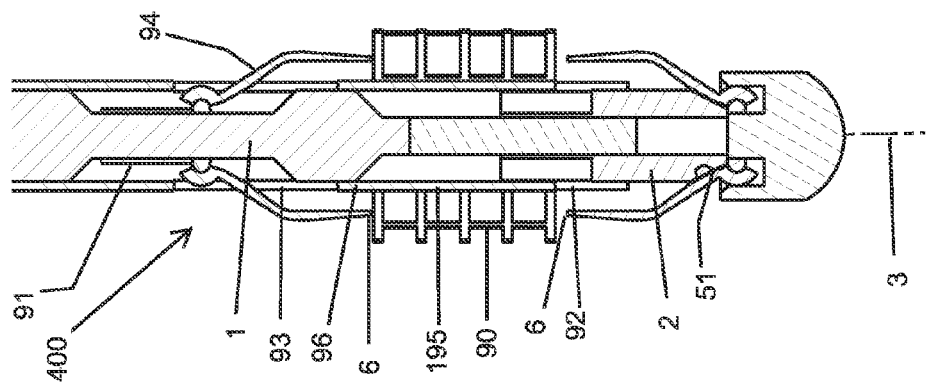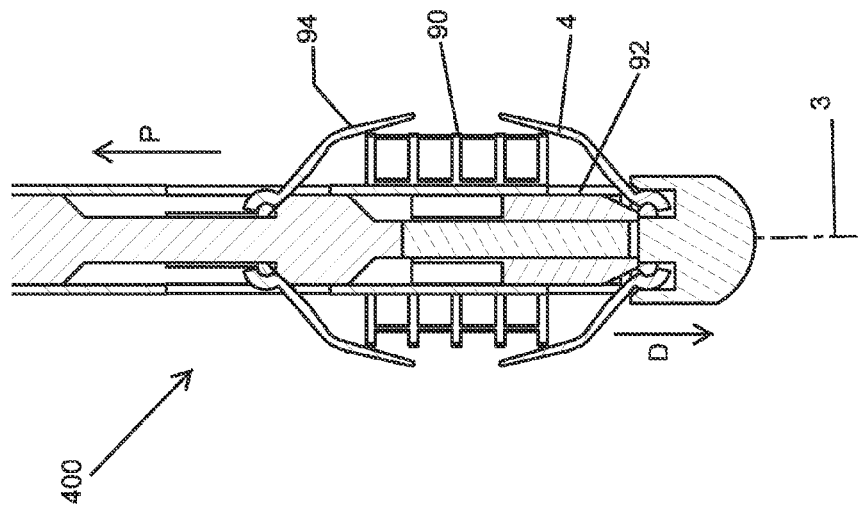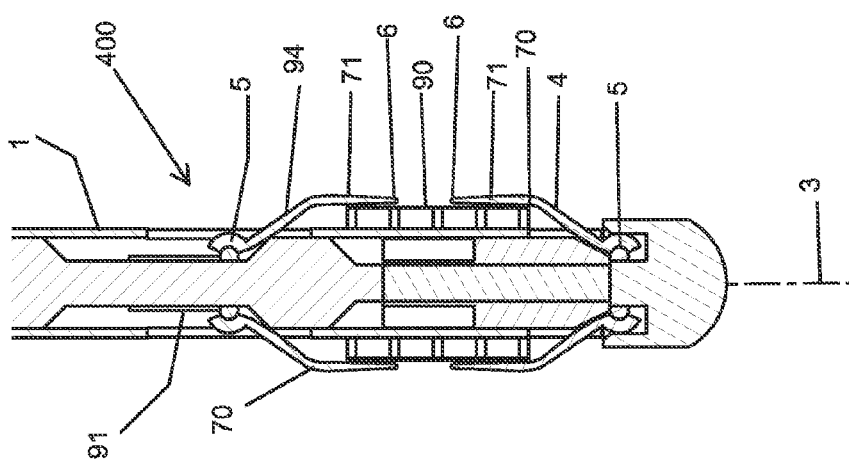

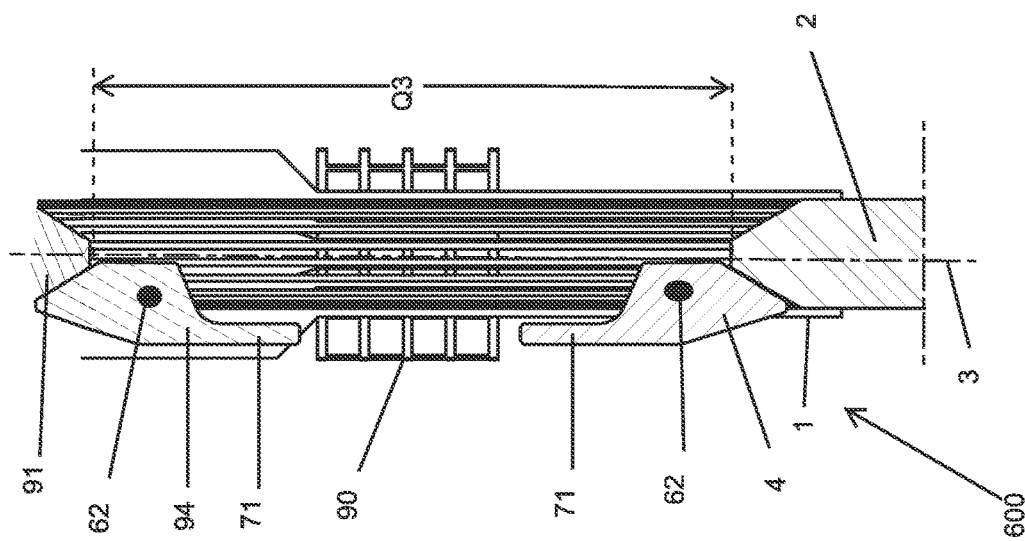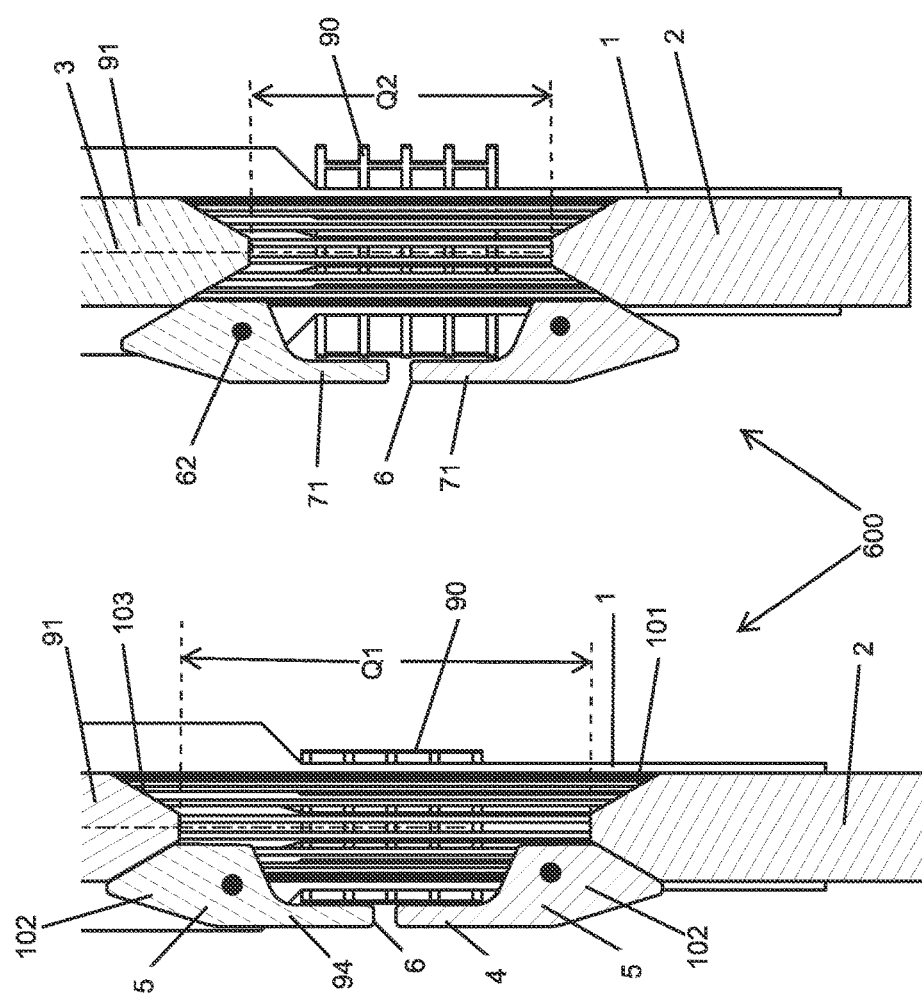

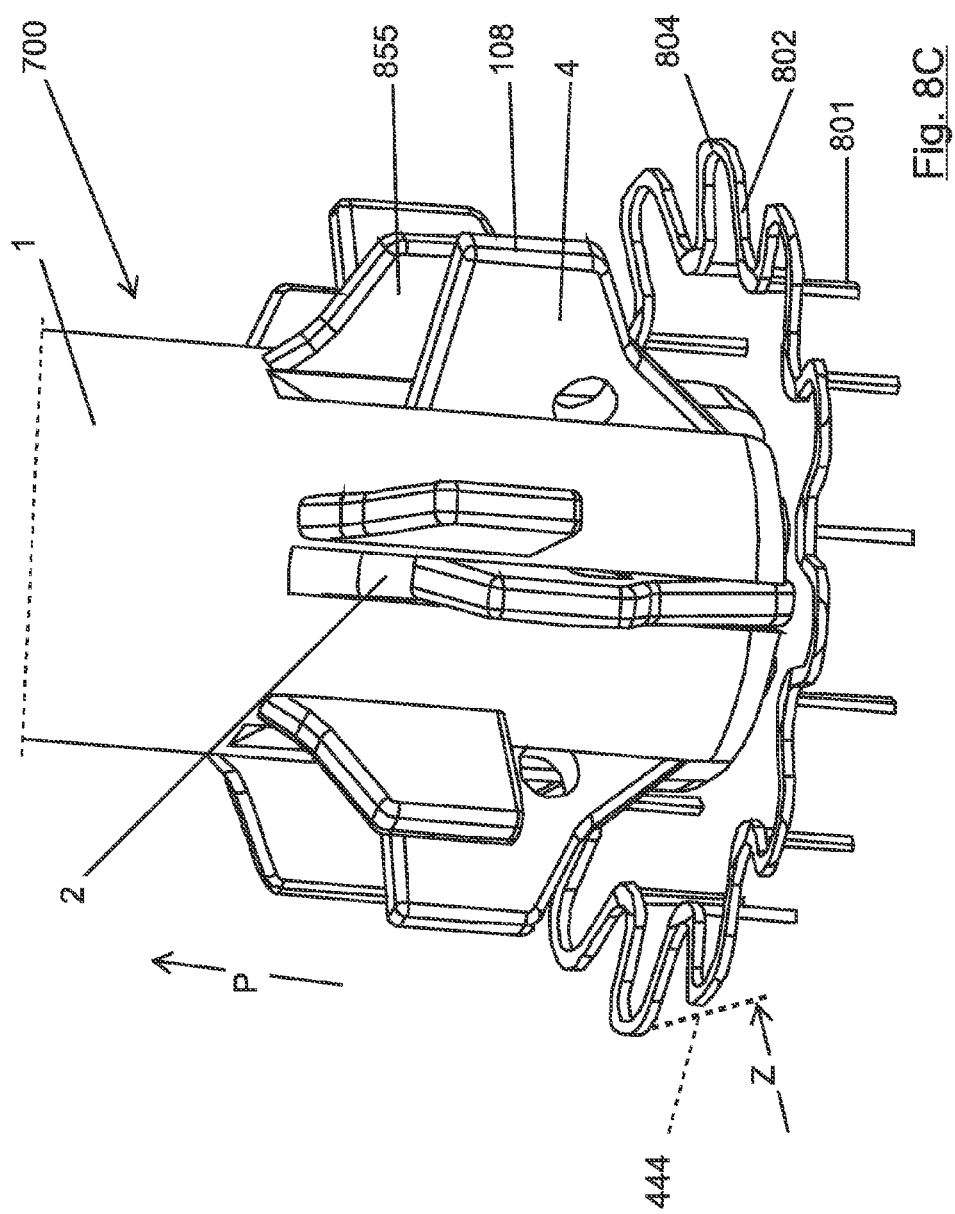

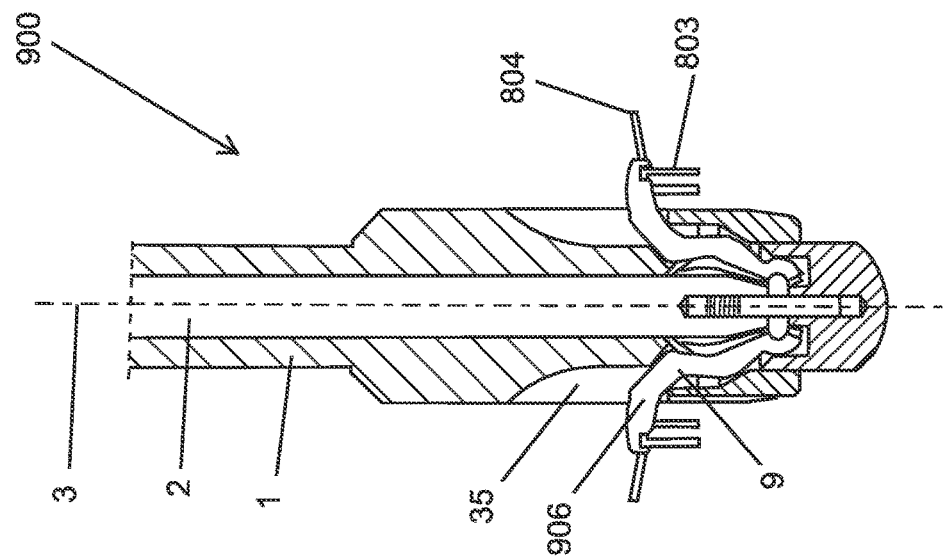
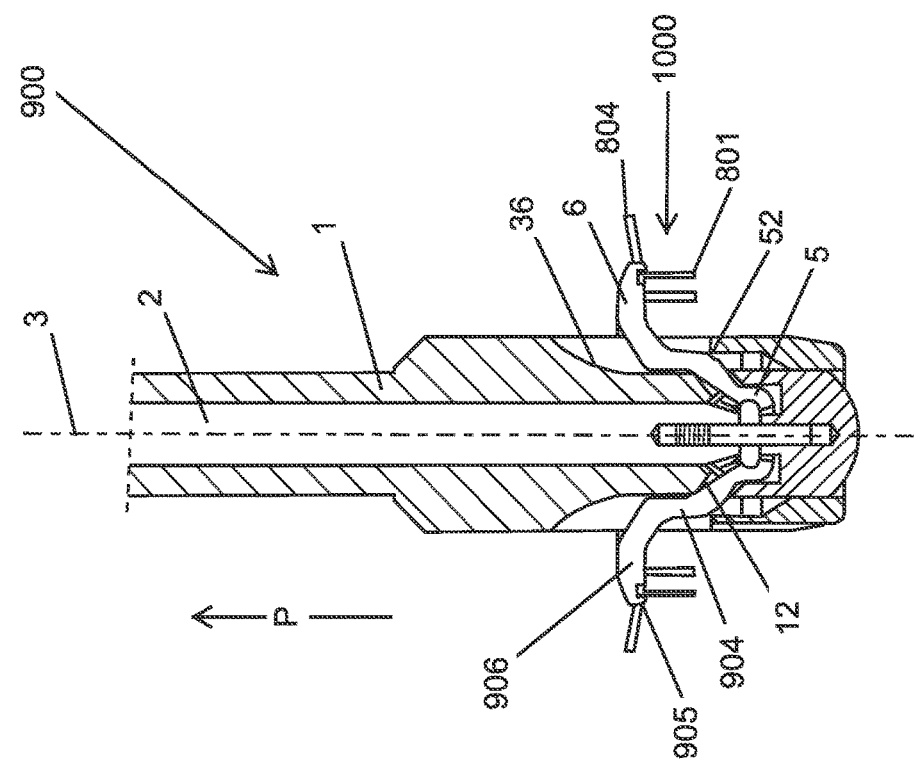

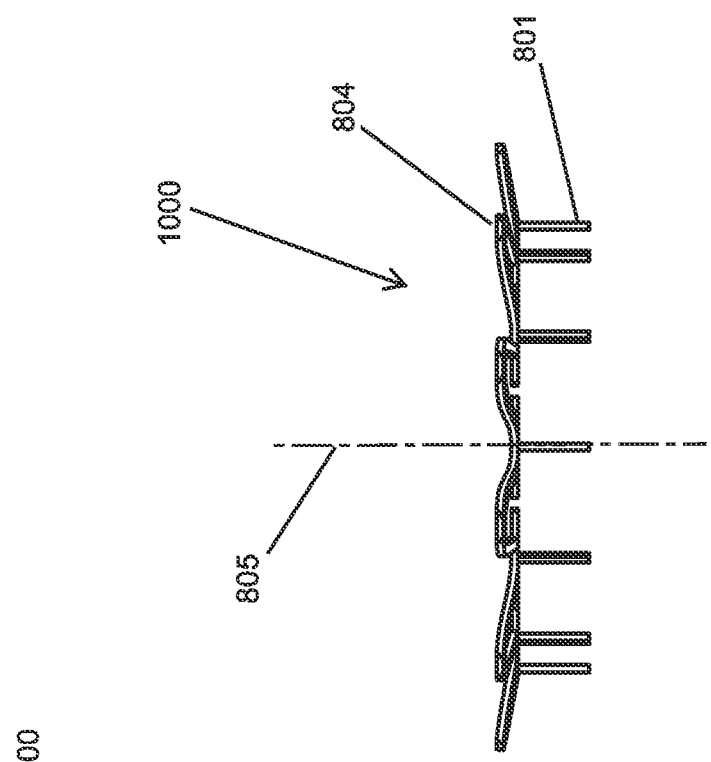
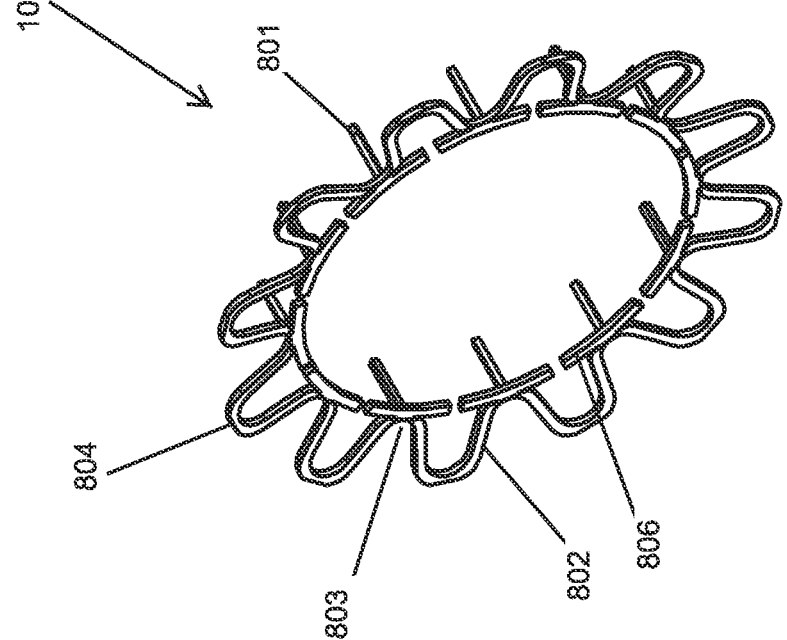
Fig. 11A
Fig. 11B

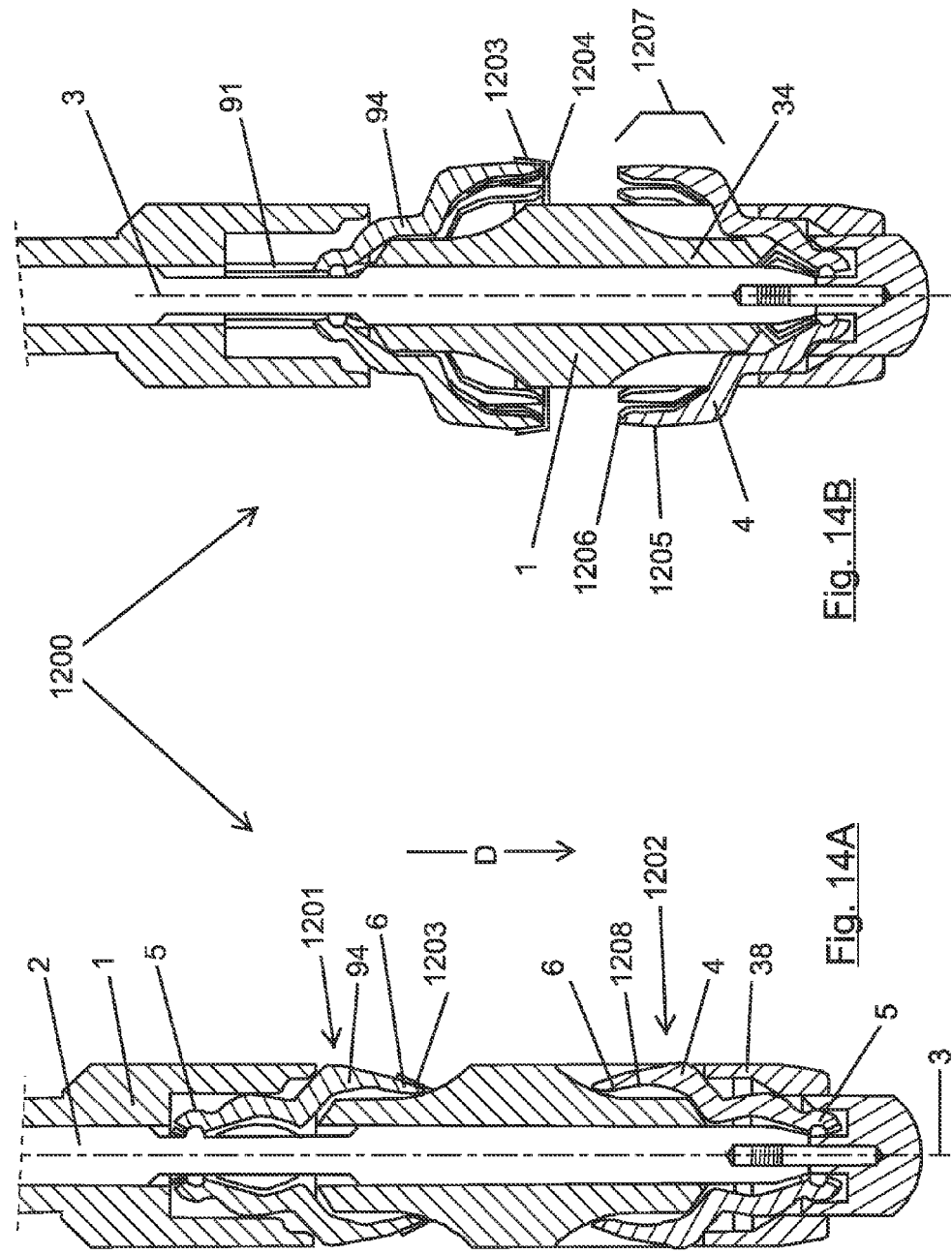

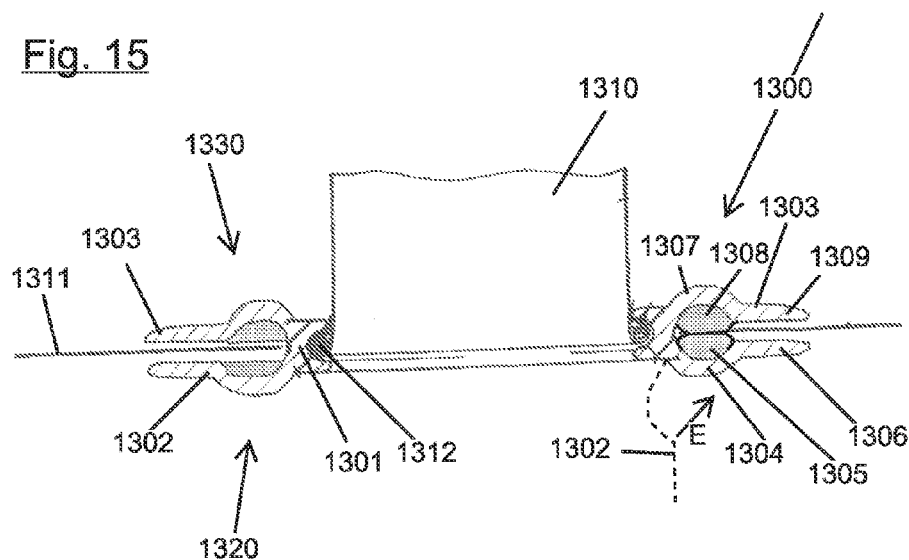
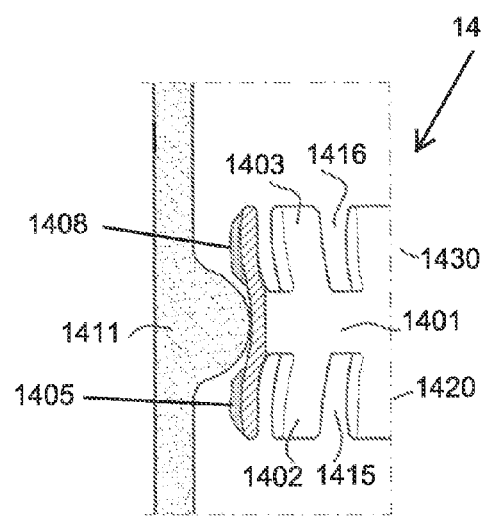
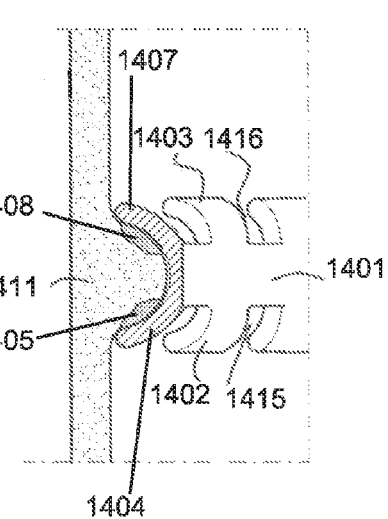

MEDICAL INSTRUMENT, RING PROSTHESIS, STENT AND STENTED VALVE

The present application relates to inventions in the field of prostheses and in the field of medical instruments, such as medical instruments for implanting a prosthesis.

More particularly, this application relates to medical instruments for intervention in, on or near the heart, and/or intervention in or on a passage, such as a blood vessel or hollow organ, through which a body fluid, such as blood, flows. The inventions furthermore also relate to prostheses, such as heart valve prostheses, which are understood in every case to include: so-called ring prostheses, the purpose of which is to constrict an excessively wide passage near a heart valve, or to constrict or close a natural or artificially disposed passage in tissue; artificial valve prostheses, which replace a heart valve; mechanical valve prostheses, but also biological valve prostheses, including so-called stented valves and valved stents; and also components of such prostheses. Furthermore, the inventions also relate to stents and components of the stents. According to the inventions in this application, a prosthesis is also understood to mean a part of a prosthesis.

As far as medical instruments are concerned, the medical instruments according to the present inventions are in particular also usable as an applicator for implanting a 'prosthesis of the type with a tubular element' provided with a distal and proximal flange which extend along the circumference of the tubular element, the distal flange of which has flange feet which are bendable from the extended axial position to the radial position. This type of prosthesis will be further referred to in this application as a 'prosthesis of the type with a tubular element' for short. In the extended axial position, the distal flange feet extend from the tubular element in the distal direction and, in the radial position, the flange feet extend outwards from the tubular element in the radial direction. The extended position is a temporary position here which normally simplifies the movement to the intended location in the body. Having arrived at the intended location, the distal flange feet are bent from the extended axial position to the radial position. Attachment to surrounding tissue is effected here in that tissue on which the distal flange feet and the proximal flange grip is located between the distal flange feet in the radial position and the proximal flange. The grip may be a clamping grip, wherein the tissue is clamped locally between the distal flange feet and proximal flange, or an anchoring grip, wherein the distal flange feet and/or proximal flange are anchored by means of pins or otherwise to the tissue, or a combination of clamping and anchoring grip. In the case of so-called 'prostheses of the type with a tubular element', the bending of the distal flange feet from the extended axial position to the radial position may be both passive bending and active bending, and also a combined form of passive and active bending. In the case of a 'prosthesis of the type with a tubular element', the proximal flange may also optionally comprise flange feet, referred to as proximal flange feet, which are to be bent from an extended axial position to a radial position. This bending of the proximal flange feet can also be both passive bending and active bending, and also a combined form of passive and active bending.

In this application, the term 'passive bending' is understood to mean that a part in a first condition—such as the flange feet in the extended axial position—are under a pre-tension which, once released, bends that part from the first condition to a second condition—such as the flange feet from the extended axial position to the radial position. The bending therefore takes place, as it were, automatically due to the pre-tension. A pre-tension of this type can be implemented in different ways, e.g. by using materials with memory characteristics known to the person skilled in the art. The necessary metals, metal alloys—such as nitinol—or plastics—such as memory polymers—with memory characteristics of this type are known to the person skilled in the art. Materials of this type can be bent from a specific initial configuration—in this case the radial position of the flange feet—to a different configuration—in this case the extended axial position of the flange feet—and can be, as it were, frozen in the different configuration. No mechanical appliances are then required to maintain the frozen different configuration. The, as it were, 'frozen' condition is then releasable, after which the material returns to the initial configuration. In many cases, the change from the initial configuration to the other configuration is effected at a low temperature, for example by laying the material in ice water, as a result of which the material becomes "soft" and can be actively deformed, and the 'freezing' is effected by lowering the initial temperature to below a first threshold value and then to below a second threshold value. This is referred to as an S-shaped temperature-force or temperature-shape curve of the material, wherein the deformation of the material under the influence of the temperature change follows an S-shaped line. The undoing of the frozen condition is normally effected by raising the temperature again to above, in the first instance, the second threshold value, and then again to above the first threshold value, wherein the initial configuration is again attained. In medical applications, the first threshold value often lies a few degrees below the normal body temperature of 37 degrees Celsius, so that the material in each case has the initial configuration at body temperature. The first and second threshold values may lie close to one another, but in practice often lie approximately 10 degrees Celsius apart from one another. In the case of nitinol, the second threshold value is usually lower than or around room temperature. In order then to prevent premature release from the 'frozen condition' under the influence of the room temperature or body temperature of the patient, an additional mechanically removable impediment or a cooling system to maintain a lower temperature will often be involved in practice—and also according to the invention. Finally, it is noted that, according to the invention, a pre-tension of this type is not only implementable by using materials with memory characteristics. A pre-tension of this type can also be created by using a 'normal' resilient material which must be held in a resiliently pre-tensioned condition by means of an external mechanical, removable impediment.

In this application, active bending is understood to mean that an external force must be exerted to bend a part—in this case normally the flange feet—which is, in a manner of speaking, pushed against the part (the flange feet) or pulled onto the part (the flange feet).

So-called 'prostheses of the type with a tubular element', for which the medical instrument according to the invention is usable as an applicator, are, inter alia, described extensively in earlier PCT applications of the inventor, i.e. WO 00/24339, WO 00/44311, WO 03/003926, WO 03/082121 and WO 20051092246. These PCT applications are all included by reference in the present application as far as the details of the 'prosthesis of the type with a tubular element' are concerned.

FIRST ASPECT

According to a first aspect, this application relates to a medical instrument. According to the invention, the medical instrument, according to the first aspect, comprises:

a first rod;

a second rod which extends along and parallel to the first rod;

a longitudinal centre line defined by the direction in which the first rod and the second rod extend; and a manipulator.

The manipulator in the case of the instrument according to the first aspect is usable for manipulating a prosthesis, such as for implanting a prosthesis and/or for creating a passage through tissue and/or for treating a passage intended for through-flow with blood. If the manipulator of the medical instrument according to the first aspect is intended in particular for the implanting of a prosthesis, the medical instrument according to the first aspect is in fact referred to as an applicator. An applicator of this type is known from WO 03/003926 of the inventor.

In the case of the applicator known from WO 03/003926, a release device is involved, comprising a release ring (7) provided on the distal end of the applicator. An overlapping position is involved, in which the distal flange feet of the prosthesis to be implanted project into the release ring in order to be held and/or protected by the release ring in the axial extended position. This release ring can be shifted from the overlapping position in the distal direction by a release rod (6) distally in relation to another rod, referred to as the carriage tube (4), and can thus be moved away from the distal flange feet, after which the distal flange feet lie free and move to the radial position. In WO 03/003926, the manipulator is formed by the aforementioned release ring.

Although in WO 03/003926 the release ring has a diameter which is less than the internal diameter of the prosthesis to be implanted, so that the release ring lying distally from the prosthesis, following implantation of the prosthesis, can be retracted in the proximal direction through the prosthesis, this release ring is relatively large and, when the instrument is retracted following implantation of the prosthesis, can easily remain caught up somewhere. Furthermore, in the case of this release ring, the flange feet pointing radially outwards in the fixed condition must be bent beyond the purely axial position so that they point slightly radially inwards. The reason for this is that the release ring cannot otherwise have a diameter less than the diameter of the passage through the prosthesis. Furthermore, the manipulator from WO 03/003926, i.e. the release ring from WO 03/003926, is passive in the sense that it can only release extended flange feet, but otherwise is hardly or not deployable or usable for other purposes.

According to the first aspect, the object of the present application is, inter alia, to provide an improved medical instrument, comprising: a first rod, a second rod which extends along and parallel to the first rod; a longitudinal centre line defined by the direction in which the first rod and the second rod extend; and a manipulator device.

This object is achieved according to the first aspect by providing a medical instrument, comprising:

a first rod;

a second rod which extends along and parallel to the first rod;

a longitudinal centre line defined by the direction in which the first rod and the second rod extend; and a manipulator;

wherein the manipulator according to the invention comprises at least a plurality of fingers, each with a first finger end and a second finger end; wherein the second finger ends are free ends; wherein the first finger ends of these aforementioned plurality of fingers are supported on the second rod in such a way that the fingers of the aforementioned plurality of fingers, by moving the second rod in relation to the first rod, can be operated in order to be displaced from a first position to a second position; and wherein the distance from the free ends of the fingers to the longitudinal centre line in the first position is different compared with the second position.

Two options are available here according to the first aspect: the distance from the free ends of the fingers can be greater in the first position than in the second position or, conversely, the distance from the free ends of the fingers can be greater in the second position than in the first. It is furthermore noted in a general sense in relation to this application that, viewed from an initial condition in which the distance from the free ends of the fingers to the longitudinal centre line is relatively great, changing to a different condition in which this distance is relatively—in relation to the initial condition—smaller, the change in distance can be referred to by the terms 'reduction in the span of the fingers' or 'span reduction' used in this application. By designing the manipulator as a plurality of fingers with free ends, from which the distance to the longitudinal centre line is variable, it is possible to move the fingers from a first position with, in this example, a great distance to the longitudinal centre line to a second position with, in this example, a small distance to the longitudinal centre line (great distance and small distance are meant here as relative in relation to one another and do not indicate the magnitude of these distances). It is therefore possible, if this medical instrument is used as an applicator, to reduce the manipulator in size after delivering/implanting the prosthesis, thereby making it easier to retract, possibly through the implanted/delivered prosthesis 1. However, it is also possible, in the case of the medical instrument according to the first aspect, to use the manipulator as an attribute for performing an intervention. For example, one or more appliances for an intervention, such as scalpels and/or a punch unit, can be provided on the free finger ends. It is then, for example, possible to move the manipulator, in a reduced-size condition, to the intervention location and there to increase the circumference—or the span—of the manipulator. Scalpels or a punch unit can therefore be moved, while avoiding contact with surrounding tissue, to the intervention location, where they can be increased to the required size in order to be able to treat surrounding tissue. However, the free finger ends may also comprise other appliances for an intervention. The free finger ends can also be simply used without scalpels as pressure units in order, for example, to cause the expansion of a stent or other prosthesis or an original valve, if this, for example, is diseased or constricted. According to the prior art, a balloon is normally used for an expansion of this type. The plurality of fingers according to the first aspect therefore provides an alternative to this.

According to one embodiment of the first aspect, the first rod and the second rod are shiftable in relation to one another in the longitudinal direction of the longitudinal centre line for the aforementioned operation of the fingers. It is therefore possible, by shifting the first rod and the second rod in relation to one another, to subject the fingers to a longitudinal displacement in the direction of the longitudinal centre line of the instrument and/or to a transverse displacement in a direction across the longitudinal centre line of the instrument and/or to a rotation around the longitudinal centre line of the instrument. This may involve:

only a longitudinal displacement; or only a transverse displacement; or only a rotation; or a combination of longitudinal displacement and/or transverse displacement and/or rotation.

A combination of this type may involve a combined displacement, i.e. two or three of the aforementioned types of displacement take place simultaneously, and also a sequential displacement, wherein two or three of the aforementioned types of displacement can take place successively in any required sequence.

According to another further embodiment of the first aspect, the first rod and the second rod are rotatable in relation to one another around the longitudinal centre line for the aforementioned operation of the fingers. The first rod and second rod may be interconnected here according to a further embodiment by means of a screw thread. Rotation of the one rod in relation to the other rod then results in a translation of the one rod in relation to the other rod along the centre line. This translation can then in turn be used to displace the fingers along the longitudinal centre line. Whether or not in combination with a screw thread connection between the first and the second rod, it is also possible, in the case of rotation of the first rod and the second rod in relation to one another around the longitudinal centre line, to displace the fingers along an arc.

According to a further embodiment of the first aspect, in the second position or the first position, the distance from the free ends of the fingers to the second rod is at most 90%, in particular at most 80%, such as at most 75% or at most 70%, of the distance from the free ends of the fingers to the second rod in the other of these two positions. In other words, a span reduction is involved in changing from a great distance to a smaller distance. In parallel with the above, this span reduction of the free ends of the fingers, changing from the first position to the second position (or conversely changing from the second position to the first position), is respectively at least 10%, in particular at least 20%, such as at least 25% or at least 30%. In the case of an expandable prosthesis, a span reduction of up to 90% or possibly 80% will normally be sufficient since the expansion of the prosthesis following delivery thereof already provides the required additional space for the retraction of the manipulator. In situations in which the manipulator is used to expand or support a prosthesis, it is normally useful if the size of this manipulator can increase substantially or even very substantially (speaking in the terminology of span reduction, this is then to be regarded as returning from the widened condition to the original—or even narrower—condition). The same applies even if the manipulator is used as an attribute for performing the intervention.

According to a further embodiment of the first aspect, the plurality of fingers is disposed in a distributed manner over the circumference around the longitudinal centre line.

According to a further embodiment of the first aspect, the free, second finger ends can be provided with a hook with a hook opening which opens in the direction of the first finger ends. The fingers can therefore, for example, project from the proximal side of a prosthesis along the inside of the prosthesis to the distal side of the prosthesis in order to grip from the inside on pins or flange feet of the prosthesis pointing in the distal direction.

According to a further embodiment of the first aspect, the medical instrument comprises a tensioning system which acts on the fingers to pre-tension them for displacement from the first position to the second position. If the fingers are in the first position, the tensioning system under pre-tension then acts on the fingers in one direction—the direction of the pre-tension—in such a way that the tensioning system drives or at least is inclined to drive the fingers from the first position to the second position. The fingers can also be temporarily prevented from moving from the first to the second position, for example if they are first restrained by a physical obstacle (restraining element) which is to be removed. An obstacle of this type could, for example, be a prosthesis or a part of a prosthesis, but may also form part of that part of the medical instrument which is removed once more from (the organ or the body of) the patient following the intervention.

According to a further embodiment of the first aspect, the tensioning system comprises a resilient element provided in the circumferential direction of the instrument along the fingers. A resilient element of this type, such as an elastic resilient element, may, for example, be formed by a ring of an elastic material, such as an elastic plastic. A resilient element may also be designed in other ways. A resilient element may, for example, also have the configuration of an annular spiral spring. A resilient element of this type may be provided on the outside of the fingers, but may also pass through the fingers or be provided on the inside of the fingers.

According to a further embodiment of the first aspect, the distance from the free ends of the fingers to the longitudinal centre line is greater in the first position than in the second position.

According to a further embodiment of the first aspect, the fingers are movable from the first position to the second position and from the second position to a third position, wherein the distance from the free ends of the fingers to the longitudinal centre line in the first position is less than in the second position, and wherein the distance from the free ends of the fingers to the longitudinal centre line in the third position is less than in the second position. It is therefore possible for the fingers to be in an initial position, the first position, when the instrument is brought to the target location in the body of the patient—referred to as the intervention location for short—and, at the 'intervention location', to change from the initial position, i.e. the first position, first to a wider position, i.e. the second position, then to return from the wider position, i.e. the second position, to a narrower position, i.e. the third position, in which the span determined by the fingers is again smaller. The span may possibly be slightly greater in the third position than in the first position. However, this span in the third position will, in particular, be equal to or even less than the span in the initial position, i.e. the first position. This is useful, for example, if the medical instrument is used as an applicator for an expandable prosthesis. In this case, the prosthesis is then brought to the intended location with the fingers in the first position, the prosthesis can then be allowed to expand in a controlled manner at the intended location, i.e. by increasing the span of the fingers in a controlled manner, in order then to return the fingers, after the prosthesis has been detached from the fingers, to a position with a smaller span, the third position. The instrument, in particular the manipulator thereof, can then be easily removed from the patient, possibly even through the expanded prosthesis.

In a further embodiment of the first aspect, the fingers are attached at the first finger ends in a pivotable manner, such as in a hinged manner, via a pivot attachment to the second rod. The free finger ends can therefore pivot around the pivot attachment in order to change the distance from the respective free finger ends to the longitudinal centre line. The transverse dimensions of the manipulator, i.e. the dimensions viewed across the longitudinal centre line of the medical instrument, are largely determined in the part of the medical instrument in the vicinity of the manipulator by precisely this manipulator, and indeed also the (span of the) fingers thereof. By attaching the first finger ends pivotably by means of a pivot attachment to the second rod, it is possible to manipulate the distance from the second finger ends, i.e. the free ends of the fingers, in relation to the longitudinal centre line of the medical instrument over a great distance, i.e., viewed across the longitudinal centre line of the medical instrument, the difference in the distance from the second finger ends to the longitudinal centre line in the second position may be significantly to even substantially greater than in the first position (or, conversely, significantly or even substantially greater in the first position than in the second position). By moving the second rod in relation to the first rod, which may involve rotation and/or translation, the second finger ends, i.e. the free ends of the fingers, can be moved from a first position to the second position. In the case of a so-called 'prosthesis of the type with a tubular element', the first position may, for example, be a position in which the free finger ends, viewed in a radial direction, overlap the distal flange feet from the distal side, and the second position will then be a release position, in which this overlap has been undone. If the medical instrument is then operated from the proximal side by an operator, such as a doctor, and protrudes on the distal side through a prosthesis to be implanted, so that the manipulator lies on the distal side of the prosthesis, it is now very simple to retract the medical instrument in the proximal direction once the prosthesis has been detached. The part of the medical instrument, in particular the manipulator, which, prior to the detachment, lies distally from the prosthesis, can in fact be substantially reduced in size, viewed in the radial direction, and can therefore easily be retracted through the prosthesis. This is also already possible in WO 03/003926, but this is achieved here by means of a release ring, the diameter of which is less than the diameter of the prosthesis, but the diameter of which is furthermore not variable. Consequently, the distal flange feet must bend over a relatively great angular distance, to such an extent that they converge in the distal direction. At any rate, the release ring, having been bent away from the overlapping position, cannot otherwise be retracted through the prosthesis. Due to the fact that, in WO 03/003926, the distal flange feet must therefore bend over a relatively great angular distance in order to return to the radial position, it is not possible to work here with distal flange feet which, prior to implantation/detachment, run purely axially in the overlapping position or are even designed to be conically widening in the radial direction. Furthermore, it is not always possible to bend the distal flange feet so that they converge inwards beyond the axial direction. A prosthesis, particularly a valve prosthesis, may therefore even prevent this or make it impossible. For example, the struts of a stented biological mitral heart valve prosthesis located in a prosthesis of the type with a tubular element will be able to project on the distal side of this tubular element, where they can prevent the bending of the distal flange feet beyond the axial direction. Furthermore, the further the distal flange feet are bent from the radial initial position, the less close they will be able to return in this radial initial position under the influence of the spring action. By then, according to the first aspect, designing the free, second finger ends as pivotable in relation to the first finger ends and by taking the distance of the second, free finger ends on the longitudinal centre line of the medical instrument in the second position as smaller than in the first position, i.e. span reduction, a design is obtained in a simple manner wherein the manipulator, reduced in span, can be retracted from (an organ or otherwise from the body of) the patient through the prosthesis. The term pivotable is understood here according to the first aspect to mean the relative movement of the free second finger ends in relation to the first finger ends. According to the first aspect, the 'pivot movement' may be a pure rotation movement with the first finger ends as the point of rotation, for example if the fingers in the case of the first finger ends are designed as hinged, but, according to the first aspect, this may equally involve a translation movement, a combined rotation and translation movement or otherwise.

According to a further embodiment of the first aspect, the distance from the pivot attachment of the first finger ends to the longitudinal centre line is unchanging.

According to another further embodiment of the first aspect, the pivot attachment comprises a hinge. According to a further embodiment, the hinge may comprise a convex part and a corresponding concave receptacle for the convex part. According to another further embodiment, the fingers may be provided here in each case with the aforementioned concave receptacle. According to the first aspect, a hinge may also be implemented in a different manner. Thus, the fingers in the case of the first finger ends may be provided with a bore through which a ring passes. The fingers are then all attached in a hinged manner to the ring. This ring then extends here around the longitudinal centre line and is then carried by the first rod.

According to a further embodiment of the first aspect, each finger further comprises an inner longitudinal side facing the longitudinal centre line, and an outer longitudinal side facing away from the longitudinal centre line: and the medical instrument further comprises:

an inner guide provided between the longitudinal centre line and the inner longitudinal side of the fingers; and
an outer guide, wherein the fingers are provided between the outer guide and the longitudinal centre line;

wherein the first rod carries the inner guide and the outer guide; wherein each finger has a first curved zone which determines a first finger part which extends from the first finger end to the first curved zone, and a second finger part which extends from the first curved zone to the free end of the finger; wherein, viewed from the first finger ends to the second finger ends, the fingers in the first curved zone bend away from the longitudinal centre line; and wherein, in the second position, the outer guide grips on the outer longitudinal side of the second part of the fingers in order to hold together the fingers in the second position. Due to the fact that the fingers in the case of the first curved zone stand further radially outwards, it becomes possible to implement a relatively large radial span with the fingers without the radial size of the remainder of the medical instrument having to be large. The medical instrument can thus be kept relatively slim, while only the fingers, as a result of the first curved zone, enable a relatively large radial span. The first curved zone, interacting with the inner guide and the outer guide, furthermore readily enables the fingers to be reliably controlled in their position by means of the inner and the outer guide. In the second position, the outer guide ensures that the fingers are reliably held together in a position with a small span.

According to a further embodiment of the first aspect, the inner guide grips here, in the first position, on the inner longitudinal side of the first finger part of the fingers. It is thus ensured that, in the first position, the fingers are held outwards, i.e. are held with a greater span. The fingers, or at least the free ends thereof, are, as it were, pushed away from the longitudinal centre line.

According to another further embodiment of the first aspect, the inner longitudinal side of the first and/or second finger part of the fingers lies here, in the second position, free from the inner guide.

According to another further embodiment of the first aspect, the outer longitudinal side of the first finger part of the fingers lies here, in the first position, free from the outer guide.

According to another further embodiment of the first aspect, the outer guide grips here, in the first position, on the outer longitudinal side of the first finger part of the fingers. Here, in the first position, the outer longitudinal side of the second finger part of the fingers may optionally lie free from the outer guide.

According to a further embodiment of the first aspect, the inner guide grips here, in the second position, on the inner longitudinal side of the first and/or second finger part of the fingers. Thus, in the second position, a confinement of the fingers between the inner guide and the outer guide can be implemented, as a result of which the fingers are held immovably. Here, in the second position, the inner longitudinal side of the first finger part of the fingers may optionally lie free from the inner guide.

According to a further embodiment of the first aspect, the fingers in the aforementioned first curved zone show a curve of at least 30°, in particular a curve of at least 45°, such as a curve of 50° or more. A large span can thus be implemented for the fingers in the wide position compared with a substantially reduced span in the narrow position.

According to a further embodiment of the first aspect, the fingers may show a kinked shape in the first curved zone, at least on the inner longitudinal side of the fingers. A kinked shape creates the possibility for the fingers, in the case of a relatively small displacement along the longitudinal centre line of the instrument, to make a relatively large pivot swing.

According to a further embodiment of the first aspect, the first guide and the outer guide may be immovable in relation to one another. The first guide and outer guide can therefore both be immovably attached to the first rod.

According to a further embodiment of the first aspect, the inner guide is designed, with the aforementioned movement of the first rod in relation to the second rod, in such a way that the fingers move to the first position in order to guide the free ends of the fingers in a radially outward direction in relation to the longitudinal centre line. It is thus possible, with the aid of fingers, to exert a radially outwardly directed compressive force on an object. It is thus possible, for example, in the case of a so-called 'prosthesis of the type with a tubular element', to draw the fingers, from the position in which they overlap the flange feet from the outside, viewed in the radial direction, firstly, in the longitudinal direction of the instrument, away from the flange feet, and therefore to undo the overlapping condition, and then to push these flange feet from the inside with the aid of the fingers from an extended position to the radial position, or at least to support the movement from an extended position to the radial position.

According to a further embodiment of the first aspect, the outer guide is formed by a side of an annular edge provided on the first rod and facing towards the free ends of the fingers, for example formed by a ring or sleeve. It is thus possible to hold the fingers reliably constrained in the second position, at any rate perhaps with an annular element around them. A sleeve offers the additional advantage that it can entirely or partially protect the fingers.

According to a further embodiment of the first aspect, a slit is located in the first position between the fingers and the inner guide, with a radial size such that, with the aforementioned movement of the first rod in relation to the second rod in such a way that the fingers move in the direction of the first position, the free ends of the fingers approach the prosthesis from the inside thereof. It is thus possible, following the release of the flange feet, to support the flange feet during the movement from the extended position to the radial position. After the fingers, moving from the first position to the second position, have been pushed away from the flange feet, they will come to lie closer to the longitudinal centre lines of the instrument as a result of the slit and, on returning in the direction of the first position, will approach the flange feet from the inside.

According to a further embodiment of the first aspect, the outer guide extends around the longitudinal centre line and preferably has a diameter which is smaller than the internal diameter of the prosthesis. It is thus possible, even in the case of a non-expanding prosthesis, to move the part of the medical instrument where the fingers are located through the prosthesis.

It is noted that, according to the first aspect, the fingers can also be designed to be displaceable in a manner which differs from the pivotable manner described above. The pivotable manner described above may possibly be used in combination with such a different manner of displaceability. Examples of a different manner of displaceability of this type are discussed below.

According to a further embodiment of the first aspect, the second rod has a first conical guide surface; and the fingers of the aforementioned plurality of fingers have a guide part at the first finger ends which, through operation of the first rod in relation to the second rod, is shiftable along and in contact with the first conical guide surface to displace the fingers from the aforementioned first position to the aforementioned second position, wherein the distance from the guide parts to the longitudinal centre line in the first position is different compared with the second position. The first conical guide surface and the fingers shiftable along it can be jointly referred to as a head. In this embodiment, it is noted that it is also possible according to the first aspect to provide the medical instrument according to the first aspect with two of these heads. These can then be provided in line with one another, with an interval after one another along the longitudinal centre line of the medical instrument, and the conical guide surfaces can be pointed here in the same direction.

The span of the fingers can therefore be adjusted by supporting the fingers on an oblique guide surface and by displacing them along that oblique guide surface. In the event of upward sliding along the conical guide surface, the span of the fingers increases. In the event of downward sliding along the conical guide surface, the span of the fingers decreases. If required, the fingers can additionally be pivotable, wherein they will be pivotable in particular in relation to the guide part.

According to a further embodiment of the first aspect, the guide part of an aforementioned finger and the remainder of an aforementioned finger are rigid in relation to one another. This is understood to mean that the guide part and the remainder of the finger are immovable in relation to one another. The remainder of the aforementioned finger will therefore not then be pivotable in relation to the guide part. The increase or decrease in the span of the fingers will then take place by means of a pure translation movement of the fingers, said translation movement being oblique in relation to the longitudinal centre line of the medical instrument according to the conicity of the guide surface.

According to a further embodiment of the first aspect with a first conical guide area, the distance from the fingers to the longitudinal centre line in the second position may be greater than in the first position. This means that an increase in the span of the fingers takes place if the fingers move from the first position to the second position. The fingers can therefore accompany the expansion of a prosthesis without the fingers first having to have released the prosthesis. However, this embodiment is also very readily applicable if the medical instrument is required to exert a radial expansion force on an object, such as a prosthesis, or if the medical instrument is required to create or widen a passage. In this latter case, the fingers, in particular on the free ends, will be able to be provided with one or more cutting elements.

According to another further embodiment of the first aspect with a first conical guide surface, the fingers can be slideable from the second position, along and in contact with the guide surface, back in the direction of the first position. The sliding back in the direction of the first position can possibly even take place beyond the first position. If the span of the fingers in the second position is greater than in the first position, the fingers can therefore end in a third position, in which the span of the fingers is smaller than in the first position. If required, the opposite is also possible, i.e. the fingers can be reduced in span from the first position to a second position in order then to be increased in span once more from the second position in the direction of the first position or even beyond the first position. The situation wherein the span of the fingers in the first position is smaller than in the second position and sliding back then takes place from the second position in the direction of the first position will occur in particular if the medical instrument is used as an applicator for expandable prostheses. Fingers can then first expand with the prosthesis to allow the expansion to take place in a controlled manner in order then, once the prosthesis has been released, to return to a position with a span smaller than in the second position, in particular to return to a position with a span even smaller than in the first position. It is thus simple, once the prosthesis has been implanted, to retract the medical instrument once more from the patient. However, this embodiment will also be very suitable if the medical instrument is used as an instrument to create or widen a passage.

According to a further embodiment of the first aspect with a first conical guide surface, the fingers extend parallel to the longitudinal centre line. If the fingers, with at least a part which is adjacent to the free end of the fingers, extend parallel to the longitudinal centre line, they will be able to grip the object, such as a prosthesis, firmly from the outside, taking up relatively little or minimal space.

According to a further embodiment of the first aspect, with a first conical guide surface, the medical instrument further comprises a second conical guide surface (which may be provided on a third rod) and a second plurality of fingers, each with a first finger end and a second finger end, wherein the second finger ends of the second plurality of fingers are free ends; wherein the fingers of the second plurality of fingers have a guide part at the first finger ends which is shiftable along and in contact with the second conical guide surface from a first position to a second position, in which the distance from the guide parts of the second plurality of fingers to the longitudinal centre line is different compared with the first position; wherein the first and second conical guide surfaces are disposed as mirrored in relation to one another, such as facing towards one another; and wherein the free ends of the first plurality of fingers are pointed towards the free ends of the second plurality of fingers, and the free ends of the second plurality of fingers are pointed towards the free ends of the first plurality of fingers. If the first plurality of fingers and the associated first conical guide surface are referred to as a first head and the second plurality of fingers and the associated second conical guide surface are referred to as a second head, this embodiment can be referred to as a design with a mirrored double head. This embodiment with a mirrored double head makes it possible to grip, in particular to grip around, an object, such as a prosthesis, from two opposite sides, by means of the first and second plurality of fingers pointed towards one another. The conical guide surfaces which are similarly pointed towards one another make it possible here to cause the fingers to vary in span simultaneously in the same direction. Depending on the conicity of the first and second guide surfaces, the fingers will then even be able to move to the same extent. It is noted that it is also possible, according to the first aspect, to provide the medical instrument according to the first aspect with two mirrored double heads. These may then be provided in line with one another, with an interval behind one another along the longitudinal centre line of the medical instrument.

In the embodiment of the first aspect with a first and second conical guide surface, the first rod can be connected to the first and/or second plurality of fingers for the operation thereof. Simultaneous operation of the first and the second plurality of fingers is thus possible by moving the first rod in relation to the second rod.

According to a further embodiment of the first aspect, with a first and second conical guide surface, the medical instrument further comprises a third rod which extends along the second rod and is connected to the second plurality of fingers for the operation thereof. It is thus made possible for the second plurality of fingers to be operated independently from the first plurality of fingers by means of the third rod. This furthermore does not prevent the second plurality of fingers from also being connected to the first rod for the operation thereof. It is therefore then possible for the second plurality of fingers to be movable by the first rod and/or by the second rod.

According to a further embodiment of the first aspect, the first rod is provided with a slotted element with slots which extend in the longitudinal direction of the first rod; the fingers of an aforementioned plurality of fingers extend in each case through an aforementioned slot; in the one of the aforementioned first and second positions, the free ends of the fingers of this plurality of fingers project outwards from the slots; and, in the other of the aforementioned first and second positions, the free ends of these fingers are entirely sunk into the slots. In the event that more of a plurality of fingers is provided, the further plurality or the remaining pluralities of fingers may also have an associated slotted element. This may possibly be the same slotted element or a different slotted element. In the case of several pluralities of fingers, it is furthermore also conceivable that only the first plurality of fingers or the second plurality of fingers has an associated slotted element. The slotted element creates the possibility that the fingers, once they have performed their task, such as the holding of a prosthesis or the creation or widening of a passage, are retracted entirely into the closed element, thereby also preventing these fingers, when the medical instrument is retracted, for example following the intervention, from being able to damage surrounding tissue. Damage may easily occur if the free finger ends are provided with cutting elements, but, even if they carry no cutting elements, damage may easily occur merely through contact of the free finger ends with surrounding tissue. Retraction of the medical instrument is thus considerably simplified.

According to a further embodiment of the first aspect with a slotted element, the slots have slot bases which are designed as guide surfaces to guide the free finger ends in a radial direction in the event of displacement of the second rod in relation to the first rod. The slot bases may be conical or tapered, but may also run along a curved and/or staggered line. By designing the slot bases as guide surfaces for the free ends of the fingers, a guiding of the fingers, controlled in a radial direction, is possible in the event of increasing or decreasing of the span thereof.

According to a further embodiment of the first aspect with a slotted element, in the one of the aforementioned first and second positions, in which the free finger ends contact the outside of a hollow prosthesis provided on the instrument, between the fingers and the slot bases, a slit is provided with a radial size such that, in the event of movement of the fingers from the other of the aforementioned first or second positions in the direction of the one of the aforementioned first or second positions, the free finger ends approach the hollow prosthesis provided on the instrument from the inside. It is thus possible, after the prosthesis has first been released by the fingers, to then use the fingers to push from the radial inside against the prosthesis or a part thereof, for example in order to cause the prosthesis to expand or to press on the flange feet thereof or to push them to a radial position. The slit ensures here that the fingers, which, viewed in a radial direction, first overlap the prosthesis from the outside, once this overlapping condition has been undone, can approach the prosthesis or components thereof from the inside.

According to a further embodiment of the first aspect, the medical instrument according to the first aspect further comprises a stop, such as a support ring, which, in the case of a prosthesis provided on the instrument, is located proximally from the prosthesis, and is designed to prevent shifting of the prosthesis in a proximal direction along the instrument. In a corresponding manner, it is also possible for the instrument, in addition to the aforementioned stop or separately from the aforementioned stop, to comprise a further stop, such as a support ring which, in the case of a prosthesis provided on the instrument, is located distally from the prosthesis, and is designed to prevent shifting of the prosthesis in a distal direction along the instrument. If a part of the medical instrument is displaced through the prosthesis, a stop of this type can prevent the prosthesis from also being carried along by the part moving through the prosthesis and also from being displaced in an unwanted manner.

In the embodiment of the first aspect with a stop, the stop may be a support ring which is attached to the first rod by means of a number, such as 2 or 3, of support arms disposed in a distributed manner over the circumference of the first rod. The stop can thus be prevented from obstructing the operator's view of the prosthesis. Separately therefrom, these support arms create space to accommodate a part of the prosthesis when the latter is loaded onto the applicator. This is important, for example, in the case of what is referred to by the person skilled in the art as a 'stented valve'. The stented valve is normally made from biological tissue, such as bovine of porcine tissue, wherein the valve is held 'upright' by means of a set of struts. The set of struts normally consists of a frame of metal or plastic, wherein the locations where the valve flaps coincide (referred to as 'commissures') are held upright in order to prevent the valve from collapsing. Particularly if the struts of a stented valve of this type point in the proximal direction, as may be the case, for example, with a stented aortic valve, it is expedient to extend the width and length of the support arms in such a way that no direct contact occurs between the medical instrument and a valve of this type.

As well as the 'stented valve' described above, a stent also exists which is referred to by the person skilled in the art as a 'valved stent'. A valved stent is primarily a stent in the sense of an expandable and or compressible, normally tubular, element, usually in the form of a meshed structure, in which valve tissue is attached, in most cases by means of adhesions. The stent then automatically holds the commissures extended or upright.

According to a further embodiment of the first aspect, the instrument comprises, in use, a proximal end pointed away from the patient and, in use, a distal end pointed towards the patient, and the plurality of fingers is provided at the distal end. The terms distal and proximal are therefore defined here from the perspective of the operator. Close to the operator is proximal, and far away from the operator is distal. In relation to the patient, this is then precisely the opposite, i.e. distal is directed towards the patient, and proximal is directed away from the patient.

According to a further embodiment of the first aspect, the plurality of fingers here comprises a first plurality of fingers, also referred to as the distal plurality of fingers, of which the first finger ends face towards the distal end of the instrument, and the second finger ends face towards the proximal end of the instrument, and the distance from the free ends of the fingers of the first plurality of fingers to the second rod in the first position is greater than in the second position. In the case of use with a prosthesis, the medical instrument, from the perspective of the operator, will generally project here through the prosthesis, and the fingers, from their non-free end which is supported on the first rod, will point towards the operator with their free ends in order to be able to grip the prosthesis from the distal side thereof facing away from the operator. Following detachment of the prosthesis, it will be then be possible to return the fingers from a large span to a—relatively in relation to the aforementioned large span—small(er) span in order to be retracted through the prosthesis in the proximal direction. In the case of use as an instrument, for example to widen a passage, it is therefore possible to work on the passage from the distal side facing away from the operator and, on completion of said work, to return the fingers to a smaller span in order to be able to retract them simply through the passage.

According to a further embodiment of the first aspect, wherein the medical instrument is used in particular for implanting a prosthesis, in the second position, the largest diameter defined by the first plurality of fingers is smaller than the internal diameter of the prosthesis, in particular smaller than the internal diameter which the prosthesis has after it has been detached from the instrument. Retraction of the first plurality of fingers from the distal side of the prosthesis through the prosthesis to the proximal side can therefore be carried out simply and without damaging the prosthesis.

According to a further embodiment of the first aspect, the second rod is displaceable in the distal direction in relation to the first rod for the purpose of operating the fingers of the first plurality of fingers.

According to a further embodiment of the first aspect, the fingers of the first plurality of fingers, viewed from the distal end to the proximal end, are kinked in a second curved zone in a radially inward direction, wherein this second curved zone is, in particular, such that the part of the fingers of the first plurality of fingers which is located on the proximal side of the second curved zone can extend parallel to the longitudinal direction of the instrument, whereas, viewed from the first finger ends of the first plurality of fingers in the direction of the second curved zone, the part of the fingers of the first plurality of fingers which is located on the distal side of the second curved zone protrudes in a radially outward direction. The part of the fingers protruding in a radially outward direction ensures a large span here, whereas the part extending, in particular, parallel to the longitudinal direction of the instrument enables a reliable grip on a prosthesis carried by the instrument or, in the case of other use, for example, readily enables the performance of work on the inner wall of a passage. Due to the part extending parallel to the longitudinal direction of the instrument which is formed by the part from the second curved zone to the second finger end, this embodiment is very suitable, in particular, for implanting a stent. According to the prior art, it is customary for stents to be delivered in a sleeve to the intervention location. The sleeve is then retracted in situ and the stent expands. If the stent is not positioned at precisely the correct location and the sleeve has already been retracted (too far), the stent can then no longer be repositioned. Retrievable stents are in fact known, but once the sleeve has been retracted too far, it is difficult or impossible to correct this situation. The advantage of this embodiment of the applicator according to the first aspect is that stents can thereby be positioned in a manner which largely permits correction. In any event, the pivotable fingers make it possible, following expansion of the stent, for the stent to be compressed once more and for the stent to be entirely removed or repositioned. In addition thereto, but also entirely separately therefrom, the pivotable fingers enable the stent expansion to be carried out in an extensively and particularly controlled manner.

According to a further embodiment of the first aspect, the free, second finger ends of the first plurality of fingers are provided with a hook with a hook opening which opens in the direction of the first finger ends. In the case of a tubular or annular prosthesis, it is therefore possible to push the fingers through the prosthesis and grip them firmly from the inside by means of the hook opening. This is, for example, an alternative to the fingers overlapping the prosthesis from the outside.

According to a further embodiment of the first aspect, the plurality of fingers may comprise a second plurality of fingers, the first finger ends of which face towards the proximal end of the instrument and the second finger ends face towards the distal end of the instrument. It is noted here that the term 'second plurality of fingers' does not mean that there must also be a first plurality of fingers. The term 'second plurality of fingers' is used here to make a distinction in relation to the first plurality of fingers. In this embodiment with a second plurality of fingers, the instrument may optionally comprise a third rod, which extends along the first rod. This third rod will be present in particular if, in addition to the second plurality of fingers, a first plurality of fingers as discussed above is also provided, if required, in order to be able to displace the second plurality of fingers independently from the first plurality of fingers. In the case of an aforementioned second plurality of fingers, the fingers of this second plurality of fingers, in the absence of an aforementioned first plurality of fingers, will be displaceable by moving the first rod in relation to the second rod. In the case where an aforementioned first plurality of fingers is provided in addition to a second plurality of fingers, the fingers of the second plurality of fingers will be displaceable by moving the first rod in relation to the second rod and/or by moving the first rod in relation to the third rod, if present.

An embodiment with both an aforementioned first plurality of fingers and an aforementioned second plurality of fingers will be referred to below as an embodiment with a 'double head' or a 'double-headed' embodiment. The first plurality of fingers is then associated with a first head and the second plurality of fingers is then associated with a second head, hence the term 'double head'. If the medical instrument is used as an applicator for a prosthesis, it is thus possible to grip the prosthesis from two sides. The prosthesis may then possibly be held in place from one side by one of the two pluralities of fingers, while the other of the two pluralities of fingers is then used on the other side of the prosthesis also to hold the prosthesis in place there or otherwise to manipulate it or to work on the tissue on the other side of the prosthesis. However, a medical instrument according to this embodiment is also usable for purposes other than as an applicator for a prosthesis. The first and second plurality of fingers may, for example, work on a passage from two sides. In the case where the passage is a blood vessel, an obstruction located therein may, for example, be worked on from two sides. However, it is therefore also possible, in the case of an intervention on a heart valve, to work on the heart valve itself and/or the area around this heart valve from two sides.

Assuming that, in the embodiment with a double head, the first plurality of fingers, from the perspective of the operator, is located distally from the second plurality of fingers, the first plurality of fingers can also be referred to as the distal plurality of fingers, and the second plurality of fingers as the proximal plurality of fingers.

As stated above, according to the first aspect, in the case of a double-headed embodiment, the plurality of fingers of the one head may be provided as mirrored in relation to the plurality of fingers of the other head. In this case, the term 'mirrored double head' can be used. However, the plurality of fingers of the one head may, according to the first aspect, also be oriented in the same manner as the plurality of fingers of the other head (i.e. the first finger ends of the one head and the first finger ends of the other head point in the same direction). It is also possible, according to the first aspect, for more than two heads, such as three or four heads, to be provided, with a plurality of fingers for each head.

In the embodiment of the first aspect with a second plurality of fingers, the distance from the free ends of the fingers of the second plurality of fingers to the longitudinal centre line in the first position may be greater than in the second position.

According to a further embodiment of the first aspect with a second plurality of fingers, in the second position, the largest diameter defined by the second plurality of fingers is smaller than the internal diameter of the prosthesis, in particular smaller than the internal diameter which the prosthesis has after it has been detached from the instrument. This, on the one hand, makes it possible for the second plurality of fingers, following the detachment of the prosthesis, also to pass through the prosthesis and, on the other hand, it can also be ensured that the medical instrument, following the detachment of the prosthesis, can easily be retracted from the patient. In any event, the route that will be taken by the medical instrument and the double head thereof will, in principle, be the same as the route via which the prosthesis is thereby brought to its intended location. If the diameter of the head determined by the second plurality of fingers, following the detachment of the prosthesis, is less than the internal diameter of the prosthesis, a simple retraction from the access path to the intervention location, and/or from the organ and/or the patient, is ensured.

According to a further embodiment of the first aspect with a second plurality of fingers, the optionally provided third rod is displaceable in relation to the first rod in the longitudinal direction of the longitudinal centre line for the purpose of operating the fingers of the second plurality of fingers. The third rod may be displaceable here in the proximal direction in relation to the first rod, and/or, conversely, in the distal direction in relation to the first rod.

According to a further embodiment of the first aspect with a second plurality of fingers, the fingers of the second plurality of fingers, viewed from the first finger end to the free, second finger end, are kinked in a second curved zone in a radially inward direction, wherein this second curved zone is, in particular, such that the part of the fingers of the second plurality of fingers which is located on the side of the second curved zone facing towards the second finger end, can extend parallel to the longitudinal direction of the instrument, whereas, viewed from the first finger ends of the second plurality of fingers in the direction of the second curved zone, the part of the fingers of the second plurality of fingers located on the side of the second curved zone facing towards the first finger ends protrudes in a radially outward direction. A large span, on the one hand, and, on the other hand, a firm grip on a prosthesis or a grip over a long surface sector on the inner wall of a passage to be worked on can therefore be implemented with the second plurality of fingers. Due to the part extending parallel to the longitudinal direction of the instrument which is formed by the part from the second curved zone to the second finger end, this embodiment is very suitable, in particular, for implanting a stent. According to the prior art, it is customary for stents to be delivered in a sleeve to the intervention location. The sleeve is then retracted in situ and the stent expands. If the stent is not positioned at precisely the correct location and the sleeve has already been retracted (too far), the stent can then no longer be repositioned. Retrievable stents are in fact known, but once the sleeve has been retracted too far, it is difficult or impossible to correct this situation. The advantage of this embodiment of the applicator according to the first aspect is that stents can thereby be positioned in a manner which largely permits correction. In any event, the pivotable fingers make it possible, following expansion of the stent, for the stent to be compressed once more and for the stent to be entirely removed or repositioned. In addition thereto, but also entirely separately therefrom, the pivotable fingers enable the stent expansion to be carried out in an extensively and particularly controlled manner.

According to a further embodiment of the first aspect with a second plurality of fingers, the free, second finger ends of the second plurality of fingers are provided with a hook with a hook opening which opens in the direction of the first finger ends thereof.

According to a further embodiment of the first aspect, the plurality of fingers may comprise a third plurality of fingers, the first finger ends of which face towards the proximal end of the instrument, and the second finger ends face towards the distal end of the instrument; and wherein the distance from the free ends of the fingers of the third plurality of fingers to the longitudinal centre line in the first position is greater than in the second position. It is noted here that the term 'third plurality of fingers' does not mean that there must also be a second plurality of fingers or a first plurality of fingers. The term 'third plurality of fingers' is used here to make a distinction in relation to the first and second plurality of fingers. The so-called third plurality of fingers will, in principle, not be used in combination with the first plurality of fingers, but it is nevertheless optionally possible for the third plurality of fingers to be used in combination with the second plurality of fingers and/or in combination with the first plurality of fingers. A double-headed embodiment is also involved in the case of the third plurality of fingers in the presence of an aforementioned first or second plurality of fingers.

According to a further embodiment of the first aspect with a third plurality of fingers, in the second position, the largest diameter defined by the third plurality of fingers is smaller than the internal diameter of the prosthesis, in particular smaller than the internal diameter which the prosthesis has after it has been detached from the instrument. It is thus ensured, following the detachment of the prosthesis, that an instrument with a third plurality of fingers can easily be retracted through the prosthesis. It is furthermore ensured that, even if the medical instrument here is not an applicator for a prosthesis, the medical instrument can be retracted following the intervention along the path via which it was first delivered to the intervention location.

According to a further embodiment of the first aspect with a third plurality of fingers, the second rod is displaceable in relation to the first rod in the longitudinal direction of the longitudinal centre line for the purpose of the aforementioned operation of the fingers of the third plurality of fingers. This displacement in the longitudinal direction of the longitudinal centre line may be a displacement of the second rod in the distal direction in relation to the first rod and/or a displacement of the second rod in the proximal direction in relation to the first rod.

According to a further embodiment of the first aspect with a third plurality of fingers, the fingers of the third plurality of fingers, viewed from the first finger end to the second finger end, are kinked in a first curved zone in a radially outward direction. The area is thus increased in span.

According to a further embodiment of the first aspect with a third plurality of fingers, the free, second finger ends of the third plurality of fingers are provided with a hook with a hook opening which opens in the proximal direction, i.e. in the direction of the first finger ends. Thus, the fingers of the third plurality of fingers, in the case of a prosthesis, can reach from the proximal side of the prosthesis (facing towards the operator) inside through the prosthesis to the distal side of the prosthesis (facing away from the operator) in order to be able to grip there on the prosthesis from the inside by means of the hook.

According to a further embodiment of the first aspect with a third plurality of fingers, the fingers of the third plurality of fingers, viewed from the first finger end to the free, second finger end, are kinked in a second curved zone in a radially inward direction, and this second curved zone is, in particular, such that the part of the fingers of the third plurality of fingers which is located on the side of this second curved zone facing away from the first finger ends, can extend parallel to the longitudinal direction of the instrument, whereas, viewed from the first finger end of the third plurality of fingers in the direction of the second curved zone, the part of the fingers of the third plurality of fingers which is located on the side of the second finger ends adjacent to the second curved zone, protrudes in a radially outward direction. It can thus be achieved that the fingers may, on the one hand, have a relatively long length in the longitudinal direction of the instrument, and, on the other hand, for a relatively large part, i.e. up to the first curved zone, can be designed with limited dimensions, viewed in a radial direction.

According to a further embodiment of the first aspect, the instrument is sterile. The term 'sterile' is understood here to mean a degree of sterility which is customary for medical instruments.

According to a further embodiment of the first aspect, the instrument according to the first aspect is made from one or more medically acceptable materials. The term 'medically acceptable materials' is understood to mean materials which, as is customary in the case of medical instruments, are inert in relation to, in particular, the human body, but usually the animal body also. Examples of medically acceptable materials of this type include metals such as stainless steel, titanium, nitinol, and plastics such as polypropylene, nylon and Teflon.

According to a further embodiment of the first aspect, the first rod is provided with a carrier part to carry a prosthesis, and the fingers of the at least one plurality of fingers are movable in relation to the carrier part. Here, the fingers will, in particular, be movable in the direction of the longitudinal centre line of the medical instrument and/or in the direction perpendicular to the longitudinal centre line.

According to a further embodiment of the first aspect, the instrument is intended for the implantation of a prosthesis.

According to a further embodiment of the first aspect, the medical instrument further comprises a prosthesis, wherein the free ends of the fingers in the one of the aforementioned first and second positions grip on the prosthesis and, in the other of the aforementioned first and second positions, preferably lie free from the prosthesis.

According to a further embodiment of the first aspect, the prosthesis has a tubular element, i.e. a hollow element which is open at two opposite axial ends. This is not yet entirely the same as a so-called 'prosthesis of the type with a tubular element'. The distal and/or proximal flange and distal and/or proximal flange feet may be absent. Apart from a so-called 'prosthesis of the type with a tubular element', the prosthesis here may therefore also be a different prosthesis with a tubular element, such as a generally known stent.

According to a further embodiment of the first aspect, the 'prosthesis of the type with a tubular element' has a distal and proximal flange which extend along the circumference of the tubular element, wherein the distal and/or proximal flange has flange feet which are bendable from an extended position extending in an axial direction to a radial position extending in a radial direction. In other words, the prosthesis is, in particular, a prosthesis as described in detail in earlier PCT applications of the inventor, i.e. WO 00/24339, WO 00/44311, WO 03/003926, WO 03/082121 and WO 2005/092246. These PCT applications are all included by reference in the present application as far as details of the 'prosthesis of the type with a tubular element' are concerned.

According to a further embodiment of the first aspect with a carrier part, the carrier part is designed to grip on the inside of the tubular element or organ. A tubular element or organ can thus be supported on the carrier part, as a result of which the positioning of the tubular element or organ in relation to the medical instrument, and therefore more accurate delivery to the intervention location, are more effectively ensured.

According to a further embodiment of the first aspect with a prosthesis loaded thereon, biological tissue is located between the prosthesis and the instrument.

According to a further embodiment of the first aspect, the prosthesis is a heart prosthesis, such as a heart valve prosthesis or ring prosthesis.

According to another further embodiment of the first aspect, the prosthesis is one from the group of:

the new and inventive ring prosthesis to be described in detail below (second aspect); and/or the new and inventive stent to be described below (third aspect).

SECOND ASPECT

According to a second aspect, the present application relates to a new and inventive ring prosthesis. Ring prostheses are prostheses which are used to constrict the through-flow passage of a heart valve or natural or artificially disposed passages in tissue. According to the second aspect, a ring prosthesis of this type can also be used in combination with an artificial or donor heart valve to draw the surrounding tissue firmly against the outer circumference of the new heart valve and therefore prevent leakage around the heart valve. The constricting ring prosthesis can first be disposed here in the tissue and the valve prosthesis can then be placed in or over it. It is advantageous here if the ring prosthesis, despite its constricting effect, can then still be widened so that it can still be stretched to some extent by the valve prosthesis and the valve prosthesis can pass through it. The ring prosthesis may also be integrated, as it were, in advance with the valve prosthesis. The ring prosthesis may then be located here, for example, on the underside or on the upper side of a fixed proximal flange of a prosthesis of the type with a tubular element. A ring prosthesis of this type may be connected here to the valve prosthesis with adhesions, but the upper flange of a valve prosthesis of this type may also, for example, have radially running openings or guide rods which guide the ring prosthesis in the radial movements of the ring prosthesis. However, the upper flange of a valve prosthesis of this type may also be designed, as it were, as double-walled with radially running openings on the underside of an upper flange of this type, wherein the ring prosthesis is located inside this upper flange and the pins of the ring prosthesis which are described below project distally through these radially running openings. Prior to the implanting of a heart valve prosthesis of this type, the distal flange feet of the heart valve prosthesis would first be extended and the diameter of the internal ring prosthesis would be stretched, and possibly the feet thereof would be extended in an axial direction and temporarily held in that condition, so that, following the implantation of the combined product, the distal flange feet of the heart valve prosthesis extend radially, and the diameter of the ring prosthesis has decreased, and the feet of the ring prosthesis have possibly assumed a non-axial direction. It is thus achieved that the tissue around the valve prosthesis is drawn towards the valve, and the risk of leakage around the valve is reduced. Separately from the ring prosthesis, the same effect can be achieved by fixing or positioning on or in the upper flange separate pins or pins interconnected in a manner other than the manner described here for the ring prosthesis, said pins essentially comprising a horizontal part and a vertical part (the actual pin), and wherein the horizontal part can be displaced in a resilient manner in a radial direction, wherein this part, prior to insertion, is stretched in a radially outward direction in order to allow the horizontal part to shorten in a resilient manner in a radially inward direction following the insertion of the vertical part, the actual pin itself, into the tissue. The pins must then be held temporarily in a mechanical manner by an obstacle in the radially outward position, after which, following removal of this obstacle, which may very well be one of the applicators described in this application, the pins move, or at least are inclined to move, radially inwards. The horizontal part of pins of this type would then have to be connected directly and in a radial direction to the upper flange, and the resilience could be created by designing the horizontal part as a spring or in an waved or zigzag form or otherwise in a resilient manner.

According to the second aspect, the ring prosthesis for constricting the through-flow passage of a heart valve comprises:
a first ring; and
anchoring elements to attach the first ring to tissue surrounding the through-flow passage to be constricted, wherein each anchoring element is attached to the first ring;
wherein the first ring is formed from a wire which, viewed in the circumferential direction of the first ring, extends along a waved pattern in such a way that the diameter of the ring prosthesis is constrictable from a first, relatively wider, condition to a second, relatively narrower, condition, wherein the wave lengths of the waves of the wave pattern in the aforementioned first condition are greater than in the aforementioned second condition. The ring prosthesis according to the second aspect is based on the principle that the circumference, and therefore the diameter, of the waved ring can be constricted by drawing the waves closer together, viewed in the circumferential direction of the ring, i.e. in the extension direction of the waves. Successive peaks and troughs of the waves therefore then move closer together. Narrowing of the ring prosthesis will therefore be accompanied by a reduction in the wave length and an increase in the wave height, whereas widening of the ring prosthesis will be accompanied by an increase in the wave length and a reduction in the wave height.

The advantage of the waved pattern is that a ring prosthesis of this type according to the second aspect, once it has been implanted, may fluctuate in diameter to some extent in order to be able to move in conjunction with (pressure) pulses which occur as a result of the effect of the heart, as a result of which the passages through which the blood is pumped have a tendency to fluctuate in diameter. Furthermore, the waved pattern also enables the ring prosthesis, if it appears to be slightly too small at the intervention location, first to be widened before it is attached to the surrounding tissue for constriction thereof.

According to the second aspect, the waved pattern therefore forms a continuous curve, i.e. the wire extends along a continuous curved path or, in other words, the wire forms a continuous curved path. The term 'continuous curve' is understood here to mean a curve of which the (mathematical) direction coefficient runs gradually, as in the case, for example, of a parabola or sinusoidal form. Abrupt transitions, as a result of which the wire would be susceptible to breaking, are thus avoided.

The anchoring elements in a ring prosthesis according to the second aspect can be designed in many different ways. If a suture is used to sew surrounding tissue, for example, to the peaks of the waves, the suture will form the anchoring elements and the ring can therefore even be delivered without anchoring elements having been previously attached thereto. The anchoring elements may also comprise clamps, consisting, for example, of a so-called lower and upper flange as described in the aforementioned PCT applications of the inventor, i.e. WO 00/24339, WO 00/443111, WO 03/003926, WO 03/082121 and WO 2005/092246.

According to a further embodiment of the second aspect, the waved wire is in the first condition and the ring, in this first condition, is under a pre-tension, as a result of which the ring is inclined to constrict to the second condition. The ring is then fixed here in the first condition and, once the fixing has been undone, will be inclined to move towards the second condition under the influence of the pre-tension. This can be implemented, for example by designing the wire in the form of a memory material, such as a memory metal. An example of a memory metal of this type is a nitinol alloy. If the ring is made from a nitinol alloy (or other memory metal), the ring can be 'frozen' by means of a temperature treatment, in particular a cold treatment, in the wide first condition. The ring can then be heated and, when a threshold temperature is exceeded, the 'frozen' pre-tension will be released, so that the ring can return to the narrower second condition. A different way of implementing a ring pre-tensioned in the wider first condition is to design said ring from a 'normal' resilient, elastic material (such as a spring-steel-type material), and then to stretch the ring, while the pre-tension is built up here, to the first condition and fix it by means of (mechanical) obstacles in this first condition. When the mechanical obstacle is removed, the pre-tension is then released and the ring will be inclined to return to the narrower, second condition. Combinations of pre-tension created with temperature treatment of memory material and a temporary mechanical obstacle are of course also possible.

According to a further embodiment of the second aspect, the anchoring elements comprise pins. These pins are attached at one end to the ring prosthesis and, viewed from this one end, may extend in particular in the axial direction of the first ring. This makes it possible to press the pins into the natural annulus around a heart valve and thereby attach the ring prosthesis. The ring prosthesis can then be constricted.

According to the second aspect, the constriction of the ring prosthesis may be effected by exerting mechanical force upon it. It is also very easily conceivable for the ring prosthesis, in particular the waved wire thereof, to be made from a memory material, such as a memory metal (for example a nitinol alloy) or a memory plastic, such as a polymer with memory properties. A ring prosthesis of this type, once it has been attached and has reached body temperature or has possibly been heated to a slightly higher temperature, can then return to an original narrower diameter which is, as it were, stored in the memory of the memory material.

According to a further embodiment of the second aspect with pins, at least a part of the pins is pre-tensioned in order to move the free ends, once the pre-tension has been released, in relation to the ends of the pins attached to the ring prosthesis. All pins can therefore also be pre-tensioned here. This pre-tensioned condition is maintainable, for example, with the aid of a mechanical obstacle which is removed when the ring prosthesis is implanted. However, this pre-tension can also be implemented by means of a memory material, wherein the pins are then 'frozen' in the axial condition, normally by means of a temperature treatment. If a specific threshold temperature is exceeded, the pins will then be inclined to return to a condition in which the free ends are displaced in relation to the ends attached to the ring prosthesis. The anchoring in surrounding tissue can be improved by displacing the free ends of one or more of the pins in relation to the ends of the pins attached to the ring prosthesis. The movement of the free ends of the pins in relation to the ends attached to the ring prosthesis can be implemented by positioning the pins, wherein their shape does not change, obliquely or more obliquely in relation to the axial direction of the ring prosthesis and/or by bending the pins.

According to a further embodiment of the second aspect, the pins, or at least a part thereof, are pre-tensioned in order, following release with the free ends, to:
- to be displaced in a radially inward direction; and/or
- to be displaced in a radially outward direction; and/or
- to be displaced in a tangential direction; and/or
- to be displaced in pairs towards one another.

The term 'displaced in pairs towards one another' is understood here to mean that the free ends of two pins move towards one another and possibly thereby cross one another. Two such pins therefore form a type of anchoring clamp. The radial displacement of the free ends of the pins may even take place to the extent that the pins, as it were, curl up over 90° or even more, up to 180°. It will be clear that this improves the anchoring of the pins in the surrounding tissue.

According to a further embodiment of the second aspect, the anchoring elements are disposed in a distributed manner, in particular evenly distributed, over the circumference of the first ring.

According to a further embodiment of the second aspect, the ring prosthesis further comprises a plurality of segments disposed in a distributed manner over the circumference of the first ring, wherein each segment is attached to the first ring. According to a further design thereof, segments adjacent in the circumferential direction may, in the first condition, lie at a distance from one another leaving the intermediate space free, and, in the second condition, lying against one another, may form an essentially closed second ring which prevents further constriction. It can thus be achieved that the constriction of the ring prosthesis is limited to a predefined diameter. The ring segments may therefore have a limiting function. An entirely different function of the ring segments is a support/attachment function. In addition to or entirely separately from the limiting function, the ring segments may also serve to support a further prosthesis which is to be implanted in or near the ring prosthesis and/or to affix a further prosthesis of this type. In the case of this support/attachment function, it is also possible for only a few, at least 2 or 3, ring segments to be provided, which are distributed over the inner circumference of the waved wire ring and which together cannot form a complete ring. The ring segments do not therefore have to be able to form a closed ring for the support/attachment function. There do not even have to be any ring segments.

According to a further embodiment of the second aspect, the amplitude of the waved pattern extends in the radial direction of the ring. In particular, the amplitude of the waved pattern extends here at an angle of 30° to 90° in relation to the axial direction of the first ring. The ring prosthesis, following implantation, may therefore lie close to annulus tissue or other tissue oriented radially in relation to the ring prosthesis.

According to a further embodiment of the second aspect, the position of the amplitude of the waved pattern, viewed along the circumference of the first ring, varies in relation to the axial direction of the first ring. Thus, if the ring is used in the case of the mitral valve, it may be advantageous, for example, if the position of the amplitude is designed over a ⅓ or ¼ part of the ring with an angle which is narrower in relation to the axial direction than in the case of the remainder of the ring, said part lying on the anterior or septal side of the mitral annulus.

According to a further embodiment of the second aspect, the ring prosthesis comprises at most one aforementioned anchoring element for each cycle of the waved pattern. It can thus be achieved that anchoring elements adjacent in the circumferential direction cannot obstruct one another. The anchoring elements can be attached here in each case to the first ring in the same part of the cycle of the waved pattern.

According to a further embodiment of the second aspect with one anchoring element for each wave cycle, the anchoring elements are attached to the inward-facing troughs of the waved pattern, in particular at the midpoint of said troughs. The anchoring elements here may, for example, be pins or clamping mouths, as will be discussed below. If the anchoring elements are located in the trough of the waves, the implementation may be such that, insofar as possible, following implantation, the entire ring prosthesis, and therefore the material thereof which is foreign to the body, is located outside the valve passage.

It is noted that the anchoring elements may also be provided between the peaks and troughs, for example midway between the peaks and troughs.

According to a further embodiment of the second aspect, in each case with one anchoring element for each cycle, the anchoring elements are attached to the outward-facing peaks of the waved pattern, in particular at the midpoint of said peaks. The anchoring elements here may be the pins discussed earlier.

According to a further embodiment of the second aspect, the waved pattern is a sinusoidal pattern. The term 'sinusoidal pattern' is understood in particular to mean a pattern which runs along a line with a curve continuously changing according to a sine-wave pattern. Sharply angled parts which form a thrombosis in contact with blood or can otherwise cause disruption to the blood flow are largely avoided here. A sinusoidal waved pattern enables an effectively controllable narrowing of the diameter. Furthermore, a sinusoidal waved pattern enables a flexible small diameter adaptation in response to pressure fluctuations in the bloodstream, or the cyclical heart muscle action.

According to a further embodiment of the second aspect, the waved pattern comprises 8, 9, 10, 11, 12, 13, 14 or 15 wave cycles, wherein the first ring has a diameter in the 15 mm to 50 mm range. The diameter here is in particular related to the diameter of the ring prosthesis as the latter is delivered ex-works. The ring prosthesis may be delivered ex-works in an expanded condition in order to narrow following implantation. However, the ring prosthesis may also be delivered ex-works in a constricted condition, wherein the operator will then widen the ring prosthesis prior to or during implantation, for example by cooling it by placing it on a cooled holder or by placing it in ice water and actively stretching it, in order to allow the ring prosthesis to narrow once more following implantation, for example through contact with the warm body tissue or blood, or by actively heating it with a warm holder, or with a warm liquid. For an application of the ring prosthesis according to the second aspect in the case of a mitral or tricuspid valve, the diameter will normally lie in the 25 to 40 mm range. In the case of aortic valves, the required diameters for the ring prosthesis will lie, in particular, in the 17 mm to 29 mm range. If the ring prosthesis is used to constrict natural or artificially disposed passages elsewhere in the body, the diameters may be larger or smaller. For use in the case of an aortic valve, the ring prosthesis according to the second aspect may also have, along with the waved pattern, i.e. superimposed thereon, a sinusoidal form of 3 sine waves in the circumferential direction.

According to a further embodiment of the second aspect, viewed in the direction of the wave height, the distance between the peaks and troughs of the waves lies in the 0.5 mm to 20 mm range, such as in the 0.5 to 3 mm range. Ring prostheses with such dimensions for the wave pattern can be used in humans for virtually any type of heart valve.

The diameter of the first ring, the wave height and the number of wave cycles may vary according to the type of heart valve and according to the patient.

According to a further embodiment of the second aspect, the anchoring elements may comprise clamping mouths with a first jaw part and a second jaw part which is movable in relation to the first jaw part in order to clamp tissue between the jaw parts. Clamping mouths of this type are known per se from the aforementioned PCT applications (i.e. WO 00/24339, WO 00/443111, WO 03/003926, WO 03/082121 and WO 2005/092246 of the inventor), and are normally referred to in said applications by the term 'lower and upper flange feet'.

According to a further embodiment of the second aspect with clamping mouths, the clamping mouths can be brought from a closed condition against spring action to an open condition, and the clamping mouths can be returned from the opened condition to the closed condition under the influence of said spring action. The spring action may be provided here by means of a conventional mechanical spring action. However, the spring action may also be provided by using memory material. According to a further embodiment, the clamping mouths then also comprise a memory material which produces said spring effect, wherein the clamping mouths are fixed in the opened condition by means of a temperature treatment (which is understood in all aspects of this application to mean not only a treatment at a higher temperature, also referred to as heat treatment, but also a treatment at a lower temperature, also referred to as cold treatment) in order to be able to return to the closed condition if a threshold temperature is exceeded or understepped. The memory material here may be a memory metal, such as nitinol, but may also be a memory plastic, such as a memory polymer. Combinations of memory metal and memory plastic are also conceivable. In the case of nitinol, the clamping mouths may be fixed in the opened condition by means of a cold treatment, in order to return later to the closed condition if they warm up and exceed the threshold temperature.

According to a further embodiment of the second aspect with clamping mouths, the clamping mouths are provided on the inner circumference or outer circumference of the ring prosthesis and are pointed with the mouth opening in a radially outward direction. If the clamping mouths are provided on the inner circumference and are oriented with the mouth opening in a radially outward direction, it is optionally possible to design the ring prosthesis in such a way that, viewed in the axial direction, the clamping mouths are essentially entirely overlapped by a surface which is defined, on the one hand, by the inner contour of the wire determined by the wave troughs and, on the other hand, the outer contour of the wire determined by the wave peaks.

According to a further embodiment of the second aspect, the clamping mouths comprise one or more teeth which are attached, in particular, to a jaw part and point towards the opposite jaw part. The adhesive force on the tissue clamped in the clamping mouths can thus be increased.

The basic shape in the case of a ring prosthesis according to the second aspect is determined by an imaginary line which interconnects the wave peaks. Alternatively, but essentially equivalent, this basic shape can also be determined by an imaginary line which interconnects the wave troughs, or the imaginary line which forms the midpoint between the wave troughs and wave peaks. On the basis of this basic shape definition, it is noted that the basic shape of the ring prosthesis according to the second aspect may be adapted to the shape of the relevant heart valve where it will be used. The basic shape does not therefore have to be a circular shape, and the designations ring prosthesis, first ring and second ring do not then suggest a circular shape either (although a circular shape is not excluded). The basic shape may also be an elliptical, bean, kidney or other shape. The basic shape may even be non-symmetrical. Where the diameter of the ring prosthesis is mentioned above, this is not therefore intended to mean that the ring prosthesis must be circular, but is intended to designate a dimension across the axial direction of the ring prosthesis. As far as the basic shapes for ring prostheses according to the second aspect are concerned, it is pointed out in particular that they may be bean-shaped, for use, in particular, in the case of a mitral or tricuspid valve. It is furthermore pointed out that the basic shape does not have to be 2-dimensional, but may also be a 3-dimensional shape. For example, in the case of an aortic valve, the natural annulus runs, for example, according to a sinusoidal pattern of 3 sine waves. Correspondingly, the basic shape for a ring prosthesis according to the second aspect which is intended for an aortic valve may follow a sinusoidal pattern, such as a sinusoidal pattern with 3 sine waves. This sinusoidal pattern extends, on the one hand, where the propagation direction of the sine wave is concerned, along the circumference of the ring prosthesis and, on the other hand, where the amplitude direction of the sine wave is concerned, in the axial direction of the ring prosthesis. An example of a further explanation of a sine-wave pattern of this type can be found in WO 00/44311 of the inventor, in particular in FIG. 7 of WO 00/44311 and in the description associated with FIG. 7 of WO 00/44311.

THIRD ASPECT

According to a third aspect,
this application also relates to a new and inventive stent.

A stent is a tube, normally made of metal, with an open grid structure, often with a cylindrical shape, which is compressible, and, if held in the compressed condition, often by means of a mechanical obstacle, such as a tube or a sleeve, can be navigated to a required intended location in the body of a patient. Once the stent has reached the intended location, the stent can be released by removing the tube or sleeve, after which the stent will open out through radial expansion, and can be affixed against the wall of a cylindrical channel, such as e.g. a blood vessel. If a stent is then used to affix a heart prosthesis, referred to as a valved stent, the following problems arise. The first problem is that, at places where a natural heart valve is located in the heart, this place and the immediate surroundings thereof are not always purely cylindrical in shape, or are even on the whole non-cylindrical in shape. The second problem is that a heart valve prosthesis has a specific optimum diameter, so that deviation therefrom is not possible if an optimum result is to be achieved.

The first problem may mean that the stent is poorly affixed in situ. In the case of the aortic valve and the pulmonary valve, this is not a problem, seeing that these valves are located on the underside of essentially cylindrical channels, i.e. the aorta and the pulmonary artery respectively. However, in the case of the mitral valve and the tricuspid valve, these valves are, on the whole, not located in a cylindrical channel, but between two relatively wide spaces, i.e., respectively in the case of the mitral valve, between the left atrium and the left ventricle, and, in the case of the tricuspid valve, between the right atrium and the right ventricle. A cylindrical stent cannot be affixed or cannot be firmly affixed there. To counteract this, it is known from the current prior art that a stent can also widen or narrow. For example, in the case of an aortic valved stent, the stent can be widened on the upper side (downstream), so that the stent can be affixed at a distance from the original aortic valve, i.e. in the ascending aorta. If an affixing at a distance of this type were to be used in the case of the atrioventricular valves, this would then require not only a large amount of stent material, but also a stent with a large diameter. Material of this type would act as an obstruction to the blood flow of the chambers and the atria. The atrial tissue is very thin and will offer little resistance to the stent, and could easily be perforated by the stent. Furthermore, the anatomy of the atria is subject to great variation. Such broadenings of the stent at a distance from the valve annulus do not result in a mechanically effective adhesion, compression or hooking in the region of the valve annulus, and cannot prevent leakage around the stent in the region of the annulus.

As mentioned, the second problem is that a heart valve has a specific optimum diameter. A mechanical heart valve prosthesis has a fixed diameter. A biological heart valve prosthesis comprises valve flaps and is deformable, possibly also compressible and expandable, and has an optimum diameter, wherein the passage for blood is optimum. If the valve diameter is overstretched, this may result in damage to the valve flaps, or even incomplete closure of the valve flaps. If the biological heart valve prosthesis is not fully expanded, the valve flaps may act as an obstruction to the blood flow, or the shape of the valve flaps may be deformed, or blood turbulence may occur, which may result in reduced durability of the valve. It is therefore important for a possible first compressed biological valve prosthesis to be expanded during implantation in such a way that the valve obtains its optimum diameter. If such a valve is then fixed in a stent, in most cases through adhesions, or otherwise, it is then clear that, at the time when the biological valve prosthesis has attained its optimum diameter, it cannot further expand, as a result of which the radial expansion forces of the stent at that moment are reduced to virtually zero. At any rate, the valve then retains the stent. In other words, the adhesive force of the stent is virtually zero at the time when the valve is fully expanded. To avoid this problem, it is generally advised to use a slightly larger valve (and stent) diameter than would be strictly necessary, with all of the aforementioned disadvantages as far as the incomplete opening or deformed shape of the valve flaps is concerned. An alternative is to use a wider stent, which is affixed at a distance from the valve annulus. Furthermore, the current aortic valved stents are used in practice in combination with a balloon dilatation of often calcified diseased aortic valves, so that the valve and stent are affixed in the dilated and calcified diseased valve, wherein the stent hooks onto the calcareous diseased valve tissue. If, in the case of a diseased valve, the diseased valve is entirely removed, the valved stent will only be able to be affixed if a diameter is used which is actually too large, or if the attachment actually takes place at a location other than in the region of the valve annulus.

According to the third aspect, the object of this application is to overcome one or more of the aforementioned problems relating to stents.

This object is achieved according to the third aspect by providing a stent, comprising:

a tubular element which is expandable in a radial direction from a compressed condition to an expanded condition, and which has a proximal and distal end;

a proximal flange of proximal flange feet provided around the tubular element; and a distal flange of distal flange feet provided around the tubular element;

wherein the distal and proximal flange feet are attached with a fixed end to the tubular element and have another end which is free;

wherein the distal and proximal flange feet have a radial position, in which the free ends of the flange feet point in the radial direction for anchoring with surrounding tissue;

wherein the distal flange feet are pivotable from an extended position, in which the distal flange feet lie in the longitudinal direction of the tubular element, to the position extending in the radial direction; and wherein the distal flange feet are provided distally from the proximal flange feet. As far as the so-called proximal and distal flange feet are concerned, it is noted here that they are essentially comparable with distal and proximal flange feet (or arms) as known from WO 00/24339, WO 00/44311, WO 03/003926, WO 03/082121 and WO 2005/092246. The stent according to the invention is based on the insight that the knowledge disclosed by the aforementioned PCT application is also readily applicable to stents in order to attach the latter to surrounding tissue. The anchoring to surrounding tissue is carried out here in that surrounding tissue is clamped between the distal and proximal flange feet and/or in that the distal and proximal flange feet anchor themselves in the surrounding tissue as a clamp, in particular with distal and proximal flange feet pointing towards one another or crossing one another. The tubular element of the stent according to the invention will not normally be a solid element but a grid-like element as is generally known in the medical field in the case of stents. According to a further design, the free ends of the distal flange feet, in the extended position, optionally point in the distal direction.

It is noted that, according to the third aspect, the tubular element does not have to have the same diameter overall. The tubular element may, for example, have a first and second zone, wherein the diameter in the first zone is smaller than in the second zone. The proximal and/or distal flange may then be provided in the first and/or second zone. If the proximal and/or distal flange are provided in the first zone, where the diameter is smaller, it is even conceivable that the circumferential contour, defined by the ends of the flange feet in the case of the proximal or distal flange in the radial position, has a diameter which is smaller than the diameter of the second zone.

In the case of the stent according to the third aspect of this application, the proximal flange feet may also optionally be pivotable from an extended position, in which the proximal flange feet lie in the longitudinal direction of the tubular element, to a radial position extending in the radial direction. In this design, the free ends of the proximal flange feet, in the extended position, may optionally point in the proximal direction.

It is noted that the extendable distal flange feet, in the extended condition, may also lie along the tubular element and also in the extension of the tubular element if they are provided on one end of the tubular element. The same applies to the proximal flange feet, if they are extendable. Extendable proximal flange feet may, in the extended condition, lie along the tubular element and also in the extension of the tubular element, if they are provided on one end of the tubular element.

By combining the so-called 'tubular element' from WO 00/24339, WO 00/44311, WO 03/003926, WO 03/082121 and WO 2005/092246 of the inventor with a stent, wherein the lowermost flange is bendable and the uppermost flange may also optionally be bendable, a so-called valved stent may be firmly and reliably affixed in a mechanical manner in the region of the valve annulus. The diameter of the expandable tubular element may match the optimum diameter of the valve prosthesis. The stent is then essentially no longer necessary, as is the case in the prior art, in order to affix the valve prosthesis, but is primarily a tool to hold the biological valve extended and upright. However, it is possible, in the case of the stent according to the third aspect of this application, for the total product of the stent and valve to be compressible and therefore to be able to be brought more easily to the intervention location in the body of the patient.

Other advantages of the stent according to the third aspect of this application compared with the current (aortic) valved stents are that, insofar as the current valved stents make use of stents to affix the stent to the surrounding tissue at a distance from the valve annulus, this increases the quantity of the material foreign to the body and this stent material may have a thrombogenic effect. Due to the greater length of the stent from the prior art, an obstruction to the blood flow through the coronary arteries will more readily occur, and it is more difficult for the surgeon to find space on the ascending aorta for so-called proximal anastomoses with bypass grafts. Problems of this type can be prevented with the stent according to the third aspect of this application in that it is affixed very locally, preferably in the region of the valve annulus.

In a further embodiment of the third aspect, the fixed ends of the distal flange feet are located at a distance from the distal end of the tubular element which is larger than twice the length of the distal flange feet; and the fixed ends of the proximal flange feet are located at a distance from the proximal end of the tubular element which is greater than 2× the length of the proximal flange feet.

In the case of a stent according to the third aspect, the proximal and distal flange feet interact to clamp or firmly grip surrounding tissue between them after they have bent in the direction of the radial position. It must be noted that the distal and proximal flange feet defined here do not have to assume a purely radial position, as what matters here is that they anchor themselves in the surrounding tissue. It is conceivable here that surrounding tissue holds the flange feet essentially in a largely axial position. The flange feet may possibly be provided here with hooks or small pins, or may even be designed as hooks for further anchoring in the surrounding tissue.

According to a further embodiment of the third aspect, the stent comprises a heart valve provided in the tubular element. This heart valve may be a natural donor valve, normally referred to by the person skilled in the art as a 'biological valve', such as from a human, known to the person skilled in the art as a 'homograft', or animal, known to the person skilled in the art as a 'xenograft'. According to a further embodiment, the donor valve is a biological valve selected from the group of:
  porcine valves, such as a reconstructed or non-reconstructed aortic valve from a pig, including the three valve flaps;
  bovine valves, such as a reconstructed or non-reconstructed valve, for example with three valve flaps reconstructed from the pericardium of a bovine animal;
  equine valves;
  human valves; or
  kangaroo valves.

None of these biological valves needs to be entirely biological, but, in addition to biological material, may also comprise non-biological material such as plastic or metal. Furthermore, these biological valves may or may not be a reconstructed valve. A reconstructed valve is generally understood to be a valve of biological material, from which the original anatomical link has been broken. A reconstructed valve may be formed by combining a plurality of biological components into a valve. The plurality of biological components may originate from the same donor or from different donors. It is even conceivable for the biological components to originate from different types of donor, for example one or more components originating from a pig in combination with one or more components originating from a bovine animal, or one or more components originating from a human in combination with one or more components originating from different or the same types of animal.

According to a further design of the third aspect, the tubular element and the distal and proximal flange feet comprise a single piece of material. The unit may be manufactured, for example, by laser burning or etching from a single piece. This single piece may be a tubular or other form of a plate of material, for example of metal such as stainless steel or a nitinol alloy. The plate material may be in a flat or curved condition prior to the formation of the unit and may be closed to a tubular form following removal of material, but the plate material may also have a tubular configuration prior to the removal of material. Furthermore, it is of course also possible for the tubular element, the distal flange feet and the proximal flange feet to be assembled from different components into one unit.

According to a further embodiment of the third aspect, the separate flanges, or parts thereof, or the separate flange feet of the separate flanges have an unequal shape and/or length and/or width in relation to one another, and/or angle in relation to the longitudinal axis, and/or fillings (which will be discussed below in the fourth aspect).

According to a further embodiment of the third aspect, the fillings (which will be discussed below in the fourth aspect) of the separate flanges, or the separate flange feet of the separate flanges have, in relation to one another, an unequal shape, and/or length, and/or width, and/or angle in relation to the longitudinal axis, and/or consistency, and/or material properties.

According to a further embodiment of the third aspect, the fillings (which will be discussed below in the fourth aspect) of the separate flange feet extend beyond the circumference of a flange foot, and in a lateral and/or radial direction therefrom.

According to a further embodiment of the third aspect, the fillings (which will be discussed below in the fourth aspect) of the separate flange feet are interconnected in such a way that a continuity arises between all or a number of fillings of the flange feet of one or both flanges.

FOURTH ASPECT

According to a fourth aspect, this application also relates to a new and inventive prosthesis, in particular a 'prosthesis of the so-called type with a tubular element', as described as a vascular prosthesis in WO 00/22339 and as a heart prosthesis in sections 1.1, 2.1, 3.1 and 4.1 of WO 00/44311. WO 00/22339 in its entirety, and WO 00/44311, sections 1.1, 2.1, 3.1 and 4.1, are included by reference in this application for further details of the prosthesis according to the fourth aspect.

The fourth aspect of this application is also very readily applicable in combination with one or more of the other aspects of this application, such as, inter alia, the third and sixth aspect of this application.

Memory material, such as nitinol, has the favourable property that it can be deformed from a first condition to a second condition, and can be fixed in this second condition. By exceeding or understepping a specific threshold temperature, the fixing can be undone, after which a reverse deformation from the second condition to the first condition takes place. However, restrictions apply to this deformation and reverse deformation. If memory metal, such as nitinol, is deformed with an abrupt transition, as in the case of a sharp crease, permanent deformations occur. As a result of these permanent deformations, the final condition remaining after reverse deformation differs from the original first condition. It is even possible that little or no deformation will take place. The memory then functions, so to speak, less well or not at all. To prevent this, it is customary to avoid sharp bends by using a concave shape, at the location of a sharp bend, so to speak in the axil thereof, which makes the bend much more gradual. In the case of 'prostheses of the tubular type defined earlier', a sharp curve is usually required in the axil, which, as a result of the measures to cause the bending to run gradually, results in a concave cavity in the axil. This concave cavity reduces the clamping force required for anchoring to the tissue at the location of the axil. The fourth aspect of this application intends to improve the clamping force between the proximal and distal flange.

This object is achieved according to the fourth aspect by providing a prosthesis for attachment in a passage surrounded by tissue,
wherein the prosthesis comprises a tubular element formed from memory material with a proximal and distal flange which extend around the tubular element;
wherein the distal and proximal flange have a radial position, in which they project from the tubular element in a radially outward direction in order to clamp tissue surrounding the passage between the distal and proximal flange;
wherein the distal flange consists of distal flange feet, which are bendable from the radial position, against a pre-tension created by the memory material, to an extended position, in which the distal flange feet extend in the longitudinal direction of the tubular element and which are fixable in this extended position, in order to return to the radial position under the influence of the pre-tension once the fixing has been undone;
wherein the distal flange feet, at the ends attached to the tubular element, are provided on the side facing the proximal flange with a filling which is designed, in the radial position of the distal and proximal flange, to increase the clamping force with which the distal and proximal flanges clamp the tissue in situ. The inventor has noted that the properties of memory material are not readily capable of providing a firm clamping force in the vicinity of the ends attached to the tubular element, but that this clamping force can be considerably improved by providing a filling in that area which, in the clamped condition, is located between the respective flange feet and the tissue to be clamped.

According to a further embodiment of the fourth aspect, the distal flange feet have a concave-curved part which follows on from the ends of the distal flange feet attached to the tubular element, wherein the hollow side of the concave-curved part faces towards the proximal flange, and wherein the filling is provided in the hollow side of the concave-curved part. The inventor has noted that memory material has particular difficulty in bending over a sharp curve under the influence of the memory effect and as a result clamping force is lost. This can be prevented according to the fourth aspect of this application by providing the concave part with the filling therein.

According to a further design of the fourth aspect with a concave-curved part, the filling protrudes from the cavity formed by the concave part in the direction of the opposite flange feet. The clamping effect and/or sealing at the location of the concave-curved part can thus be increased.

According to a further embodiment of the fourth aspect with a projecting filling, the filling is compressible in such a way that, if the flange feet are in the radial position, the part of the filling protruding from the cavity can be compressed. The clamping effect and sealing can thus be even further improved.

According to a further embodiment of the fourth aspect, the concave-curved part of the distal flange feet, on the side thereof facing towards the free ends of the distal flange feet, viewed in the radial direction and radial position, changes to a straight part. This straight part preceded by a concave-curved part appears to be capable of providing an effective clamping force.

According to a further embodiment of the fourth aspect, the proximal flange can be provided, in a manner corresponding to the distal flange, with proximal flange feet which are bendable from the radial position, against a pre-tension created by the memory material, to an extended position, in which the proximal flange feet extend in the longitudinal direction of the tubular element, and which are fixable in this extended position in order to return to the radial position under the influence of the pre-tension once the fixing has been undone; wherein the proximal flange feet, on the ends attached to the tubular element, on the side facing towards the distal flange, are provided with a filling which is designed, in the radial position of the distal and proximal flange, to increase the clamping force with which the distal and proximal flange clamp the tissue in situ. In a corresponding manner, according to a further design, the proximal flange feet may have a concave-curved part which follows on from the ends of the proximal flange feet attached to the tubular element, wherein the hollow side of the concave-curved part faces towards the distal flange, and wherein the filling is provided in the hollow side of the concave-curved part. Furthermore, in this design, the concave-curved part of the proximal flange feet, on the side thereof facing towards the free ends of the proximal flange feet, viewed in the radial direction and radial position, may also optionally change into a straight part.

In a further design of the fourth aspect, the filling is made from a material other than the material from which the tubular element, the distal flange and the proximal flange are made. The filling may, for example, be made or may comprise the same material as the material from which the tubular element is made. However, the filling may also be made from or may comprise a synthetic foam or textile, such as those generally used in the medical device industry for various applications, for example Dacron, Teflon and various types of polyester.

In a further design of the fourth aspect, the memory material is a memory metal. The memory metal here may be a nitinol alloy.

FIFTH ASPECT

According to a fifth aspect, the application relates to a new and inventive applicator for implanting a hollow prosthesis with an open distal end and an open proximal end. Examples of hollow prostheses of this type include:
- hollow designs of a 'prosthesis of the type with a tubular element' such as the prosthesis described as a vascular prosthesis in WO 00/22339 and as a heart prosthesis in sections 1.1, 2.1, 3.1 and 4.1 of WO 00/44311. In this connection, WO 00/22339 in its entirety and WO 00/44311 sections 1.1, 2.1, 3.1 and 4.1 are included by reference in this application for further details of the prosthesis.
- stents, such as the stent according to the third aspect of this application;
- ring prostheses, such as the ring prosthesis according to the second aspect of this application or a ring prosthesis as known from WO 00/44311 and WO 03/082121 of the inventor, which, in this context, are included by reference in this application for further details of the prosthesis.

Hollow prostheses of this type are normally intended for implantation in a passage through which blood or another fluid flows. The blood or other fluid will then enter and leave the prosthesis at the opposite open ends.

According to the fifth aspect, the object of the present application is to provide an applicator for a hollow, distally and proximally open prosthesis, said applicator being of simple construction and also being simple and reliable in use.

This object is achieved according to the fifth aspect by providing an applicator for the implantation of a hollow prosthesis with an open distal end and an open proximal end, comprising:
- a tube with an inner screw thread over at least a part of the length thereof;
- a pin extending through the tube with, over at least a part of the length thereof, an outer screw thread which mates with the aforementioned inner screw thread;
- wherein the tube carries a sheathing on the distal end thereof;
- wherein the pin is equipped, on the distal end thereof, with a carrier for a prosthesis, said carrier, on the one hand, being rotatable in relation to the pin around the longitudinal centre line of the pin and, on the other hand, being shiftable from a position pushed out from the sheathing in the proximal direction in relation to the sheathing to a position entirely or partially retracted into the sheathing, by rotating the tube in relation to the pin; and
- wherein the applicator further comprises an axial guide which is designed, on the one hand, to prevent rotation of the carrier in relation to the sheathing around the longitudinal centre line of the pin and, on the other hand, to allow axial shifting of the carrier in relation to the sheathing.

The operation of this applicator is very simple and reliable. By merely rotating the pin in relation to the tube, the pin will be able to move in the proximal direction in relation to the tube as a result of the mating inner and outer screw thread. The carrier, which is mounted on the distal end of the pin, is pushed into the sheathing, and the prosthesis provided on the carrier will be held in place by the distal edge of the sheathing. Thus, viewed in relation to the carrier, the prosthesis will be pushed away in the distal direction of the carrier and will be detached. Any hollow, annular or tubular prosthesis can be simply and reliably implanted with this applicator. Furthermore, the structural design of this applicator is simple and robust.

According to a further design of the fifth aspect, the carrier, on the distal end thereof, comprises a nose part tapering in the distal direction with a rounded point. The applicator, or at least the distal end thereof, can easily be fed, with a nose part of this type, through a channel or other passage to the intervention location. When used for the implantation of a ring prosthesis in an atrioventricular valve, this nose part will have the additional advantage that the valve flaps themselves are thereby held back and protected from the prosthesis to be implanted, so that they cannot thereby be damaged.

According to a further design of the fifth aspect, the carrier part has a carrier surface facing radially outwards, the outer contour of which matches the inner contour of the sheathing. The carrier can thus slide inwards into the sheathing essentially without play when the prosthesis is detached. The prosthesis can then no longer slide inwards into the sheathing or be squeezed between the sheathing and the carrier. A reliable and effective detachment of the prosthesis is thus ensured.

According to a further design of the fifth aspect, the tube and the pin are designed to be flexible, such as bendable or kinkable, over at least a part of the length thereof, in such a way that the longitudinal centre line of the tube and pin is flexible, such as bendable or kinkable. The applicator can thus be used in curved access routes. This can be implemented, inter alia, if the tube and the pin, over at least a part of the length thereof, are designed from superelastic material, such as nitinol designed in superelastic form; and/or if the tube and the pin, over at least a part of the length thereof, are designed as a wire, such as steel wire.

The fifth aspect further relates to an assembly, comprising, on the one hand, an applicator according to the fifth aspect and, on the other hand, an aforementioned hollow prosthesis, in particular a heart prosthesis, wherein the prosthesis carried by the carrier is disposed on the carrier. The prosthesis may be clamped in place on the carrier surface. The clamping may be very light so that, on one hand, it is just sufficient to prevent the prosthesis from sliding prematurely off the carrier and, on the other hand, the clamping force does not hinder or barely hinders the detachment. In the fifth aspect, the prosthesis may be one from the group of:
- a ring prosthesis according to the second aspect of this application; and/or
- a stent according to the third aspect of this application; and/or
- a 'prosthesis of the type with a tubular element'.

SIXTH ASPECT

According to a sixth aspect, this application relates to a new and inventive, variable-diameter ring structure with distal and proximal flange feet.

The object of the sixth aspect of this application is to provide a ring structure of this type which is very simple in structure.

This object is achieved according to the sixth aspect by providing a variable-diameter ring structure with distal and proximal flange feet; wherein the ring structure has an axial direction and a radial direction across it; wherein the distal and proximal flange feet have a radial position, in which the free ends of the flange feet point in the radial direction for anchoring with surrounding tissue; wherein the distal flange feet have an extended position, in which the distal flange feet extend in the radial direction; and wherein the distal flange feet, when they are in the extended position, are under a pre-tension, which, when released, bends the distal flange feet from the extended position to the radial position; and wherein the ring structure is constructed from a series of elongated closed loops lying next to one another which, in each case, at the midpoint of the longitudinal sides thereof, are attached laterally to one another via a junction to form this ring structure, in such a way that, on the one hand, the imaginary line through all junctions forms a closed ring and divides each loop into an aforementioned distal flange foot and an aforementioned proximal flange foot and, on the other hand, the ring structure is expandable and/or compressible.

The simplicity is obtained according to the sixth aspect by constructing the ring structure from elongated loops which, arranged with the long direction in the axial direction of the ring structure, are set up alongside one another in an annular series and are connected roughly at the midpoint of the long sides to the respective adjacent elongated loop. The diameter of the ring structure can be varied due to the widths of the loops, said widths being disposed in the circumferential direction of the ring structure. According to the sixth aspect, the simplicity is further obtained by also using the elongated loops as proximal and distal flange feet, one half of the longitudinal loops forming the proximal flange feet and the other half the distal flange feet. In the extended condition, the loops are pre-tensioned in order to be inclined to bend in a radially outward direction. It is noted here that the proximal flange feet can also point permanently in the radial direction, wherein only the distal part of the loops, under pre-tension, will then be able to be in the extended condition.

With regard to the distal and/or proximal flange feet of the ring structure according to the sixth aspect of this application being in the extended condition under pre-tension, it is noted that this pre-tension, as explained at the beginning of this application in relation to active bending, can be implemented, on the one hand, by means of memory materials with memory properties which make it possible to 'freeze' the flange feet in the extended condition and/or, on the other hand, by using conventional resilient materials.

Comparing the compressed and expanded diameter of the ring structure, according to the sixth aspect, viewed in relation to the expanded condition, diameter reductions of more than 50% are achievable, i.e. the compressed diameter may be less than half of the expanded diameter.

According to a further design of the sixth aspect, the distal flange feet are bendable from the radial position to the extended position against a resilience which builds up the aforementioned pre-tension. The surgeon or assistant will then himself extend the flange feet shortly before the intervention and fix them temporarily in the extended position by means of a mechanical obstacle and/or, in the case of a memory material, a temperature treatment.

According to a further design of the sixth aspect, the proximal flange feet also have an extended position wherein the proximal flange feet extend in the axial direction; and the proximal flange feet, when they are in the extended position, are under a pre-tension, which, when released, bends the proximal flange feet from the extended position to the radial position. The entire ring structure can thus be brought into an essentially flat cylindrical condition.

According to a further design of the sixth aspect, the proximal flange feet are bendable from the radial position to the extended position against a resilience which builds up the aforementioned pre-tension. The surgeon or assistant will then himself extend the flange feet shortly before the intervention and fix them temporarily in the extended position by means of a mechanical obstacle and/or, in the case of a memory material, a temperature treatment.

According to a further design of the sixth aspect, the ring structure is made from a memory material. The memory material here may be a memory metal, such as a nitinol alloy.

According to a further design of the sixth aspect, the ring structure is expandable from a first condition to a second condition, and the ring structure, when it is in the first condition, is under a pre-tension, which, when released, causes the ring structure to expand in the direction of the second condition. The ring structure can therefore automatically expand in full or in part. The expansion can nevertheless still be supported by means of an instrument according to the first aspect of the application, or by means of a different instrument, such as a balloon.

According to a further design of the sixth aspect, the ring structure is expandable from a first condition to a second condition, and the ring structure, when it is in the second condition, is under a pre-tension, which, when released, causes the ring structure to contract in the direction of the first condition. The ring structure can therefore automatically contract in full or in part. The ring structure is therefore usable, inter alia, as a constriction ring to constrict a dilated heart valve or to draw the tissue around a heart valve more tightly against the prosthesis in order to prevent leakage outside around the prosthesis.

According to a further design of the sixth aspect, one or more of the junctions is provided with one or more radial bores. This bore can be used to attach a biological or artificial valve prosthesis, stent, or further prosthesis to the ring structure. This can be done, for example, by means of a suture or with the aid of different attachment elements fixable in the bores. This attachment of a further prosthesis can take place prior to or after the implementation of the ring structure in the patient. Thus, for example, a valved stent according to the third aspect of this application can be implemented in combination with the ring structure.

According to a further design of the sixth aspect with bores in junctions, at least 3, such as 4 or 8, junctions lying in a distributed manner over the circumference of the ring structure have one or more aforementioned radial bores. Thus, all junctions may also have one or more aforementioned radial bores.

According to a further design of the sixth aspect, either the distal flange feet, in the radial position, have a bulge facing towards the proximal flange feet; or the proximal flange feet, in the radial position, have a bulge facing towards the distal flange feet. Adaptation to the anatomy of the mitral and tricuspid annulus is thus implemented and a better attachment to the mitral or tricuspid annulus is possible. Here, the bulges may be provided in the halves of the respective flange feet adjacent to the junction.

According to a further design of the sixth aspect, the ring structure comprises a single piece of material. The ring structure may be manufactured, for example, by laser burning or etching from a single piece. This single piece may be a tubular or otherwise plate material, for example made of metal such as stainless steel or a nitinol alloy. If the ring structure is combined with a valved or non-valved stent, it is possible to produce the combination of stent and ring structure from a single piece of material, along with the possibility of producing these two components as separate components and then interconnecting them at any time in a different manner, such as by means of sutures, welds or otherwise. The plate material may be in a flat or curved condition prior to the formation of the ring structure and may be closed to a ring structure following removal of material, but the plate material may also have a tubular configuration prior to the removal of material.

According to further designs of the sixth aspect, the ring structure may be sterile and/or made from one or more medically acceptable materials.

According to a further design of the sixth aspect, one or more of the flange feet comprises one or more pins on the sides facing towards one another. A firmer anchoring in tissue can thus be implemented if required.

According to a further design of the sixth aspect, the ring structure or one or more flanges thereof, or one or more flange feet thereof are totally or partially coated in a sealing manner with tissue, such as pericardium, or materials, such as textile or plastics which can be tolerated by the body, such as Dacron and Teflon, which prevent the passage of blood or other fluids.

According to a further design of the sixth aspect, one or both flanges, or the flange feet of one or both flanges thereof, differ from one another in length and/or in width and/or in shape and/or in angle in relation to the longitudinal axis, or manner of coating and/or filling.

According to a further design of the sixth aspect, the separate flanges, or parts thereof, or the separate flange feet of the separate flanges have an unequal shape and/or length and/or width in relation to one another, and/or angle in relation to the longitudinal axis, and/or fillings.

According to a further design of the sixth aspect, the fillings of the separate flanges, or the separate flange feet of the separate flanges, have an unequal shape and/or length and/or width in relation to one another, and/or angle in relation to the longitudinal axis, and/or consistency and/or material properties.

According to a further design of the sixth aspect, the fillings of the separate flange feet extend beyond the circumference of a flange foot, and/or in a lateral and/or radial direction therefrom.

According to a further design of the sixth aspect, the fillings of the separate flange feet are interconnected in such a way that a continuity arises between all or a number of fillings of the flange feet of one or both flanges.

According to the sixth aspect, the application also relates to an assembly comprising a ring structure according to the sixth aspect along with a heart valve, which may or may not be stented or inserted in a stent, mounted therein. The heart valve may be a natural donor valve, which may or may not be stented or inserted in a stent, such as from an animal or human. In particular, the heart valve may comprise a biological material which is chosen from the group of:
porcine valves; and/or
bovine valves; and/or
equine valves; and/or
human valves; and/or
kangaroo valves.

As explained above in relation to the third aspect, it is also the case in the sixth aspect, as in the other aspects of this application, that none of these biological valves has to be entirely biological, but, in addition to biological material, may also comprise non-biological material such as plastic or metal. Furthermore, these biological valves may or may not be a reconstructed valve. A reconstructed valve is generally understood to be a valve of biological material, from which the original anatomical link has been broken. A reconstructed valve may be formed by combining a plurality of biological components into a valve. The plurality of biological components may originate from the same donor or from different donors. It is even conceivable for the biological components to originate from different types of donor, for example one or more components originating from a pig in combination with one or more components originating from a bovine animal, or one or more components originating from a human in combination with one or more components originating from the same or different types of animal.

SEVENTH ASPECT

According to a seventh aspect, this application also relates to a manipulator for releasing a prosthesis with a plurality of distal and proximal flange feet. Particularly in the case of compressible prostheses, this cannot always be carried out in practice, in particular if the compressed prosthesis first needs to expand and only thereafter must the flange feet be released from a radially pre-tensioned extended position to move to the radial position.

According to the seventh aspect, the object of this application is to provide an alternative manipulator for the release of extended, radially pre-tensioned distal and proximal flange feet.

This object is achieved according to the seventh aspect by providing a manipulator for the release of a prosthesis, wherein the prosthesis has a plurality of distal and proximal flange feet, which:
  have a radial position, in which the free ends of the flange feet point in the radial direction for anchoring with surrounding tissue;
  have an extended position, in which the flange feet extend in the radial direction; and,
  if they are in the extended position, are under a pre-tension, which, when released, bends the distal flange feet from the extended position to the radial position;
wherein the manipulator comprises:
  a plurality of U-shaped obstacle elements with a first leg and a second leg, the free ends of which point in the distal direction;
  an operating element;
  for each obstacle element, a cord, one end of which is attached to the obstacle element and the other end of which is connected to the operating element in such a way that, when the operating element is displaced in the proximal direction, the obstacle elements are retracted in the proximal direction.

With a manipulator of this type, the obstacle elements are each connected separately via a cord to the operating element. The operating element may be designed here in many different ways, for example as a rod, tube, cord or any other element to which cords are attachable. The U-shaped configuration of the obstacle elements makes it possible to slide any obstacle from one edge, the proximal edge, over the extended distal and proximal flange feet and to hold it extended. The obstacle elements can then be removed at a suitable moment when the prosthesis is at the intervention site by retracting them in the proximal direction by means of the cords and the operating element. The prosthesis can be held in its position during this retraction by means of an instrument or carrier to which the prosthesis is attached. It is also possible for the prosthesis to be held in its position during the retraction of the obstacle elements by the tissue between which or to which the prosthesis must be attached. The flange feet can bend to their radial position after the obstacle organs have been removed therefrom. It may be possible here for the obstacle elements, until the retraction thereof, to be held in their position on the flange feet due to the proximal flange feet being inclined, as a result of their pre-tension, to bend within the opening defined between the legs of the U-shape. The proximal flange feet will brace themselves between the legs and will be inclined to hold them in place.

The manipulator according to the second aspect may be used entirely separately from other instruments or tools for implanting a prosthesis. However, the manipulator according to the seventh aspect is also very readily applicable in combination with an instrument/applicator according to the first aspect, in combination with an applicator or other tool for implanting the prosthesis as known from one of the earlier applications of the inventor (the aforementioned WO 00/24339, WO 00/44311, WO 03/003926, WO 03/082121 and WO 2005/092246), such as a sleeve which holds the prosthesis in the compressed condition, or otherwise. If a tool, such as a sleeve (which is also understood to include a tube), holds the prosthesis in the compressed condition, this offers the advantage, in cases where the manipulator according to the seventh aspect is used, that the tool can first be removed to allow the prosthesis to expand and that, for example after the expansion has taken place, the U-shaped obstacle elements are removable in the second instance independently from the tool by retracting them in the proximal direction.

According to a further embodiment of the seventh aspect, in the extended condition of the flange feet, a first length is defined in the manipulator as the axial distance between the free ends of distal and proximal flange feet; the first legs of the obstacle elements have a second length; and the second length is at least 75%, such as 90%, of the first length. The first legs can thus extend sufficiently far from the radial outside of the prosthesis along the flange feet to hold both the proximal and the distal flange feet in the extended condition. If the second length here is greater than the first length, the first legs can entirely cover the proximal and distal flange feet from outside and even extend beyond them. The risk of the flange feet then damaging surrounding tissue can therefore be reduced.

According to a further design of the seventh aspect, the second legs are shorter than the first legs. The second legs lie on the radial inside of the prosthesis. In the extended condition, the flange feet are pre-tensioned in order to be inclined to bend radially outwards. They do not then need to be held in place from the inside. The function of the second leg is primarily to hold the obstacle element on the proximal flange foot, for example in that the proximal flange foot, as already explained above, braces itself between the legs of the U-shaped obstacle.

According to a further design of the seventh aspect, the proximal flange feet have a third length, wherein the second legs have a fourth length; and wherein the fourth length is at most equal to the third length. The second legs, which will lie on the inside of the prosthesis, will not therefore extend beyond the proximal flange feet. Damage from parts provided within the prosthesis, such as donor tissue, valve flaps or other construction parts, is thus avoided. If the fourth length is at least 75% of the third length, bracing of the proximal flange feet between the legs can be very reliably ensured.

According to the seventh aspect, the application also relates to an assembly comprising a manipulator according to the seventh aspect and a prosthesis, wherein the prosthesis has a plurality of distal and proximal flange feet, which:
- have a radial position, in which the free ends of the flange feet point in the radial direction for anchoring with surrounding tissue;
- have an extended position, in which the flange feet extend in the axial direction; and,
- if they are in the extended position, are under a pre-tension, which, when released, bends the distal flange feet from the extended position to the radial position.

According to a further design of the assembly according to the seventh aspect, a heart valve, which may or may not be stented or inserted in a stent, can be mounted in the prosthesis. The heart valve may be a natural donor valve, which may or may not be stented or inserted in a stent, such as from an animal or human. In particular, the heart valve may comprise a biological material which is chosen from the group of:
porcine valves; and/or
bovine valves; and/or
equine valves; and/or
human valves; and/or
kangaroo valves.

As explained above in relation to the third and sixth aspect, it is also the case in the seventh aspect, as in the other aspects of this application, that none of these biological valves has to be entirely biological, but, in addition to biological material, may also comprise non-biological material such as plastic or metal. Furthermore, these biological valves may or may not be a reconstructed valve. A reconstructed valve is generally understood to be a valve of biological material, from which the original anatomical link has been broken. A reconstructed valve may be formed by combining a plurality of biological components into a valve. The plurality of biological components may originate from the same donor or from different donors. It is even conceivable for the biological components to originate from different types of donor, for example one or more components originating from a pig in combination with one or more components originating from a bovine animal, or one or more components originating from a human in combination with one or more components originating from the same or different types of animal.

According to a further design of the assembly according to the seventh aspect, the prosthesis is one from the group of:
a ring prosthesis according to the second aspect; and/or
a stent according to the third aspect; and/or
a ring structure according to the sixth aspect; and/or
a stented valve prosthesis; and/or
a 'prosthesis of the type with a tubular element'.

According to a further design of the assembly according to the seventh aspect, the assembly further comprises a sleeve (which is also understood to mean a tube) with a diameter smaller than the maximum or expanded diameter of the prosthesis.

EIGHTH ASPECT

According to an eighth aspect, this application also relates to a port assembly. A port is a construction which provides a passage through a wall into the body or an organ of the patient. Ports of this type may be of a temporary or permanent or semi-permanent nature. In the case of a permanent or semi-permanent port, the connector provided on the outside of the passage for connection of tools is left behind in or on the patient. The difference between a semi-permanent and a permanent port is essentially that the semi-permanent port does not remain indefinitely in or on the patient.

In the case of a connector for a permanent or semi-permanent port, it is important that a) the connection on the wall with the passage formed or passage still to be formed therein can be easily made and maintained, and b) this connection also forms a reliable seal. A first object of the eighth aspect of this application is to provide a port assembly which meets this requirement.

This first object is achieved according to the eighth aspect by providing a port assembly, comprising:

an annular connector which surrounds a port passage; and
a sealing cap to seal the port passage;
wherein the port passage extends from a first connector end to a second connector end;
wherein the second connector end comprises a crosswise contact surface to lie against a wall of an organ;
wherein, in the crosswise contact surface, at least one adhesive slot, such as two adhesive slots, is provided, which extends around the port passage and which is connectable via a feed channel which opens out into this slot to a source for tissue adhesive; and
wherein, in the crosswise contact surface, at least one ring, such as two rings, of one or more suction mouths is provided, said ring extending around the port passage and being connectable via a suction channel to a suction source to suck the crosswise contact surface firmly against the wall of the organ.

The connector will lie here from the access side against the outer wall of the organ (or the body) of the patient. The at least one ring of suction mouths enables a very reliable and very quickly implementable attachment to the wall of the organ concerned. The suction force exerted via a suction source on the suction mouths sucks the connector firmly against the wall of the organ. The at least one adhesive slot which extends around the port passage enables, on the one hand, a very reliable sealing and, on the other hand, enables a permanent or semi-permanent attachment of the connector to the wall of the organ concerned. Tissue adhesive can be brought from the adhesive source into the adhesive slot, with which the connector can be firmly adhered to the wall of the organ. Due to the fact that the adhesive slot extends around the passage, sealing can be ensured around the entire passage. If the port is not or is no longer used to provide access into the organ concerned, the port can be sealed by means of the sealing cap. The sealing cap can provide a permanent seal and then no longer needs to be removable. However, the sealing cap will, in particular, be removable once more to provide further access into the organ. For this purpose, the connector and sealing cap can be provided with a first mating interlocking mechanism, such as a bayonet connection or screw thread, with which the connector and sealing cap are attachable to one another in a manner which seals the port passage.

According to a further design of the eighth aspect, the first mating interlocking mechanism comprises an inner screw thread provided on the connector and an outer screw thread provided on the sealing cap. Thus, when the port is closed, the port passage located within the connector can also be filled. Thus, when the port is closed, fluid, such as blood, can be prevented from occurring or accumulating therein. It is particularly expedient here if the inner screw thread extends to the crosswise contact surface. Depending on the thickness of the wall of the organ to which the port is attached, it can be expedient here if the sealing cap can be rotated beyond the crosswise contact surface in the connector so that it also fills the passage in the wall of the organ. The purpose of this is to prevent the accumulation of body fluids in this passage. Alternatively, the opening in the body tissue can also be sealed directly and in a manner other than by means of the cap described here. In this case, the remainder of the eighth aspect can be used without a cap, and the connector can be attached only temporarily to a hollow organ, and can also be removed again from the body without being finally attached to the hollow organ. In such a case, the eighth aspect will be able to be temporarily attached to a hollow organ by sucking the connector firmly to the organ and the use of adhesive can be dispensed with.

According to a further design of the eighth aspect, the at least one ring of suction mouths comprises at least one suction slot, such as two suction slots, which extend around the port passage. A firm suction can thus be ensured completely around the port passage.

According to a further design of the eighth aspect, the port assembly further comprises an adhesive source for tissue adhesive and/or a suction source to generate a suction force in the at least one ring of one or more suction mouths.

According to a further design of the eighth aspect, the port assembly further comprises one or more work channels which are connectable in a disconnectable manner to the first connector end. A work channel simplifies the remote implanting of the connector, the remote insertion of instruments and the remote fitting of the cap. The remote working facility allows the operator to work via small incisions and to carry out the entire intervention in a minimally invasive manner. A work channel also makes it possible to create a defined required climate in the port, for example by gassing and/or ventilation and/or irrigation and/or drainage. A climate of this type can serve to protect the patient and/or can serve to prevent body fluids from flowing away excessively during an intervention.

According to a further design of the eighth aspect, the work channel comprises a stiff or stiffened channel part and a flexible channel part which is provided between the connector and the stiff channel part in such a way that the stiff channel part is pivotable in relation to the connector. Stiffness of the work channel is important to enable an instrument to be easily guided through it. The instrument may otherwise be caught up or obstructed as a result of flexibility of the work channel. On the other hand, a stiff work channel following on from the connector is not very practical because this imposes restrictions on the accessibility of the connector for the work channel and because the connector may then come loose during manipulation of the work channel. This is solved by providing a flexible channel part between the stiff part of the work channel and the connector. In particular, this flexible channel part follows on directly from the connector.

In the case of a port, it is important for the work channel to be stiff, for example because an instrument guided through the work channel may otherwise be hindered by the work channel in the movement of the instrument, or because the connector cannot otherwise be remotely navigated and implanted. However, a stiff work channel following on from a connector has the disadvantage that the connector restricts the angle at which work can be carried out by the operator and may inadvertently come loose during manipulation of the work channel. A second object of the eighth aspect of this application is to provide a port assembly which overcomes this problem.

According to a further design of the eighth aspect with a flexible work channel part, the flexible work channel part will be able to have a length of at most 20%, such as at most 10%, of the length of the stiff or stiffened channel part.

According to a further design of the eighth aspect with a flexible work channel part, the length of the flexible channel part may be up to 3 times, such as at most 2 times, the diameter of the port passage, whereas the length of the stiff or stiffened channel part may be more than 10× the diameter of the port passage, such as 20× or more than 30× the diameter of the port passage.

This second object of the eighth aspect is achieved by providing a port assembly, comprising:
- an annular connector which surrounds a port passage, said port passage extending from a first connector end to a second connector end; and
- one or more work channels which are connectable in a disconnectable manner to the first connector end;

wherein the second connector end comprises a crosswise contact surface for placing against a wall of an organ; and wherein at least one of these work channels, such as all of these work channels, comprises a stiff or stiffened channel part and a flexible channel part which is provided between the connector and the stiff channel part in such a way that the stiff channel part is pivotable in relation to the connector.

According to a further design of the eighth aspect with a flexible work channel part, the flexible work channel part will be able to have a length of at most 20%, such as at most 10%, of the length of the stiff or stiffened channel part.

According to a further design of the eighth aspect with a flexible work channel part, the length of the flexible channel part may be up to 3 times, such as at most 2 times, the diameter of the port passage, whereas the length of the stiff or stiffened channel part may be more than 10× the diameter of the port passage, such as 20× or more than 30× the diameter of the port passage.

According to a further design of the eighth aspect:
the assembly further comprises a sealing cap to seal the port passage; and/or
the connector and the work channel are provided with a second mating interlocking mechanism, such as a bayonet connection or a screw thread, with which the connector and the work channel are attachable to one another in a sealing manner; and the second mating interlocking mechanism here may comprise an outer screw thread provided on the connector and an inner screw thread provided on the sealing cap.

According to a further design of the eighth aspect, the end of the work channel facing away from the connector is provided with a seal which is designed, on the one hand, to seal the access to the passage surrounded by the work channel and, on the other hand, to allow through an instrument which is to be inserted inwards into the work channel, while maintaining the seal. A seal of this type may, for example, comprise a vascular prosthesis or comparable element. A vascular prosthesis can simply be squeezed tight with the hand, a clamp or wire, elastic or otherwise.

According to a further design of the eighth aspect, the work channel is provided with at least one connection, such as two, three or four connections, for gassing and/or degassing and/or irrigation and/or drainage of the passage surrounded by the work channel; and/or the work channel is provided with one or more valves in order to counteract blood loss on the one hand and, on the other hand, to prevent air from entering.

According to a further design of the eighth aspect, the connector is produced from soluble, so-called 'bioabsorbable' or 'biodegradable' materials, so that the connector can wholly or partially dissolve through time.

According to a further design of the eighth aspect, the cap is coated on the crosswise side with antithrombotic materials or chemical components to prevent blood clotting in situ, or is covered with a piece of vascular prosthesis, or human or animal pericardium, or other material to promote the growth of endothelial tissue in situ.

According to a further design of the eighth aspect, the connector is provided with one or more contact and/or pressure sensors on the crosswise edge to determine whether there is sufficient tissue contact between the crosswise edge of the connector and the tissue where this is located.

NINTH ASPECT

According to a ninth aspect, this application relates to a method for implanting a valve prosthesis in a passage through which blood flows, and also a valve prosthesis which is particularly suitable for this purpose. This method and this assembly are involved in several places in this application in relation to embodiments of aspects discussed therein. The method according to the ninth aspect comprises the following steps:
- the insertion into the passage and attachment to surrounding tissue of a ring prosthesis which, under pre-tension, is held in a first diameter, wherein the pre-tension tends to constrict the ring prosthesis to a smaller, second diameter;
- the insertion into the passage of the valve prosthesis;
- the release of the pre-tensioned ring prosthesis in such a way that, under the influence of the pre-tension, it draws the tissue surrounding the passage against the valve prosthesis.

The valve prosthesis is in particular a heart valve prosthesis, and comprises:
- at least a first radial flange provided with radial slots;
- pins which project through the slots in a radial direction;
- a tensioning mechanism designed to be able to pre-tension the pins in order to move through the slots in a radially inward direction; and
- a heart valve.

Further designs of the ninth aspect of the application are set out in the claims associated with the ninth aspect, and also at various places in relation to other aspects of this application. As far as the method and valve prosthesis according to the ninth aspect are concerned, these explanations of the ninth aspect in the other aspects of this application must be interpreted more broadly than as if only restricted to the design of the relevant other aspect discussed therein.

It is noted that each aspect in this application is one invention or comprises a plurality of inventions.

BRIEF DESCRIPTION OF THE DRAWINGS

The present invention will be explained below with reference to embodiments shown schematically in the drawings. In the drawings:

FIG. 1 shows a schematic, perspective view of a medical instrument, in a use as an applicator, according to the first aspect; wherein

FIG. 2 shows schematic longitudinal perspectives of the medical instrument according to FIG. 1, wherein

FIG. 3 shows a schematic, longitudinal section view of a second embodiment of a medical instrument, used as an applicator, according to the first aspect; wherein

FIG. 5 shows a schematic, longitudinal section view of a fourth embodiment of a medical instrument according to the first aspect, in this case used as an applicator for a stent, which may also be a valved stent; wherein FIG. 5a shows a condition in which the manipulator holds a compressed stent in place; FIG. 5b shows a condition in which the manipulator holds an expanded stent in place, and FIG. 5c shows a condition in which the manipulator has released the expanded stent;

FIG. 6 shows a schematic, longitudinal section view of a fifth embodiment of a medical instrument according to the first aspect, in this case used as an applicator for a stent, which may also be a valved stent; wherein

FIG. 7 shows a schematic, longitudinal section view of a sixth embodiment of a medical instrument according to the first aspect, in this case used as an applicator for a stent, which may also be a valved stent; wherein FIG. 7a shows a condition in which the manipulator holds the compressed stent in place; FIG. 7b shows a condition in which the manipulator holds the expanded stent in place; FIG. 7c shows a condition in which the manipulator has released the expanded stent;

FIG. 8 shows a schematic longitudinal section view of a seventh embodiment of a medical instrument according to the first aspect, wherein the medical instrument is used as an applicator for a ring prosthesis according to the second aspect; wherein FIG. 8c shows a condition in which the ring prosthesis is attached to tissue and the instrument retracted;

FIG. 9 shows a schematic view of a first design of a ring prosthesis according to the second aspect, as also shown in FIG. 8; wherein

FIG. 10 shows a schematic longitudinal section view of an eighth embodiment of a medical instrument according to the first aspect, wherein the medical instrument is used as an applicator for a ring prosthesis according to the second aspect; wherein FIG. 10a shows a condition in which the manipulator carries the ring prosthesis while the latter has a large diameter, and FIG. 10b shows a condition in which the manipulator carries the ring prosthesis while the latter has a smaller diameter;

FIG. 11 shows a schematic view of a second design of a ring prosthesis according to the second aspect, as also shown in FIG. 10; wherein FIG. 11a is a perspective view and FIG. 11b is a side view;

FIG. 12 shows, in perspective side view, a third design of a ring prosthesis according to the second aspect; wherein

FIG. 13 shows a very simply designed applicator according to a fifth aspect with a ring prosthesis according to the second aspect loaded thereon; here.

FIG. 14 shows a schematic longitudinal section of a ninth design of a medical instrument according to the first aspect; wherein FIG. 14a shows a condition with the fingers at the minimum span, and FIG. 14b shows a condition with the fingers at the maximum span;

FIG. 15 shows a schematic longitudinal section of a first design of a prosthesis according to the fourth aspect of this application; wherein FIG. 15 is a modified version of FIG. 10a from WO 00/24339 of the inventor;

FIG. 16 shows a schematic longitudinal section of a second design of a prosthesis according to the fourth aspect of this application; wherein FIG. 16a shows the condition with extended proximal and distal flange feet, and FIG. 16b shows the condition wherein the proximal and distal flange feet are in the radial position; and wherein FIGS. 16a and 16b are a modified version of FIGS. 2a and 2b from WO 00/44311 of the inventor;

FIG. 21 shows details of the obstacle element of the manipulator according to FIG. 20, wherein

FIG. 24 shows, very schematically, an assembly and method according to the ninth aspect, wherein

DETAILED DESCRIPTION OF THE PREFERRED EMBODIMENTS

FIGS. 1-2 show a first embodiment 100 of a medical instrument according to the first aspect. The medical instrument is used here as an applicator 100 for implanting a prosthesis, in particular a heart prosthesis. This prosthesis is of a type as described in earlier PCT applications of the inventor, i.e. WO 00/24339, WO 00/44311, WO 03/003926, WO 03/082121 and WO 2005/092246.

Figure 2A:
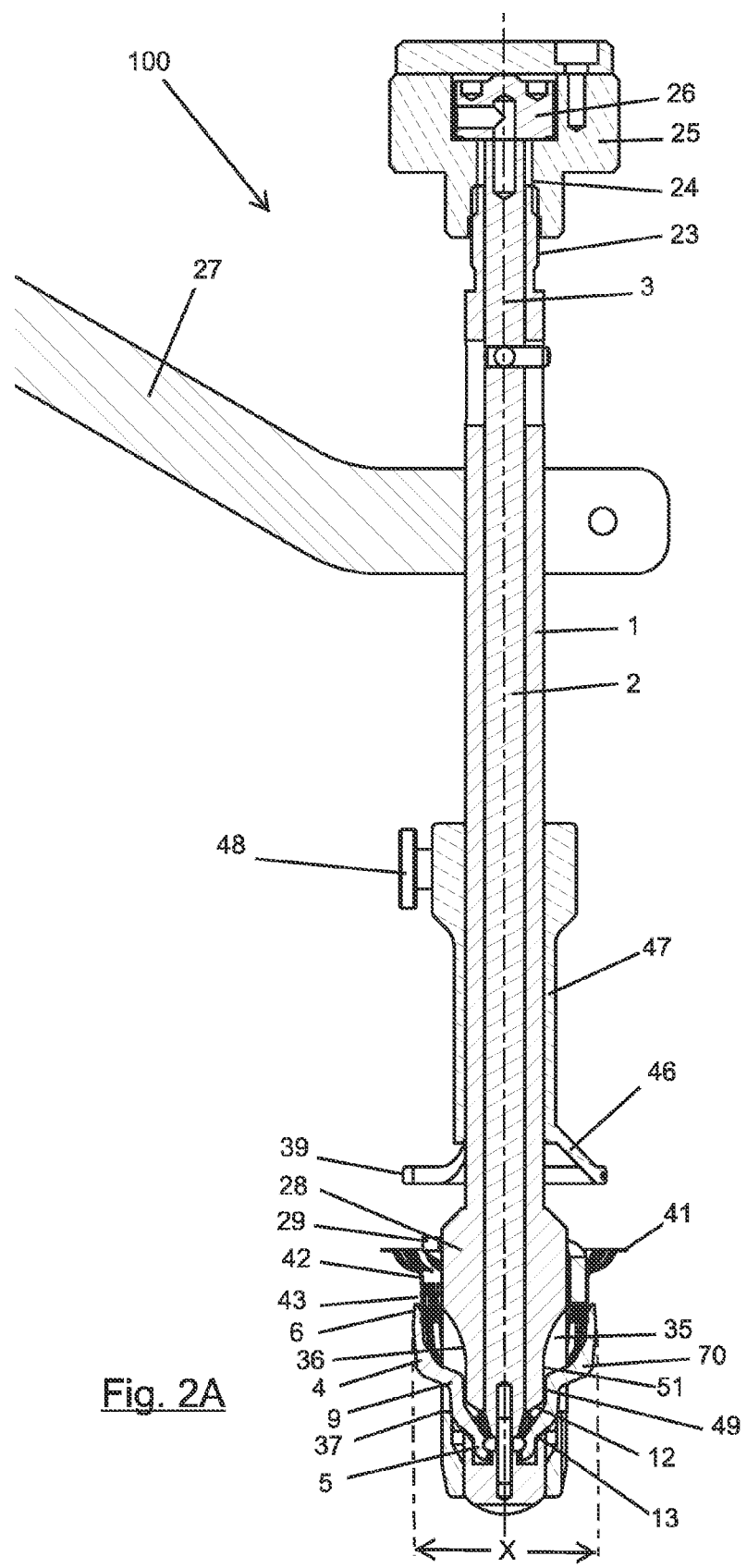
FIG. 2a shows a condition in which the manipulator holds the prosthesis in place and FIG. 2b shows a condition in which the manipulator has released the prosthesis.

The applicator 100 comprises a first rod 1 in the form of a tube, a second rod 2, as shown in FIG. 2, which extends along and parallel to the tube 1, in this case the second rod 2 being pushed through the tube 1, a longitudinal centre line 3 and also a manipulator 140. The longitudinal centre line 3 is defined here by the direction in which the tube 1 and the second rod 2 extend. The second rod 2 can be shifted in relation to the tube 1 by shifting the rod 2 in the extension direction of the longitudinal centre line 3 in relation to the tube 1. In order to limit this longitudinal shift, the tube 1 is provided with longitudinal slots 21, and a pin 22 which projects into the longitudinal slot 21 is provided on the second rod. In order to be able to move the second rod 2 in relation to the tube 1, an operating button 25 is provided on the proximal end of the applicator. As shown in particular in FIG. 2A, this operating button 25 is provided with an inner screw thread 24 which interworks with an outer screw thread 23 provided on the proximal end of the tube 1. On the proximal end of the second rod 2, a carrier 26 is provided which is widened in relation to the second rod and is confined in the operating button 25 in such a way that the operating button 25 is freely rotatable in relation to the carrier 26, which in turn is again fixed in relation to the second rod 2. Through rotation of the operating button 25, depending on the direction of rotation, the second rod 2 is displaced in relation to the tube 1 in the distal direction ID or proximal direction P. As the pin 22 in the longitudinal slot 21 prevents rotation of the second rod 2 in relation to the tube 1, the movement of the tube 1 in relation to the second rod 2 will be a pure translation movement here.

Figure 1A:
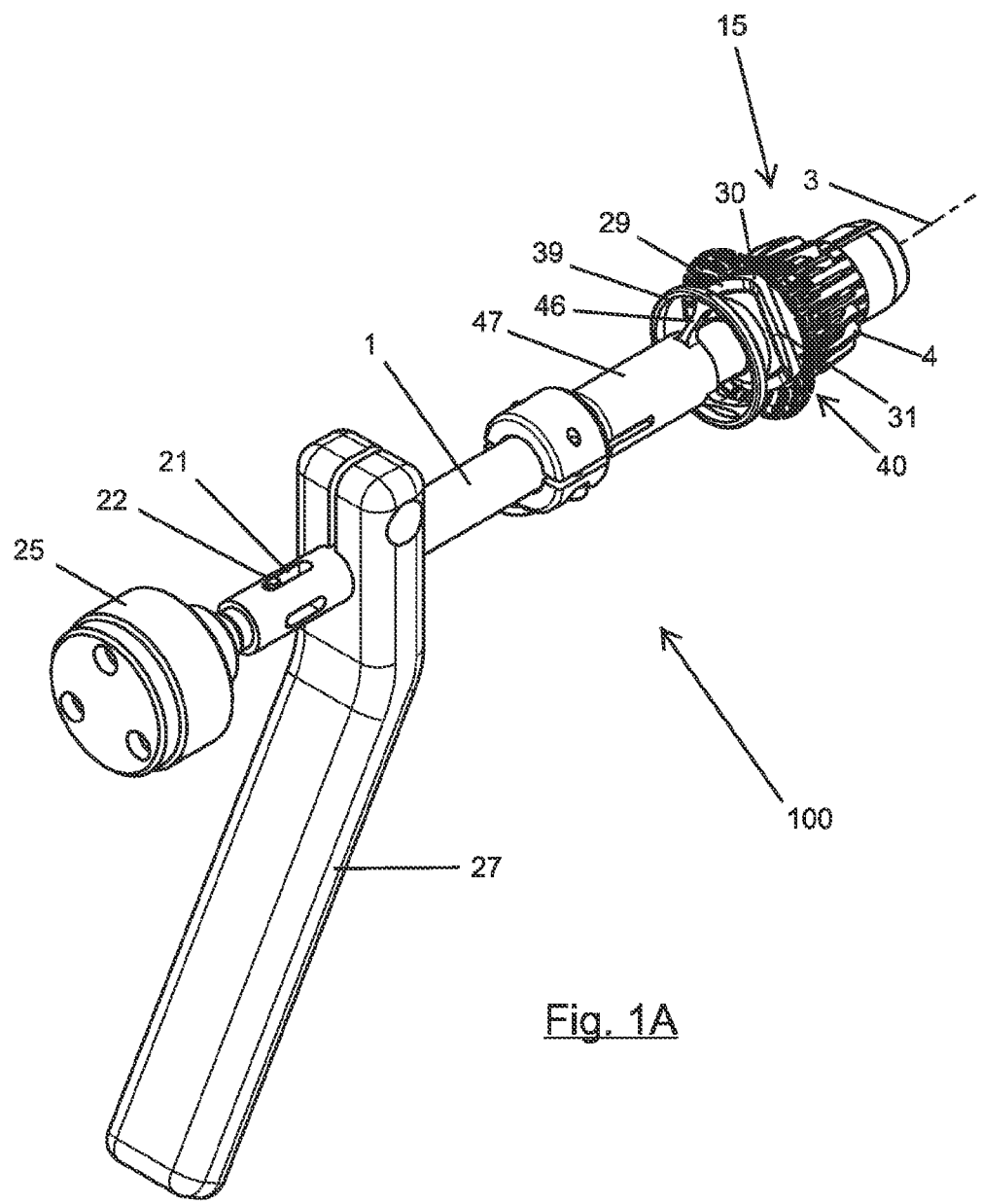
FIG. 1a shows a condition in which the manipulator holds the prosthesis in place.
Figure 1B:
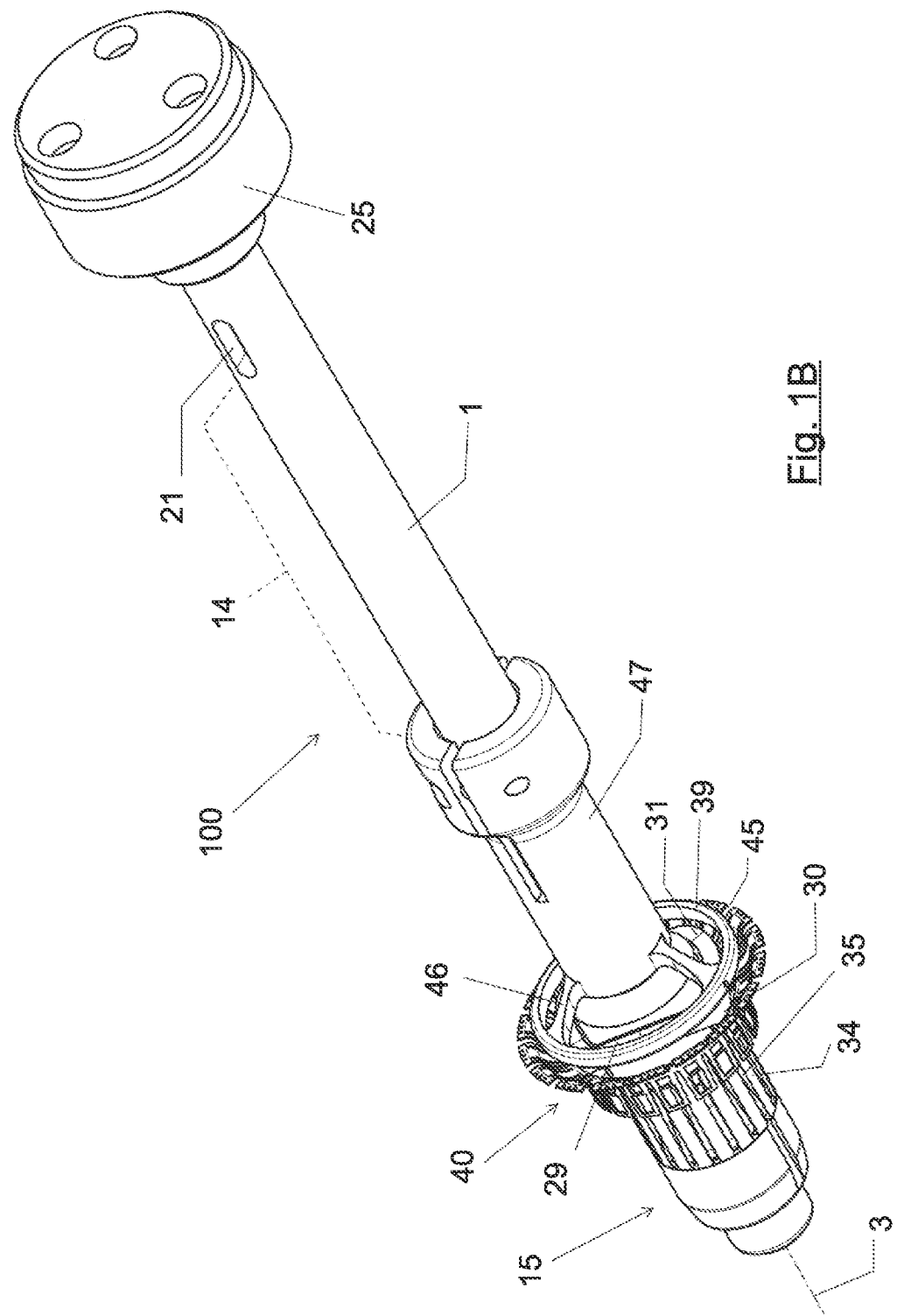
FIG. 1b shows a condition in which the manipulator has released the prosthesis.

In order to enable the operator to handle the medical instrument in a simple manner, the instrument is provided with a handgrip 27 (not shown in FIG. 1*b*).

It will be clear that the part 14 of the applicator (see FIG. 1B) may be longer or shorter, as required for the application. Furthermore, it is noted that the applicator, viewed in relation to the longitudinal centre line 3, does not have to be rigid. Discussed in terms of the longitudinal centre line 3, the applicator may be designed to be bendable and/or kinkable and/or flexible, so that it is also usable if the access route to the intended location for the distal end 15 of the applicator runs along a non-straight route. In particular, the aforementioned part 14 of the applicator will be able to be designed to be bendable and/or kinkable and/or flexible for this purpose. It will furthermore be clear that the comments made in this paragraph are applicable to all designs of the first aspect of this application. The flexible and/or bendable and/or kinkable characteristic of the applicator can be implemented by designing the aforementioned part 14, i.e. the rods running there, in nitinol in superelastic form or in wires, such as steel wires.

Figure 2B:
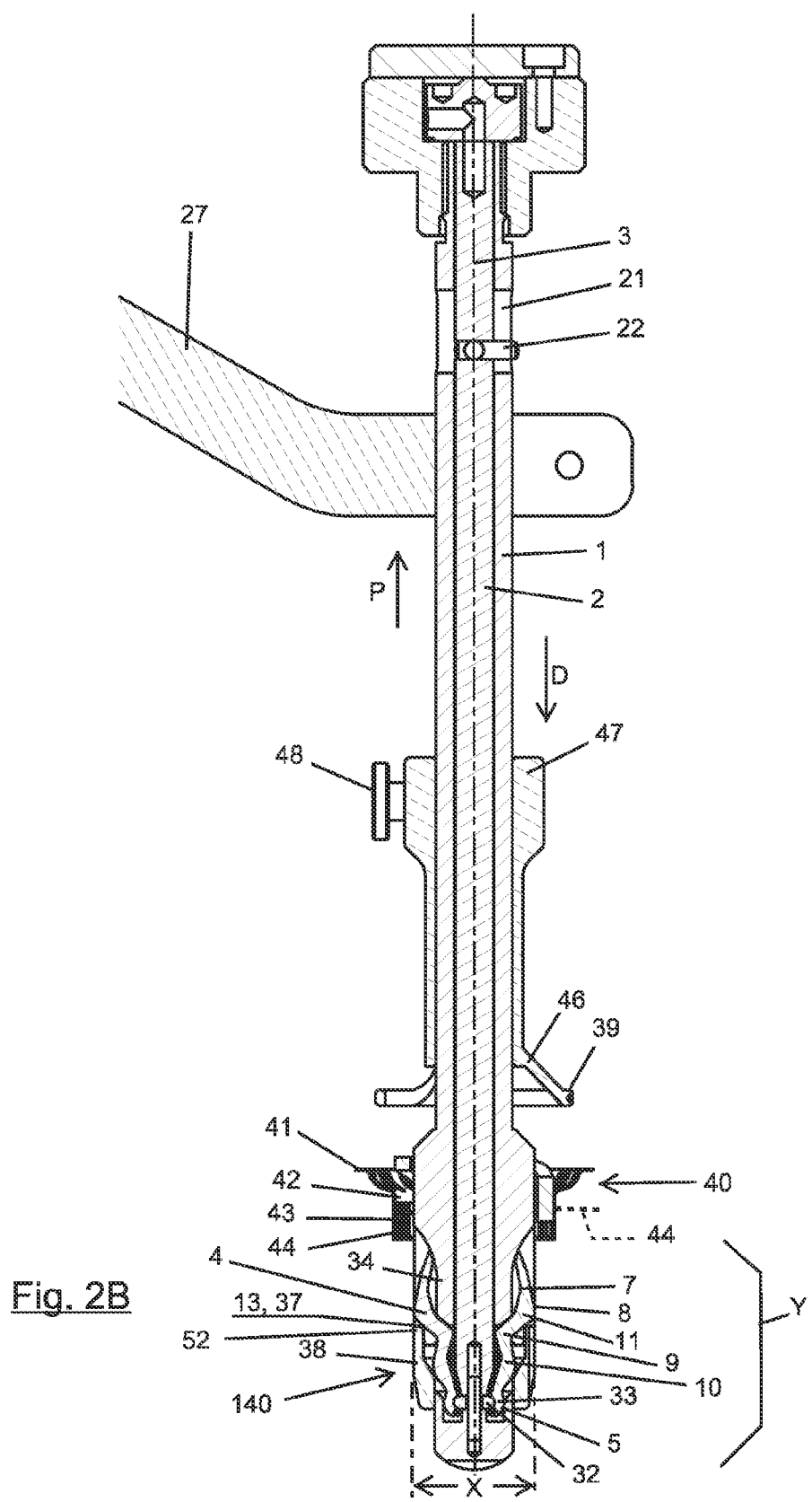

The applicator shown in FIGS. 1 and 2 is furthermore provided on the distal end with a 'prosthesis 40 of the type with a tubular element'. This prosthesis 40 comprises a proximal flange 41, a tubular element 42 and a distal flange 43. The distal flange 43 is constructed from flange feet 44 which move from the axial, extended position shown in FIGS. 1*a*, 1*b* and 2*a* to the radial position indicated in FIG. 2*b* by broken lines (on the right-hand side). Thus, the proximal and distal flange can clamp tissue, such as the annulus tissue of a heart valve, in order to fix themselves in a bloodstream passage. This is known per se from the previously repeatedly mentioned earlier PCT applications of the inventor. In the embodiment shown in FIGS. 1 and 2, the proximal flange 41 is a fixed flange which extends continuously in the radial direction from the tubular element 42. In this case, the proximal flange 41 is furthermore designed as interrupted with interruptions 45 located at—in this case regular—intermediate intervals. However, it is noted that the proximal flange 41 may also be designed as uninterrupted and/or movable, in the same way as the distal flange 43.

The applicator 100 is provided with a carrier part 28 to carry the prosthesis 40. As an intermediate piece between the carrier part 28 and the prosthesis 40, a waved ring 29 is provided, with four wave peaks 31 and four wave troughs 30 (as shown in particular in FIG. 1). This waved ring carries the prosthesis 40 with the wave troughs, so that the prosthesis 40 is essentially carried at four points. This simplifies the detachment of the prosthesis after it has been attached to surrounding tissue. If the prosthesis 40 serves to attach a new artificial heart valve or donor heart valve, it is possible in principle to choose to attach the new artificial heart valve or donor heart valve in advance in the ring prosthesis. The heart valve is then loaded onto the applicator together with the prosthesis 40. Following detachment and attachment to tissue of the prosthesis 40, no further assembly action needs to be carried out for the attachment of a heart valve. However, it is also very readily possible first to attach the prosthesis 40 to surrounding tissue and only thereafter to implant the new artificial heart valve or donor heart valve and attach it to the prosthesis 40. If the prosthesis 40 is first attached to the tissue and the valve is implanted thereafter, it is conceivable that the applicator 100 is first removed from the patient and that the same or a different applicator provided with the valve is thereafter delivered to the intervention location in order to implant the valve. It is also conceivable first to implant the prosthesis 40 with a single applicator and then, without first retracting the applicator from the patient, to insert the valve into the already implanted prosthesis.

The manipulator 140 of the applicator 100 comprises a first plurality of fingers 4, each with a first finger end 5 and a second finger end 6. The second finger end 6 is a free end and the first finger ends 5 are supported on the second rod 2. In the case of FIGS. 1 and 2, the support of the first finger ends 5 takes place on the second rod 2 via a pivot attachment in such a way that the fingers 4 are pivotable in relation to the rod 2. In this case, the pivot attachment is designed as a hinge with a convex hinge part 32 attached to the second rod 2 and a concave hinge part 33 provided at the first finger end 5 to accommodate the convex hinge part 32. It is noted that the pivotable attachment may also be designed in a different manner, for example by means of a fork hinge, i.e. a forked part, of which the fork forms the pivot centre line, is formed on the first finger ends, but the pivot attachment may also be designed in a different manner known per se to the person skilled in the art; or by means of a ring which is pushed through passages in the fingers, wherein the fingers are, as it were, threaded onto the ring and the ring acts as a hinge axis for the fingers.

In the condition shown in FIGS. 1*a* and 2*a*, the free finger ends 6 overlap the distal flange feet 44 extended in the axial direction. The term 'overlap' is understood in this application to mean that, viewed in the radial direction perpendicular to the longitudinal centre line 3 of the medical instrument, there is an overlap between the free finger ends 6 of the relevant fingers and the prosthesis, in this case the flange feet 44 thereof. In this overlapping condition, the fingers 4 prevent the distal flange feet 44 from being able to move from the axially extended position to the radial position, indicated schematically in FIG. 2*b* with a broken line. As will be clear, it is practical here if the fingers 4 in the overlapping position are prevented from pivoting radially outwards. This can be implemented as such in many different ways. Thus, for example, a spring or other tensioning element can be disposed around the fingers 4. However, it is also very readily possible to confine the fingers 4 by means of a guide in the position shown in FIG. 2*a*, as will be further explained below.

The condition shown in FIG. 1*a* and FIG. 2*a* is also the condition in which the prosthesis is delivered by means of the applicator to its intended position in the organ or otherwise in the patient, referred to as the intervention location. During this delivery to the intervention location, the fingers in the overlapping position then ensure that the distal flange feet remain in the axially extended condition.

During this delivery of the prosthesis to the intervention location, the applicator will be fed in the distal direction through a channel of tissue, such as a blood vessel. The free second finger ends 6 will protect the distal flange feet 44, which are overlapped by these free second finger ends 6, from the channel wall and hold them in the extended axial position.

After the prosthesis has arrived at its intended location and has been correctly positioned there, the tube 1 will be held immovably in relation to the intended location and the second rod 2 will be displaced in the distal direction D in relation to the tube 1 through operation of the rotary button 25. The fingers 4 attached via a pivot attachment to the second rod 2 will be displaced in the distal direction D in relation to the prosthesis 40. The free second finger ends 6 come free from the axially extended distal flange feet 44. The distal flange feet 44 can then bend actively or passively to the radial position. With reference to FIG. 2A, it is clear that, if the fingers 4 are shifted in the distal direction D in relation to the tube 1, the fingers are then initially shifted purely distally as long as the fingers 4 are supported on the flat part of the guide 51 which runs parallel to the longitudinal centre line 3. As soon as the fingers 4 arrive with their curved part 9 at the oblique part 12 of the guide, a combined movement will take place, comprising a translation of the fingers in the distal direction and a rotation around the pivot point 32.

As is evident, in particular in FIG. 2b, the free second finger ends 6 pivot, during the displacement in the distal direction of the rod 2, in the radially inward direction towards the longitudinal centre line 3 of the applicator 100. The free ends 6 of the fingers 4 therefore move here from a first position (shown in FIGS. 1a and 2a) to a second position (shown in FIGS. 1b and 2b), wherein the distance from the free ends 6 of the fingers 4 to the longitudinal centre line 3 is shorter than in the first position. In the second position, also referred to as the release position, the fingers 4 therefore lie closer against the longitudinal centre line 3. The span X of the applicator 100 is therefore reduced, at least at the location of the fingers 4. The term 'span' is understood here to mean the space that the medical instrument occupies at the location of the fingers in a direction across the longitudinal centre line 3. In the embodiment shown in FIG. 2, the span X in the release position according to FIG. 2b is around 62% of the span X in FIG. 2a in the overlapping position. Thus, the distal part of the applicator 100 indicated as Y in FIG. 2b, i.e. the part which is located distally in relation to the prosthesis, can easily pass, in the release position, in the proximal direction P through the inside of the prosthesis 40, to remove the tube 1, the second rod 2 and the manipulator 140 from the patient, leaving behind the prosthesis.

As clearly shown in FIGS. 1 and 2, the applicator 100, according to a further design, is provided distally from the carrier part 28 with a slotted element 34, which, in the embodiment shown, is designed as a unit integrated with the carrier part 28. However, it will be clear that the slotted element can also be a component provided separately on the tube 1. Each finger 4 extends through a slot 35 of the slotted element 34. In the overlapping position, shown in FIGS. 1a and 2a, the fingers 4 project from the slots 35. In the release position, shown in FIGS. 1b and 2b, the fingers 4 are entirely sunk into the slots 35 in order to be protected from the environment by the slotted element 34. When the applicator is retracted after the prosthesis has been delivered, the fingers 4 cannot therefore damage any tissue, including any heart valve tissue, along which they pass. The fingers are at any rate protected from that tissue by the slotted element 34.

As shown particularly in FIG. 2, the slots 35 have slot bases 36. The slot bases 36 extend along a curve to the carrier part 28, viewed from the distal end to the proximal end of the instrument, to end beyond the lower ends of the distal flange feet 44. It is therefore possible, after the distal flange feet 44 have been released by the fingers 4, to further use the fingers to press therewith from the inside out against the distal flange feet 44 in order to bend them to their radial position. The same can furthermore also be achieved by deepening the slot bases 36 so that, in the overlapping position, a slit (at 49 in FIG. 2a) is located between the slot base 36 and the respective fingers 4. These slits ensure that the fingers 4, as soon as they come free, from the overlapping position, from the distal flange feet 44, as it were, spring inwards in the radial direction. If the fingers are then moved once more in the proximal direction in relation to the tube 1, they will be able to press against the inside of the distal flange feet 44 to help the latter in the pivoting thereof in the radial direction. If the distal flange feet 44 cannot bend automatically, for example under the influence of a pretension, from an axial to a radial position, it may be possible that the fingers 4 entirely ensure this bending of the flange feet from the axial to the radial position. The fingers 4 can therefore bend the distal flange feet actively to the radial position without a passive or otherwise prior bending being required.

According to a further embodiment of the applicator shown in FIGS. 1-2, an annular outer guide 37 is optionally provided. This guide is located distally from the carrier part 28 and also distally from the slotted element 34. The annular outer guide 37 is attached to the tube 1 and is preferably fixed in relation to the tube 1. The axial centre line of the annular outer guide 37 is, in particular, parallel to the longitudinal centre line 3 and, in the embodiment shown, coincides with the longitudinal centre line 3 of the medical instrument. As shown in FIG. 2, the fingers 4 project in the axial direction through the annular outer guide 37. The first finger ends 5 lie here distally from the annular outer guide 37 and the free, second finger ends 6 lie here proximally from the annular outer guide 37. The distance from the first finger ends 5 to the longitudinal centre line 3 is less than the radius of the annular outer guide 37. The free, second finger ends 6 lie, in the overlapping position, at a distance from the axial centre line of the annular guide 37 which is greater than the radius of the annular guide in order to lie, in the release position, at a distance from the axial centre line of the annular guide 37 which is smaller than the radius of the annular guide. The annular outer guide 37 guides the fingers, during the displacement of the rod from the overlapping position to the release position, in a radially inward direction towards the longitudinal centre line 3 of the applicator.

In the embodiment shown, although this may also be different, the annular outer guide 37 is formed by the proximal edge of a sleeve 38. This sleeve protects fingers 4 retracted therein from the environment.

According to a further embodiment, a support ring 39, which is attached by means of carrier arms 46 on an adjustment part 47, may optionally be provided. The adjustment part 47 is adjustable along the tube 1 and is fixable, for example by means of a screw 48, to the tube 1 in a required position. In the condition shown in FIGS. 1-2, the support ring 39 lies at a distance from the prosthesis. The purpose of this is to maintain greater clarity in the illustrations shown in FIGS. 1 and 2. However, if the support ring 39 is used, it will normally lie from the proximal side against the prosthesis 40. The support ring therefore supports the prosthesis from the proximal side if a force acting in the proximal direction is exerted on the prosthesis. This may be the case, for example, if the prosthesis has to be pushed with force through a constriction, or if the distal flange feet 44, in the radial position, are pushed with force in the proximal direction. In order, on the one hand, to provide a clearer view and, on the other hand, also to provide space, for example, for stented parts of a biological tissue or, for example, for artificial or biological valve flaps, the support ring 39 is designed to be open and is attached by means of carrier arms 46 to the adjustment part 47.

According to a further embodiment, the medical instrument, in the case of FIGS. 1 and 2, comprises an applicator, optionally an inner guide 51 and an outer guide 52, both of said guides being carried by the first rod, in this case the tube 1. Here, the fingers 4 each have a first curved zone 9. The fingers 4 define an inner longitudinal side 7 here facing towards the longitudinal centre line 3 and an outer longitudinal side 8 facing away from the longitudinal centre line 3. The inner guide 51 is provided between the longitudinal centre line 3 and the inner longitudinal side 7 of the fingers. The fingers 4 are furthermore provided between the outer guide 52 and the longitudinal centre line 3. The aforementioned first curved zone 9 of each finger defines a first finger part 10, which extends from the first finger end 5, which is pivotably attached to the second rod 2, to the first curved zone 9. A second finger part 11 is defined as the part which extends from the first curved zone 9 to the free end 6 of the finger. Viewed from the first finger ends 5 to the free second finger ends 6, the fingers 4 bend in the first curved zone 9 away from the longitudinal centre line 3. The outer guide 52, which here is essentially nothing other than the aforementioned annular outer guide 37, is provided in such a way that, in the second position, it grips on the outer longitudinal side 8 of the second part of the fingers. It is thus ensured that the fingers 4 are held together in the second position and cannot pivot outwards in an uncontrolled manner. The fingers can also be prevented from pivoting outwards in an uncontrolled manner in a different way, rather than by the outer guide, such as by the annular confining edge 13.

According to a further, optional embodiment, the medical instrument is configured in such a way that, in the first position, the inner guide 51 grips on the inner longitudinal side 7 of the first finger part 10. It is thus achieved that the fingers are held outwards in the first position, and cannot inadvertently pivot inwards.

According to a further, optional embodiment, in the case of the medical instrument 100, the outer guide 52 grips, in the first position, on the outer longitudinal side 8 of the first finger part 10 of the fingers 4. It is thus achieved that the fingers 4 are prevented from further outward pivoting in the first position. If the fingers 4 hold a prosthesis in place, this means that the prosthesis is prevented from being able to be inadvertently released as a result of the fingers 4 pivoting outwards. If, in the first position, the inner guide 51 similarly grips on the inner longitudinal side 7 of the first finger part 10 of the fingers 4, the fingers then lie entirely fixed in position in the first position. They cannot then pivot either inwards or outwards. In general here, in the first position, the outer longitudinal side 8 of the second finger part 11 of the fingers 4 will lie free from the outer guide.

As shown in FIG. 2b, in the second position, the inner guide 51 can optionally grip on the inner longitudinal side 7 of the first finger part 10 and/or second finger part 11 of the fingers 4. The fingers are therefore prevented, in the second position, from being able to pivot further radially inwards. If the fingers are further prevented here by the outer guide from pivoting outwards, the fingers lie entirely confined in the second position, so that they are immovable in the second position. The fingers are thus prevented, in the second position of the medical instrument, from being able to come loose, which is undesirable as this may cause damage to the patient. It will be clear that, if the inner guide 51 grips on the inner longitudinal side of the one of the first finger part 10 or the second finger part 11, the other of the first 10 or second 11 finger part of the fingers 4 can lie free from the inner guide 51.

According to a further design, the first curved zone 9 optionally shows a curve of at least 30°, in particular a curve of at least 45°, such as a curve of 50° or more. As shown in FIG. 2a, the curve in the first curved zone 9 is even more than 70°. The greater this curve, the more the range X of the fingers will increase in relation to the length of the fingers, viewed in the direction of the longitudinal centre line 3. Here, the first finger part 10 can then run relatively close along the longitudinal centre line 3, whereas the second finger part 11, in particular the free finger ends 6, lie significantly further away from the longitudinal centre line.

According to a further embodiment, the fingers optionally show a kinked shape in the first curved zone 9, at least on the inner longitudinal side 7 of the fingers 4. A kinked shape of this type, in particular in combination with a locally substantial bearing away of the inner guide 51 in the direction of the longitudinal centre line 3, makes it possible that the fingers, from a specific time when there is little or no further shifting of the rods in relation to one another in the longitudinal direction of the longitudinal centre line 3, may quickly vary in span X.

According to a further embodiment, the inner guide 51 and the outer guide 52 are optionally immovable in relation to one another. In the case of the applicator 100 according to FIGS. 1 and 2, the inner guide 51 and the outer guide 52 are immovable in relation to one another.

It is noted that the previously discussed slot bases 36 form the proximal part of the inner guide 51. The distal part of the inner guide then extends even further here within the area protected by the sleeve 38.

The outer guide 52 has, in particular, a diameter smaller than the inner diameter of the prosthesis 40. It is thus ensured that, following the detachment and possible complete attachment and implantation of the prosthesis 40, the applicator 100, or at least the distal end part Y thereof, can be retracted in the proximal direction through the prosthesis.

Figure 3A:
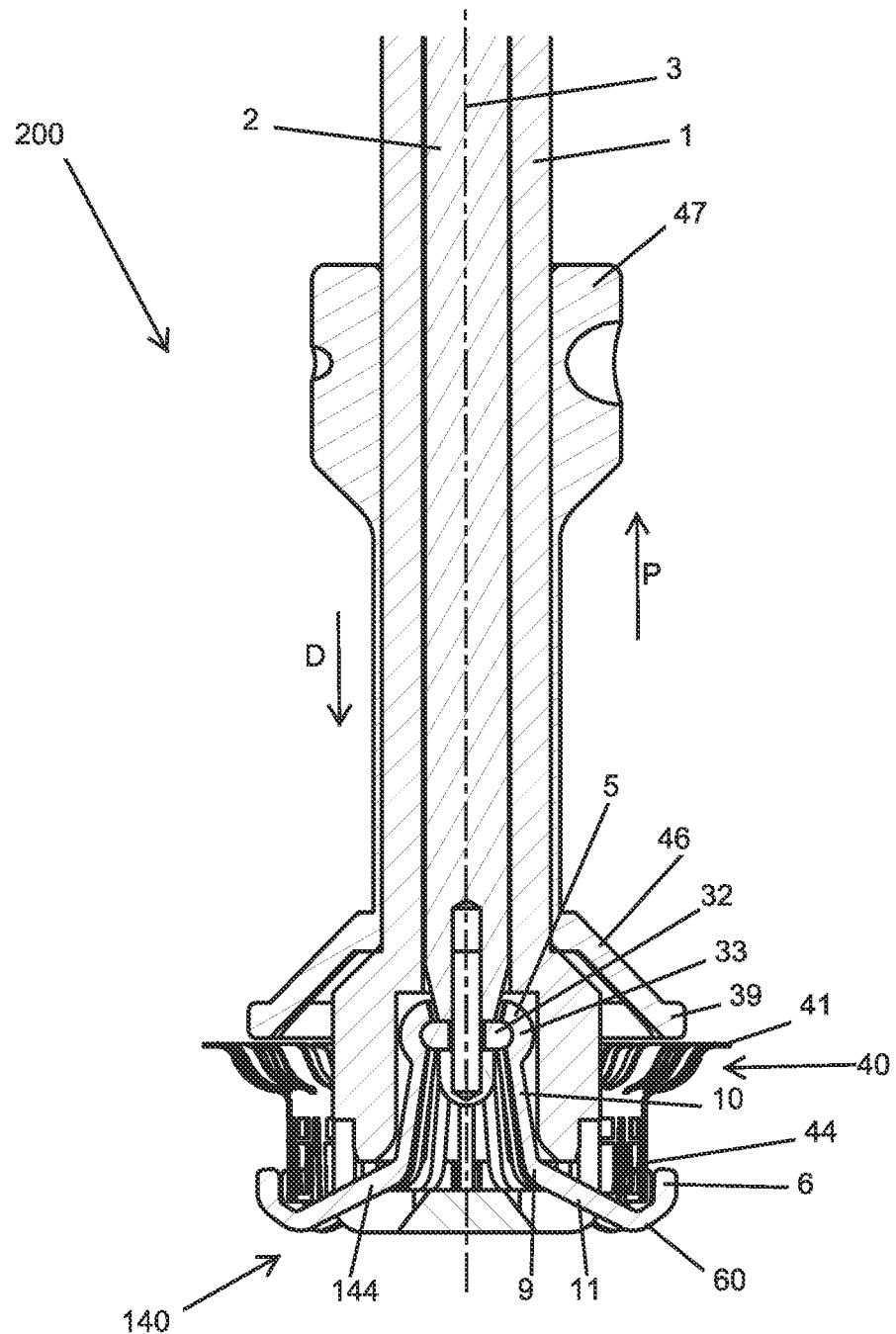
FIG. 3a shows a condition in which the manipulator holds the prosthesis in place and FIG. 3b shows a condition in which the manipulator has released the prosthesis.

FIG. 3 shows a second embodiment of a medical instrument 200 according to the first aspect. This medical instrument is also intended as an applicator for the implantation of a similar type of prosthesis 40 as discussed in the embodiment according to FIG. 1. In the second embodiment as shown in FIG. 3, the same reference numbers and symbols are used for corresponding items as in the first embodiment according to FIGS. 1 and 2. From the second embodiment according to FIG. 3, only a distal part of the medical instrument is shown. The proximal part which is not shown may be designed in the same manner as in the embodiment according to FIGS. 1 and 2.

The main difference between the second embodiment according to FIG. 3 and the first embodiment according to FIGS. 1-2 is that the plurality of fingers 4 in the embodiment according to FIG. 3 is designed differently. To distinguish the plurality of fingers from this second embodiment shown in FIG. 3 from the plurality of fingers from the first embodiment according to FIGS. 1 and 2, the plurality of fingers 4 according to the second embodiment is designated by the term 'third plurality of fingers', and the different reference number 144 is used therefor. As evident from FIG. 3, this does not therefore mean that a first and/or second plurality of fingers must also be present.

Although there is no difference in content, but only a difference in representation, the support ring 39 is shown in the second embodiment according to FIG. 3 in a condition in which said support ring acts as a stop for the proximal side of the prosthesis 40.

Just as in the first embodiment according to FIGS. 1 and 2, the fingers 144 in the second embodiment according to FIG. 3 also have a first finger end 5 pivotably attached to the second rod 2, and a free finger end 6. Furthermore, the fingers 144 of the third plurality of fingers also have a first curved zone 9. The fingers 144 of the third plurality of fingers are oriented in such a way that the pivotable attachment to the second rod 2 is located proximally from the free finger ends 6, viewed from the perspective of the operator. The fingers 144 of the third plurality of fingers therefore extend in relation to the first plurality of fingers 4 according to the first embodiment in the opposite direction. The fingers 144 of the third plurality of fingers furthermore project inside along the prosthesis 40 in order to grip from within via a hook 60 on the distal flange feet 44 at the distal end thereof, viewed from the perspective of the operator.

Figure 3B:
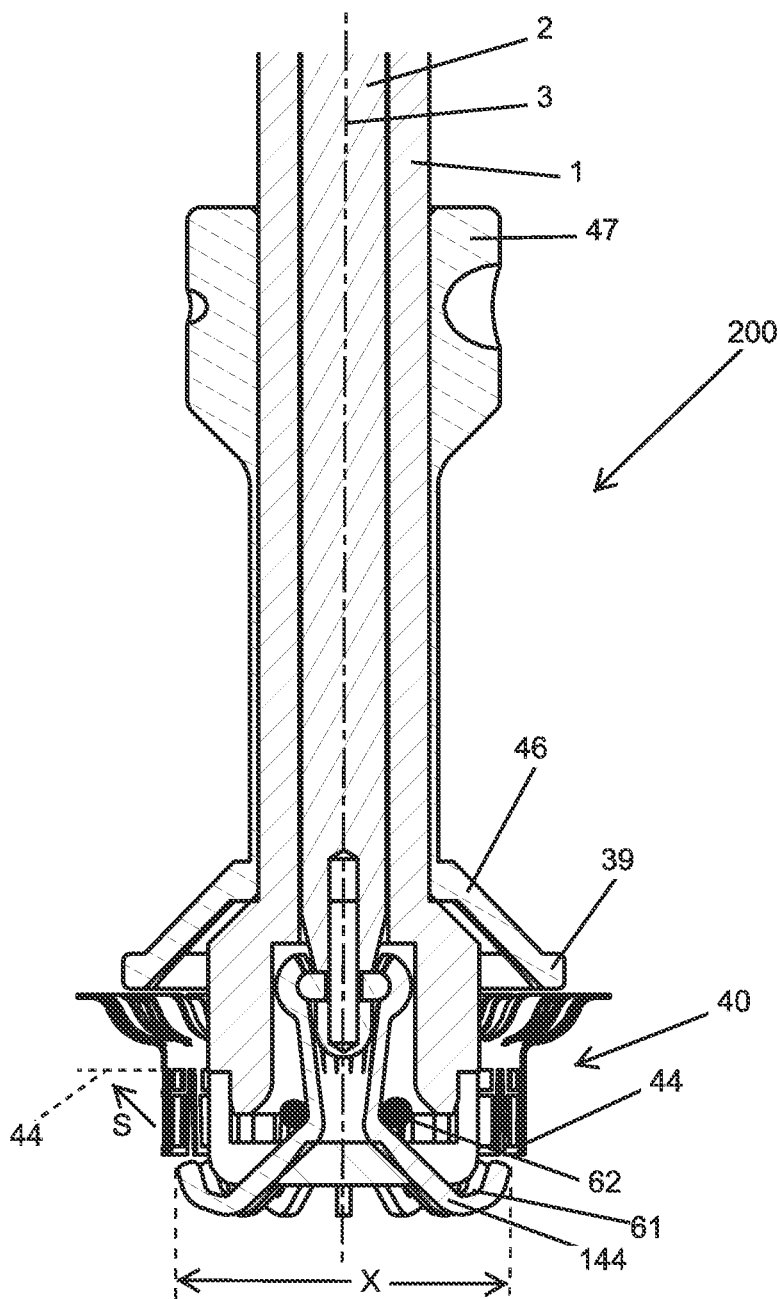

By then shifting the second rod 2 in relation to the tube 1 in the distal direction, viewed from the perspective of the operator, the hooks 60 fall free from the distal flange feet 44. In order to ensure here that the fingers 144 of the third plurality of fingers are held together in the condition shown in FIG. 3b with a smaller span, an elastic tensioning ring 62 (shown in FIG. 3b), such as a spring or an elastic, may optionally be provided. As shown in FIG. 3b, the span X, following the detachment of the prosthesis 40, is smaller than the diameter of the prosthesis 40. As further indicated by the arrow S and broken lines, the distal flange feet, after they have been released by the fingers 144, can be flipped or bent over from the axial extended position to a radial position.

The medical instrument according to the second embodiment as shown in FIG. 3 offers the advantage that it takes up little space on the distal side of the prosthesis 40, viewed from the perspective of the operator. This medical instrument 200 is therefore very suitable if there is no space available in the patient on the distal side of the prosthesis.

Figure 4:
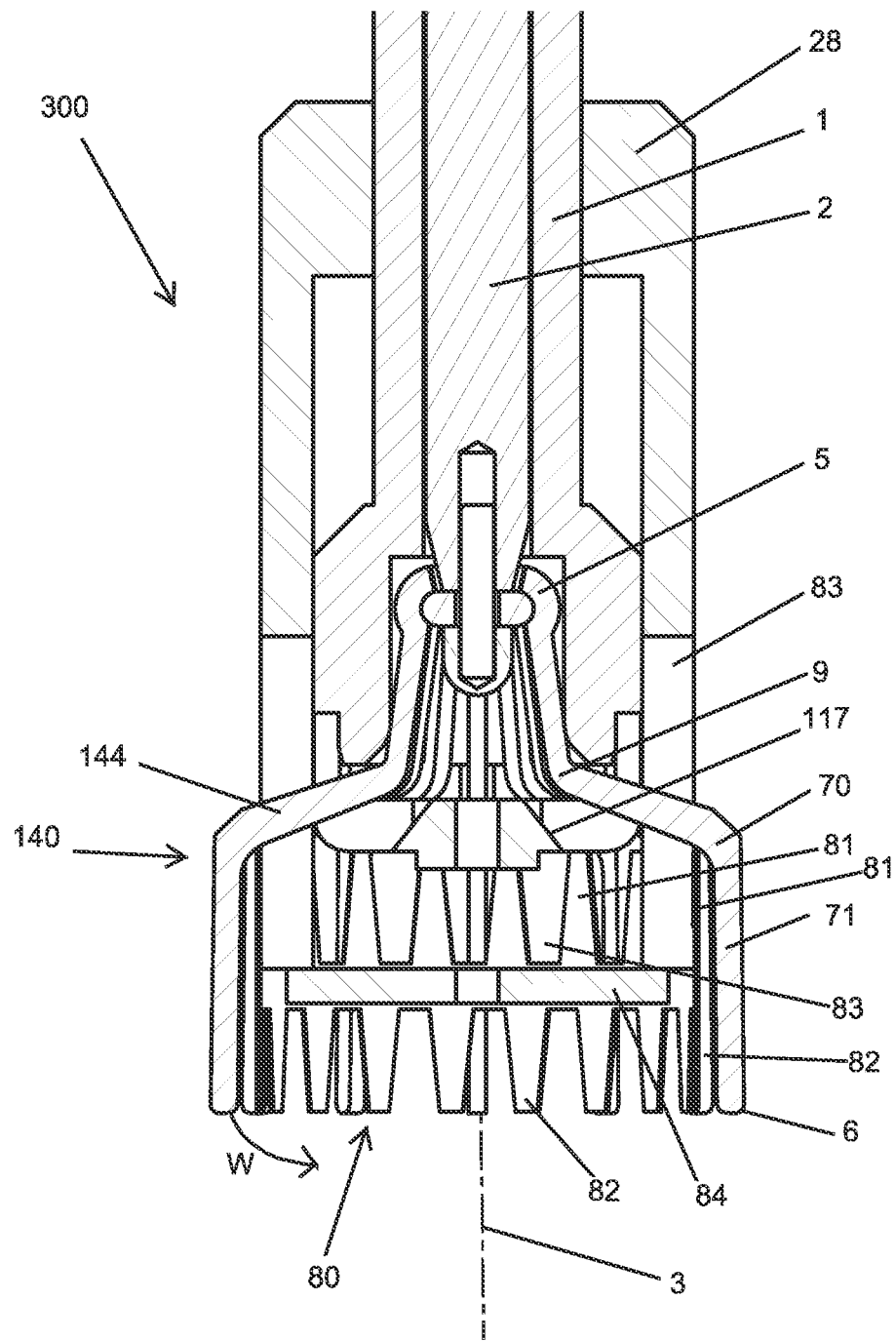
FIG. 4 shows a schematic, longitudinal section view of a third embodiment of a medical instrument, used as an applicator, according to the first aspect.

FIG. 4 shows a third embodiment of a medical instrument 300 according to the first aspect. This medical instrument 300 is also intended in particular as an applicator for a prosthesis 80. This prosthesis 80 is of a type similar to that of the prosthesis 40 from FIGS. 1-3. The main difference is that, in the case of the prosthesis 80, not only the distal flange feet 82 but also the proximal flange feet 81 are bendable from an axial extended position to a radial position (not shown in FIG. 4). In the third embodiment as shown in FIG. 4, the same reference numbers and symbols are used for corresponding items as in the first and second embodiment according to FIGS. 1 and 2. From the third embodiment according to FIG. 4, only a distal part of the medical instrument is in turn shown. The proximal part which is not shown may be designed in the same manner as in the embodiment according to FIGS. 1 and 2.

The medical instrument 300 according to the third embodiment is similar to some extent to the medical instrument 200 according to the second embodiment. The main difference compared with the medical instrument 200 according to the second embodiment, is that, in the case of the medical instrument 300 according to the third embodiment, the fingers 144 of the third plurality of fingers do not project inside through the prosthesis, but run outside along the prosthesis. For this purpose, the fingers 144 of the third embodiment are modified compared with the fingers 144 according to the second embodiment essentially in the hooks 60 (of the second embodiment). Instead of hooks 60, the fingers 144 are extended here by means of a second curved zone 70 in the distal direction, viewed from the perspective of the operator. The extended part 71 forms a so-called gripping section, with which the fingers grip outside around the prosthesis 80 in order to overlap both the proximal flange feet 81 and the distal flange feet 82 from outside and hold them in the extended position, thereby ensuring that the proximal and distal flange feet 81, 82 can only return to a radial position after they have been released by the fingers 144.

A further difference is that the tube 1 is provided with a cylindrical carrier part 28 with slots 83 therein, through which the fingers 144 in the position shown in FIG. 4 can project outwards. If the prosthesis 80 has been detached, the fingers 144 pivot according to the arrow W radially inwards and come (not shown) to lie entirely within the carrier part 28 against the contact surface 117. This carrier part 28 is therefore a slotted element 34 as discussed in the first embodiment with reference to FIGS. 1-2. In order to cause the fingers 144 to move reliably to the reduced-span condition, an elastic tensioning ring (not shown in FIG. 4) can be provided, corresponding to the second embodiment according to FIG. 3.

In order to hold in place the prosthesis 80 carried on the distal lower end of the carrier part 28 if the third plurality of fingers 144 is drawn upwards in the proximal direction, the carrier part 28 can be provided at the distal end, viewed from the perspective of the operator, with cams (not shown) projecting radially outwards, which project into an intermediate space 83 between adjacent proximal flange feet 81.

In a manner corresponding to that described with reference to FIGS. 1-2, the tube 1 can be shifted in relation to the second rod 2 in the proximal direction, viewed from the perspective of the operator, in such a way that the gripping sections 71 of the fingers 4 first come to lie proximally from the distal flange feet 82 and, with further proximal retraction, also come to lie proximally from the proximal flange feet 81. It is thus possible to allow first the distal flange feet 82 to bend round to a radial position and only thereafter the proximal flange feet 81. It is noted that it may also be possible for the proximal flange feet 81 to change already in advance to the radial position. In this case, the proximal flange feet will project through between adjacent fingers 144 and no longer need to be bent to a radial position.

In order to prevent the second rod 2 from being able to be pushed too far in the distal direction out of the tube 1, a retainer plate 84 is provided on the underside of the carrier part 28.

An applicator as shown in FIG. 4 is not only usable for implanting a so-called 'prosthesis of the type with a tubular element', but can also be used for other types of prostheses, such as a compressible and/or expandable prosthesis or device, for example a stent.

FIG. 5 shows a fourth embodiment of a medical instrument 400 according to the first aspect. The medical instrument 400 is used here as an applicator for a stent 90. This stent 90 may be provided on the inside or otherwise with a biological or artificial valve prosthesis, which can expand from a compressed condition when the stent expands. The stent 90 may therefore optionally also be a so-called 'valved stent'. With reference to the previously described embodiments of a medical instrument according to the first aspect, corresponding items are again denoted here with corresponding reference numbers and symbols. From the fourth embodiment according to FIG. 5, only a distal part of the medical instrument is in turn shown. The proximal part which is not shown may be designed in the same manner as in the embodiment according to FIGS. 1 and 2.

The embodiment as shown in FIG. 5 is a double-headed embodiment. This applicator 400 has a distal 'head' with a first plurality of fingers 4 and a proximal 'head' with a second plurality of fingers 94. The first plurality of fingers 4 and the second plurality of fingers 94 are designed as mirror images of one another and have free finger ends 6 pointing towards one another and first finger ends 5, which are attached in a hinged manner, facing away from one another. The fingers 4 of the first plurality of fingers and the fingers 94 of the second plurality of fingers both have a gripping section 71 and can jointly grasp the stent 90 from opposite sides.

FIG. 5a shows the applicator 400 in a condition with the stent 90 mounted thereon in the compressed condition. This is also the condition of the stent and the applicator 400 when the stent is delivered to the intervention location in the patient. Having arrived at the intervention location, the fingers 4 of the first plurality of fingers and the fingers 94 of the second plurality of fingers are capable of pivoting outwards from the first position shown in FIG. 5a to a wider position shown in FIG. 5b, referred to here as the second position. Thus, the fingers 4 of the first plurality of fingers and the fingers 94 of the second plurality of fingers can jointly accompany the expansion of the stent 90 to the expanded condition shown in FIG. 5b. Displacement of the hinged attachments of the first finger ends of the first plurality of fingers 4 and the second plurality of fingers 94 is not yet necessary here.

In order to be able to displace the first plurality of fingers 4 and the second plurality of fingers 94 in relation to the stent 90 and also in relation to one another, the medical instrument is constructed from three rods, 1, 2 and 91, which are movable in relation to one another. The first rod 1 may be designed here as a tube in which both the second rod 2 and the third rod 91 are housed in such a way that they are reciprocally displaceable in the longitudinal direction of the medical instrument. Here, the second rod 2 carries the first finger ends 5 of the first plurality of fingers 4 via a hinged attachment. The third rod 91 carries the first finger ends 5 of the second plurality of fingers 94 via a pivoting attachment. The fingers 94 of the second plurality of fingers project via slots 93 outside the first rod 1.

As shown in FIG. 5c, the stent 90 can be released from the expanded condition shown in FIG. 5b by, on the one hand, shifting the first plurality of fingers 4 in relation to the stent 90 in the distal direction D and, on the other hand, by shifting the second plurality of fingers 94 in relation to the stent 90 in the proximal direction P. These shifts of the first plurality of fingers 4 and the second plurality of fingers 94 can take place independently from one another, but a linked movement can also take place, wherein they are shifted simultaneously, to the same extent or otherwise.

As soon as the first and second fingers 4, 94 no longer overlap the stent 90, viewed in the direction perpendicular to the longitudinal centre line 3, the first and second fingers 4, 94 can be pivoted to the narrower position shown in FIG. 5c. This pivoting can take place in a mechanically controlled manner or automatically, for example, if, in a manner comparable with the elastic tensioning ring 62 shown in FIG. 3, a resilient element is provided around the first plurality of fingers 4 or second plurality of fingers 94. However, the resilience of a tensioning element of this type will be less than the force generated during the expansion of the stent 90, as the expansion of the stent 90 would otherwise be hindered.

If the angle of inclination of the inner guide 51 in relation to the longitudinal centre line 3 is made smaller, it is even possible here for the free finger ends 6 of the first plurality of fingers 4 to dip via the slots 92 into the sleeve part 195 on the distal end of the first rod 1. This eliminates the risk of the free ends 6 of the first plurality of fingers 4 being able to damage tissue of the patient when the applicator is retracted in the proximal direction P. This is less important for the free ends 6 of the second plurality of fingers 94, as they point during the retraction in a direction opposite to the direction of retraction P. However, in the condition shown in FIG. 5c, these free ends 6 can also dip if required inside into the sleeve part 195 by extending the slots 93 on the underside by shortening the sleeve part 195 in the region of 96.

In the case of stents, they are normally delivered to the intervention location in a sleeve. The sleeve is then withdrawn in situ and the stent expands. If the stent is not positioned at precisely the correct location and the sleeve has already been withdrawn (too far), the stent can then no longer be repositioned. Retrievable stents are in fact known, but once the sleeve has been withdrawn too far, it is difficult or impossible to correct this situation. The advantage of the applicator according to FIG. 5 and also the applicator still to be discussed according to FIG. 6 is that stents can be implanted herewith in a manner which to a large extent allows for correction. In any event, the pivotable fingers make it possible, following expansion of the stent, for the stent to be compressed once more and for the stent to be entirely removed or repositioned. In addition thereto, but also entirely separately therefrom, the pivotable fingers enable the stent expansion to be carried out in an extensively and particularly controlled manner.

FIG. 6 shows a fifth embodiment of a medical instrument 500 according to the first aspect. This medical instrument is also intended as an applicator, in this case an applicator for a stent or so-called 'valved stent'. With reference to the previously described embodiments of a medical instrument according to the first aspect, corresponding items are again denoted here with corresponding reference numbers and symbols. From the fifth embodiment according to FIG. 6, only a distal part of the medical instrument is in turn shown. The proximal part which is not shown may be designed in the same manner as in the embodiment according to FIGS. 1 and 2.

The prosthesis is denoted in FIG. 6 by reference number 96 and can be distinguished from the prosthesis 90 shown in FIG. 5 in particular by a 'prosthesis of the type with a tubular element' separately disposed hereon or integrated herewith, as described in previously repeatedly mentioned PCT applications of the inventor. A prosthesis such as the prosthesis 96 has a tubular configuration and comprises a tubular part 198 with proximal flange feet 83 and distal flange feet 82 provided thereon. Of these flange feet, at least the distal flange feet 82 can be moved from an axial position to a radial position. In the case of the fifth embodiment according to FIG. 6, the proximal flange feet 83 can also be moved from an axial position to a radial position 83. The prosthesis 96 is then attached to surrounding tissue then by clamping tissue between the proximal flange feet 83 and distal flange feet 82 and/or by anchoring the proximal flange feet 83 and/or distal flange 82 in surrounding tissue.

The medical instrument 500 according to the fifth embodiment differs from the medical instrument 400 according to the fourth embodiment particularly in the sense that the free ends 6 of the first plurality of fingers 4 and the second plurality of fingers 94 are provided with gripping elements 95. These gripping elements 95 are formed here as a central slot 97 with a gripping part on either side, i.e. an inner gripping part 98 and an outer gripping part 99. The gripping parts 98 and 99 can run roughly parallel. In this embodiment, the inner gripping part 98 on the inside of fingers 4 and 94 is in each case shorter than the outer gripping part 99 on the outside of the fingers 4 and 94. It is noted that the inner gripping part 98 and the outer gripping part 99 may possibly also be of equal length.

Figure 6A:
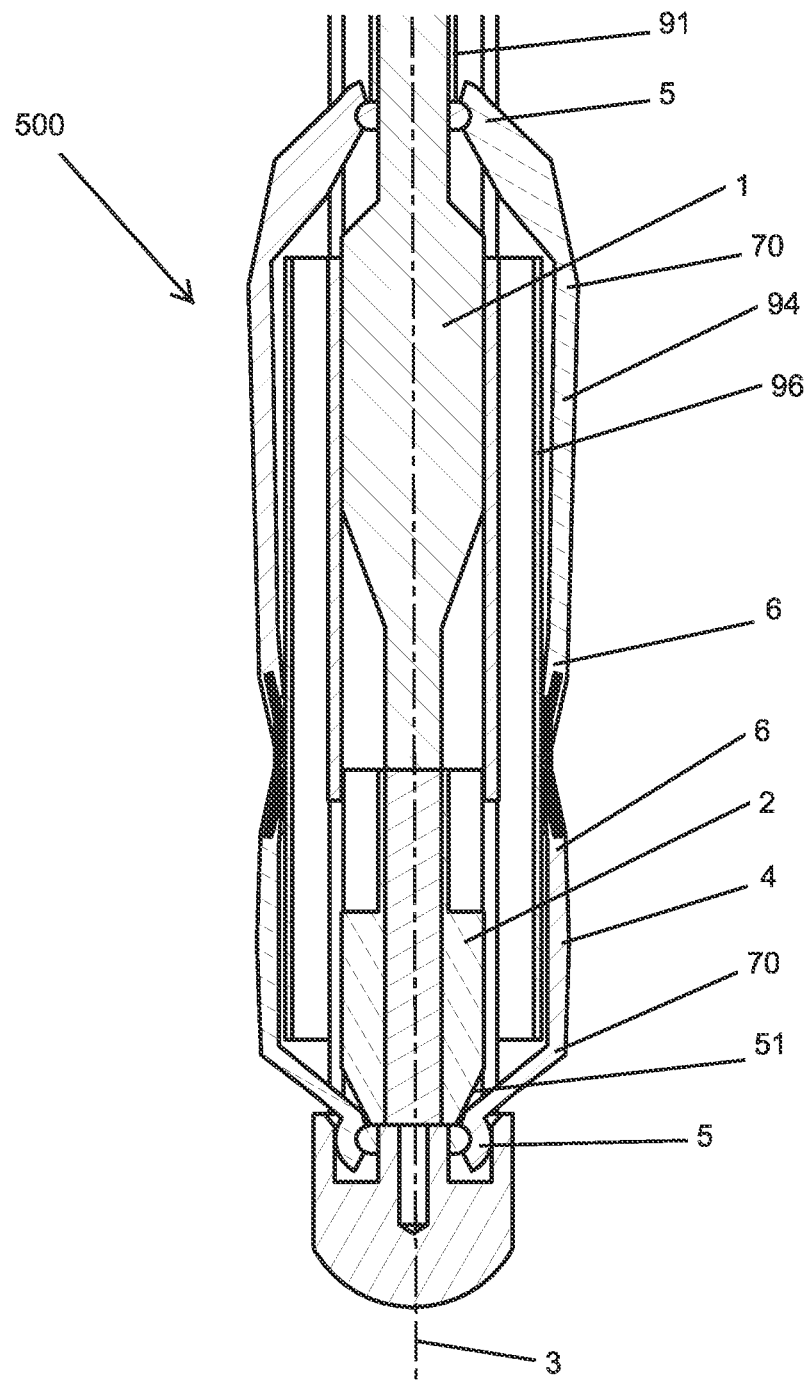
FIG. 6a shows a condition in which the manipulator holds the compressed prosthesis in place.

With reference to FIG. 6*a*, the proximal flange feet 83 and the distal flange feet 82 are accommodated in the initial condition in the slots 97 of the gripping elements 95 of the second plurality of fingers 94 and the first plurality of fingers 4 respectively.

Figure 6B:
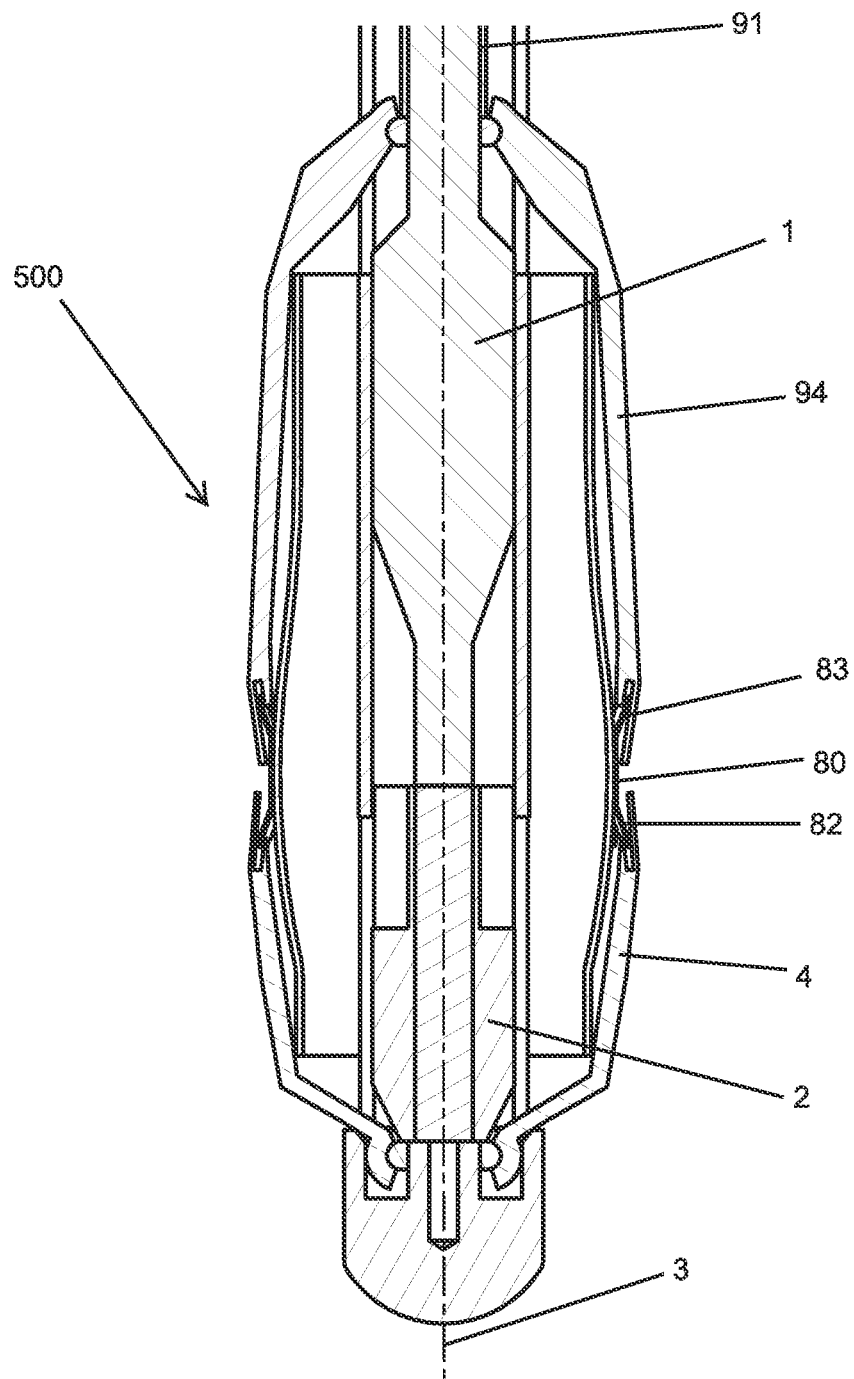
FIG. 6b shows a condition in which the manipulator holds the expanded prosthesis in place.

By designing the gripping parts 99 of the gripping elements 95 located on the outside as sufficiently long (and, in addition, possibly the slots 97 of the gripping elements 95 as sufficiently deep), viewed in the longitudinal direction of the longitudinal centre line 3, the first plurality of fingers 4 and the second plurality of fingers 94 are capable, in a manner corresponding to that shown in FIG. 5 of accompanying the expansion of the prosthesis 96, but without releasing the proximal flange feet 83 and the distal flange feet 82. This is shown in FIG. 6*b*, where an expanded prosthesis 96 is shown, the proximal flange feet 83 and the distal flange feet 82 of which are still held in place by the gripping elements 95.

The first plurality of fingers 4 and the second plurality of fingers 94 are then displaced in relation to the prosthesis 96 in a manner corresponding to that shown in the embodiment according to FIG. 5 in such a way that the distal flange feet 82 and proximal flange feet 83 are released. The condition thus reached is shown in FIG. 6*c*.

The distal flange feet 82 and the proximal flange feet 83 can then move from the axially extended position to the radial position for anchoring in and/or on surrounding tissue. This condition is shown in FIG. 6*d*.

Figure 6C:
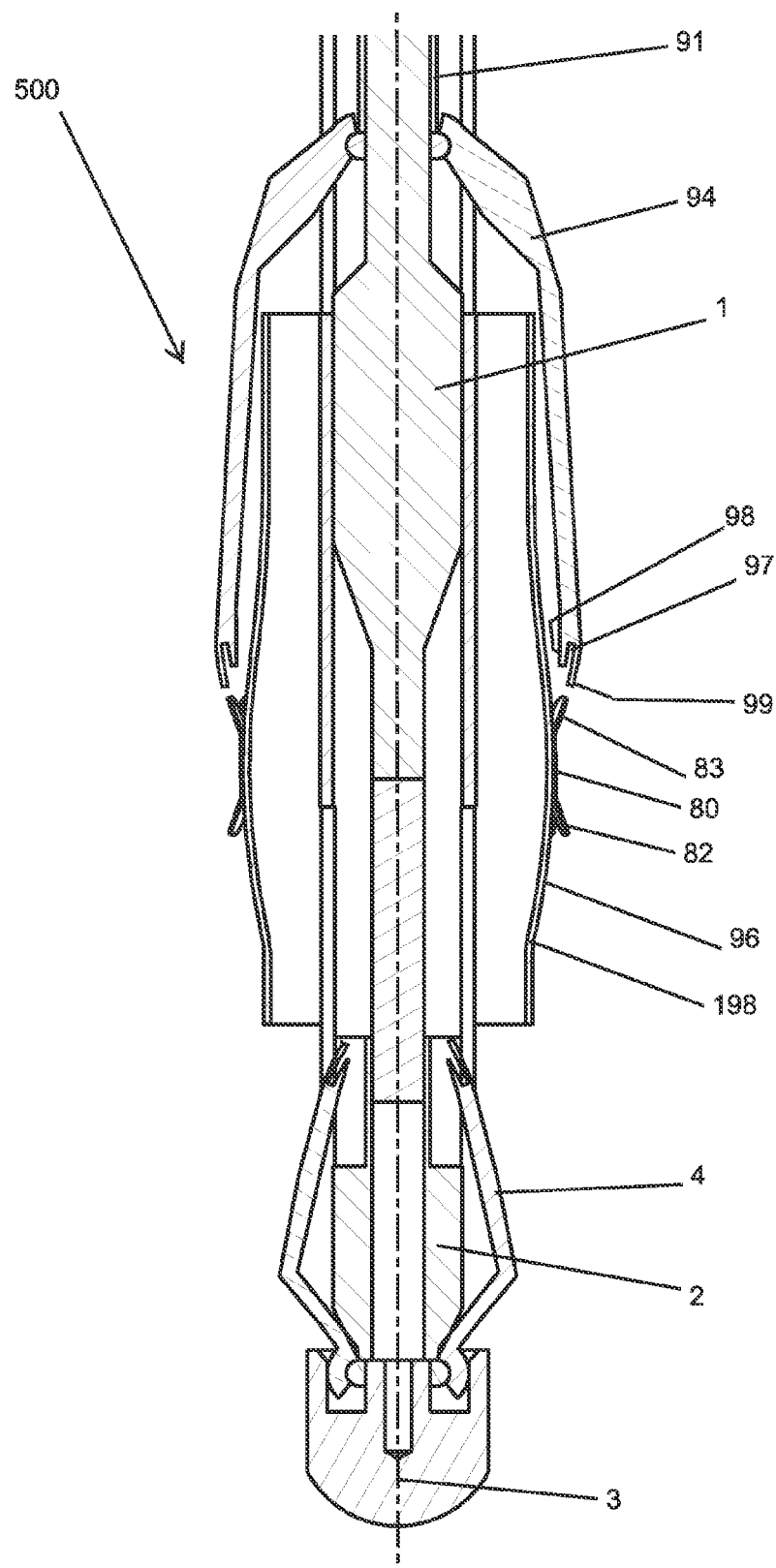
FIG. 6c shows a condition in which the manipulator partially releases the expanded prosthesis in place.
Figure 6D:
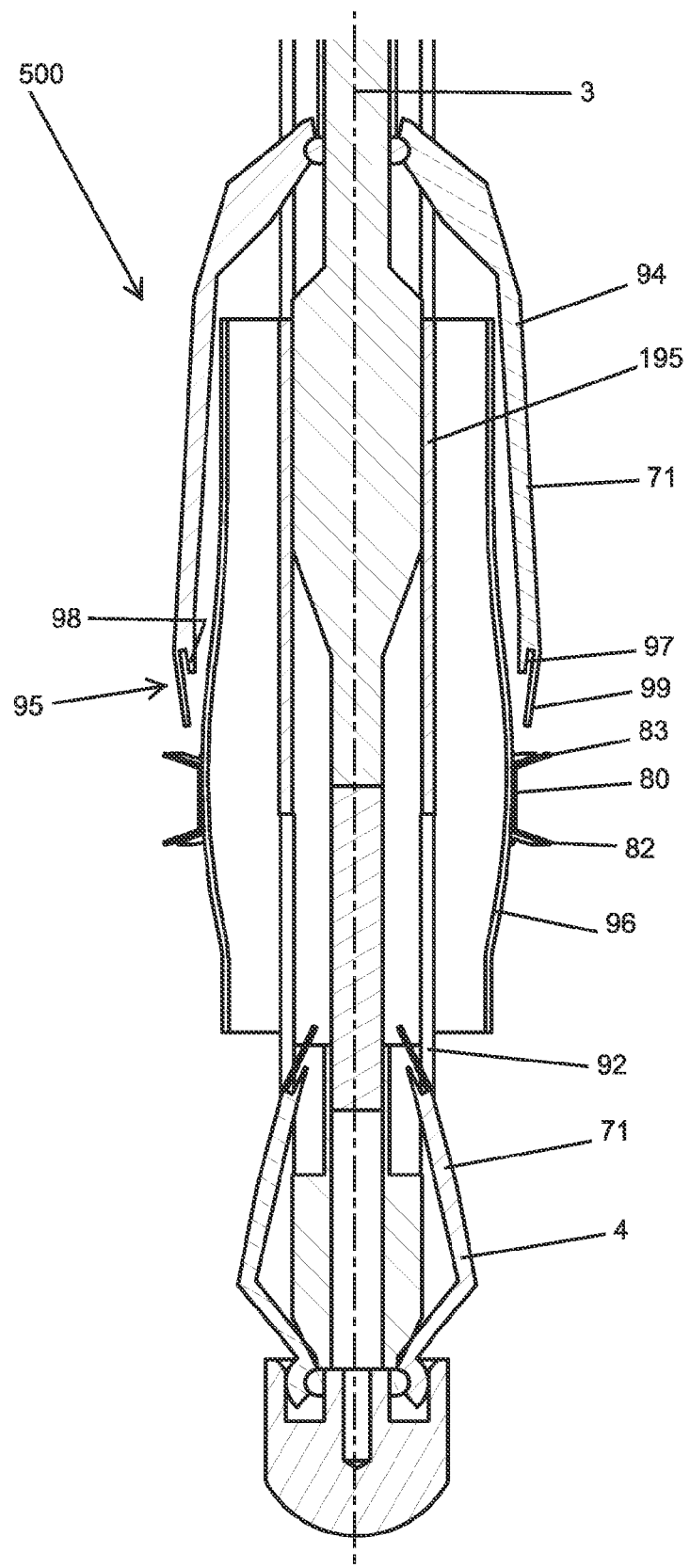
FIG. 6d shows a slightly later condition in which the manipulator has partially released the expanded stent.

As can furthermore be seen in FIGS. 6*c* and 6*d*, the free ends 6 of the first plurality of fingers 4 dip via the slots 92 into the tube part 95 (corresponding to the manner described in FIG. 5*c* but now actually shown).

The embodiment according to FIG. 6 is suitable in particular for implanting a so-called 'valved stent'. As shown in FIG. 6, sufficient space in fact remains centrally in the prosthesis 96 to accommodate the valve flaps and commissures of a valve. The central part of the applicator extending through the prosthesis 96 can in fact be designed as very slim. It should be clear that the embodiment as shown in FIG. 6 is suitable not only for implanting a stented valve prosthesis, but also for implanting a conventional stent which is provided for anchoring in surrounding tissue or is integrated with a 'prosthesis of the type with a tubular element' as described in detail in earlier PCT applications of the inventor.

The great advantage of the applicator according to FIG. 6 is that a stent can be implanted herewith with anchoring elements mounted thereon, wherein the stent can first be allowed to expand and only thereafter can the anchoring elements be released to be anchored in surrounding tissue, such as the annulus of a heart valve. The anchoring elements can thus be prevented from moving prematurely to an anchoring position and thereby no longer being able to be anchored firmly in the surrounding tissue or even no longer being able to be anchored at all.

FIG. 7 shows very schematically a medical instrument 600 according to a sixth embodiment. This medical instrument is shown here as an applicator for an expandable stent 90. FIG. 7*a* shows the medical instrument 600 and the stent 90 in a compressed condition, FIG. 7*b* shows the stent 90 and the medical instrument 600 in an expanded condition, wherein the stent 90, however, has not yet been detached, and FIG. 7*c* shows the medical instrument 600 and the stent 90 in a condition after the stent 90 has been expanded and detached. With reference to the previously described embodiments of a medical instrument according to the first aspect, corresponding items are again denoted here with corresponding reference numbers and symbols. From the sixth embodiment according to FIG. 7, only a distal part of the medical instrument is in turn shown. The proximal part which is not shown may be designed in a manner comparable with the embodiment according to FIGS. 1 and 2.

The main difference compared with the previously described embodiments, in particular the fourth embodiment according to FIG. 5 and the fifth embodiment according to FIG. 6 is that the fingers of the first plurality of fingers 4 and the second plurality of fingers 94 are not pivotable here. The displacement of the fingers 4 and 94 is implemented here by means of a translation along a surface which lies obliquely in relation to the longitudinal centre line 3. The first plurality of fingers 4 and the second plurality of fingers 94 can thus, to a substantial extent, precisely accompany the expansion of the stent 90 to virtually the outer expansion position of the stent without being hindered therein by surrounding tissue. It should be clear in this context that the gripping sections 71 of the fingers 4 and 94 are shown here as exaggeratedly thick and, viewed in a direction perpendicular to the longitudinal centre line 3, may therefore be designed as much thinner.

As shown in FIG. 7, this mobility of the fingers 4 and 94 is achieved by providing the second rod 2 with a first conical guide surface 101 and by providing the first plurality of fingers 4 at the first finger ends 5 with a guide part 102 which is shiftable along and in contact with the first conical guide surface 101 in order to displace the fingers 4 from a first position to a second position, wherein the distance from the guide parts 102 to the longitudinal centre line 103 differs in the first position and the second position. In a corresponding manner, the third rod 91 is provided with a second conical guide surface 103. The fingers 94 of the second plurality of fingers are in turn provided in a corresponding manner at a first finger end 5 with a guide part 102 which is shiftable along and in contact with the second conical guide surface 103 from a first position to a second position. The conical guide surfaces 101 and 103 face towards one another here, and the free ends 6 of the first plurality of fingers 4 and the free ends 6 of the second plurality of fingers 94 similarly face towards one another.

With regard to the medical instrument 600 as shown in FIG. 7, it is noted that, from the first plurality of fingers 4 and the second plurality of fingers 94, only one finger with the associated guide part 102 is shown in each case. The purpose of this is to maintain clarity in FIG. 7. In practice, the first plurality of fingers 4 and the second plurality of fingers 94 will each consist of a plurality of fingers disposed in a distributed manner around the longitudinal centre line 3. From a practical point of view, the number of fingers per plurality will be at least three. In practice, this will normally be expected to be 4, 5, 6, 7, 8, 9, 10, 11 or 12.

Although the gripping sections 71 and the guide part 102 of a respective finger will normally be rigid, i.e. immovable, in relation to one another, it is also optionally possible for the gripping sections 71 to be designed as pivotable in relation to the guide part 102. For example, as described earlier with reference to FIGS. 1-6.

The first plurality of fingers 4 can optionally be interconnected by means of a resilient tensioning ring 62 which extends around the longitudinal centre line 3 and is otherwise comparable with the tensioning ring 62 as shown in FIG. 3b in order to hold them in position on the medical instrument. However, this can also be done in a different manner with the aid of different means.

Once the medical instrument and the stent 90, in the compressed condition, as shown in FIG. 7a, have arrived at the intervention location, the stent 90 can then be expanded in a completely controlled manner by pressing the second rod and the third rod towards one another, as a result of which the reciprocal interval Q1, as shown in FIG. 7a, between the conical surfaces 101 and 103, decreases to Q2, as shown in FIG. 7b. The two tensioning rings 62 are thereby stretched and hold the first plurality of fingers 4 and the second plurality of fingers 94 positioned as such on the instrument, but at a greater distance from the longitudinal centre line 3.

Once the stent 90 has then sufficiently or completely expanded, the second rod 2 and the third rod and 91 can again be drawn out from one another in order to increase the distance Q2 to the distance Q3, as shown in FIG. 7c. The gripping sections 71 of the first plurality of fingers 4 and the second plurality of fingers 94 will thereby be detached from the stent 90. The tensioning rings 62 will then ensure that the first plurality of fingers 4 and the second plurality of fingers 94 move from the wide position shown in FIG. 7b to the constricted position shown in FIG. 7c, wherein said constricted position may even have a smaller span Q3 than in the initial condition according to FIG. 7a. The medical instrument 600 can then be removed from the patient through the stent 90.

Although the medical instrument 600 according to the sixth embodiment has been described on the basis of a double-headed design, it will be clear that it may also be designed with one single plurality of fingers, i.e. the first plurality of fingers 4 or the second plurality of fingers 94. Thus, it will, for example, be clear that the embodiment according to FIGS. 1-2 can in fact easily be implemented by means of a plurality of fingers 4 corresponding to the sixth embodiment shown in FIG. 7 and that the embodiments according to FIGS. 3-6 can also be implemented with one conical surface per plurality of fingers and fingers corresponding to the design according to FIG. 7.

FIG. 8 shows a medical instrument 700 according to a seventh embodiment of the first aspect. This medical instrument 700 is, in particular, suitable as an applicator for a ring prosthesis 800 according to the second aspect of this application. Further details of this ring prosthesis can be found in FIG. 9, which shows a first design of the ring prosthesis according to the second aspect. To avoid misunderstanding, it is, however, noted that, in the ring prosthesis in FIG. 9, the pins 801 are provided on the outside of the ring prosthesis, whereas the pins of the ring prosthesis in FIG. 8 are provided on the inside of the ring prosthesis. However, the instrument 700 is also very readily usable for the ring prosthesis as shown in FIG. 9 without this instrument 700 requiring any adaptation for this purpose.

With reference to the previously described embodiments of a medical instrument according to the first aspect, corresponding items are again denoted here with corresponding reference numbers and symbols. From the seventh embodiment according to FIG. 8, only a distal part of the medical instrument is in turn shown. The proximal part which is not shown may be designed in the same manner as in the embodiment according to FIGS. 1 and 2.

The medical instrument 700 comprises a first rod 1 in the form of a tube with a second rod 2, shiftable in relation to the tube 1, housed therein. The second rod 2 is provided with a conical surface at its distal end, viewed in relation to the apparatus. This conical surface is not visible in FIG. 8, but does not differ per se in design and operation from the conical surface 103 shown in FIG. 7. Fingers 4 are supported on the conical surface of the second rod in the same way as the fingers 94 are supported on the conical surface 103 in FIG. 7. The tube 1 is provided with slots 106, in which the fingers 4 are guided axially, and which hold the fingers 4 in their place. In the same way as the fingers 94, the fingers projecting outwards from the slots 106 have a free, second end 6 and a first end with an oblique surface, so that the fingers 4 can shift along the conical surface of the second rod in the event of axial displacement of the second rod in relation to the fingers 4. In addition to fingers 4, the medical instrument also further comprises fingers 855. These fingers 855 can possibly be mounted immovably on the tube 1. In order to be able to reduce the span of the distal end of the instrument 700, for example in order to facilitate the delivery to the intervention location, it is desirable for the fingers 855 to be movable in a radial direction in order to be able to retract them in a radially inward direction and/or to project them further outwards in a radially outward direction. This can be implemented in the manner described earlier in relation to the first aspect, for example by means of a third rod with a conical surface which interworks with an oblique surface on the inside of the fingers. This third rod may be designed as a tube and may lie between the first and second rod, but it may also be located in the second rod, if the second rod is designed as a tube. If the tube 1 needs to be held fixed in relation to the intervention location and the prosthesis also needs to be able to be pushed away in the distal direction, it is then expedient if the fingers 855 are guided in axial slots which are formed in the tube 1.

Figure 9B:
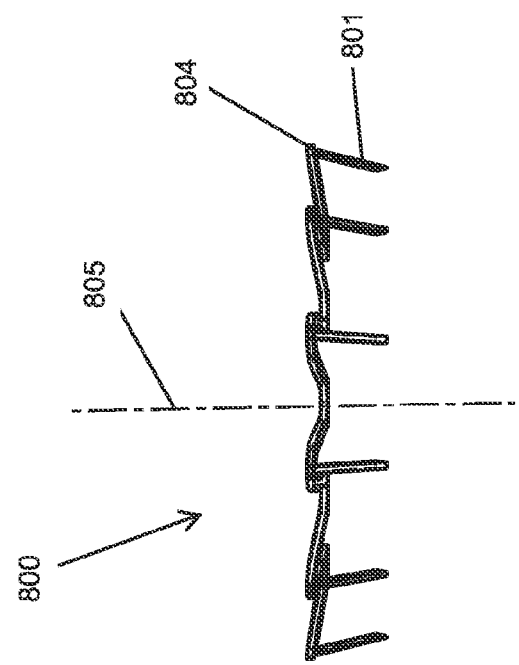
FIG. 9a is a perspective view and FIG. 9b is a side view.
Figure 9A:
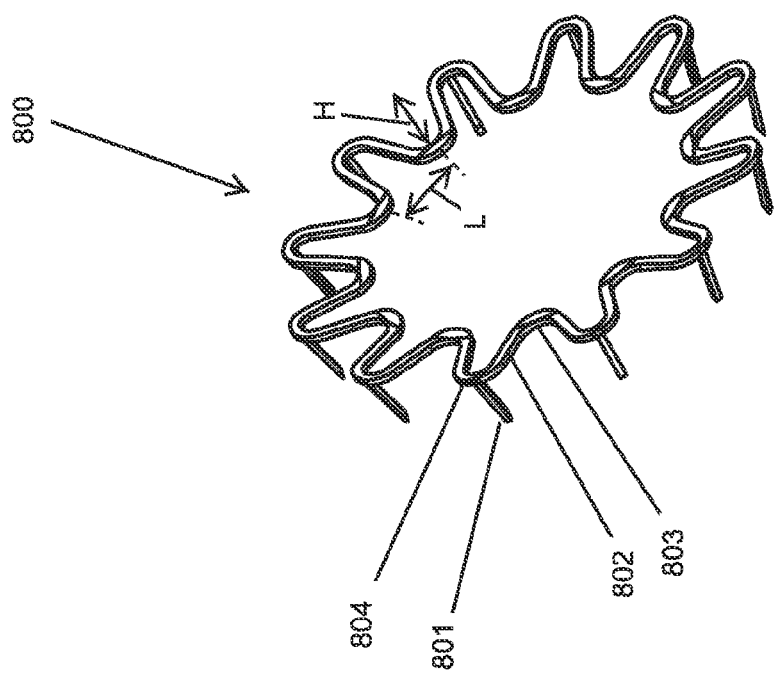

With reference to FIG. 9, the ring prosthesis 800 is formed from a wire 802 which extends along a waved pattern in the circumferential direction as a waved (first) ring. As shown with reference to FIG. 9a, the waved ring in this example has twelve wave peaks 804 and twelve wave troughs 803. Each wave peak 804 carries a pin 801 which extends in the direction of the axial centre line 805 of the ring prosthesis 800. As a result of the waved pattern, this ring prosthesis can be reduced in diameter or, conversely, increased in diameter. In the case of a reduction in the diameter, adjacent wave peaks 804 and adjacent wave troughs 803 will come to lie closer to one another. In the case of an increase in the diameter, adjacent wave peaks 804 and adjacent wave troughs 803 will come to lie further away from another. The wave length L, viewed in the circumferential direction of the ring, will therefore decrease in the event of a reduction in the diameter, whereas the wave height H will, conversely, increase in the event of a reduction in the diameter. Conversely, in the event of an increase in the diameter, the wave length L will increase and the wave height H will decrease.

Figure 8A:
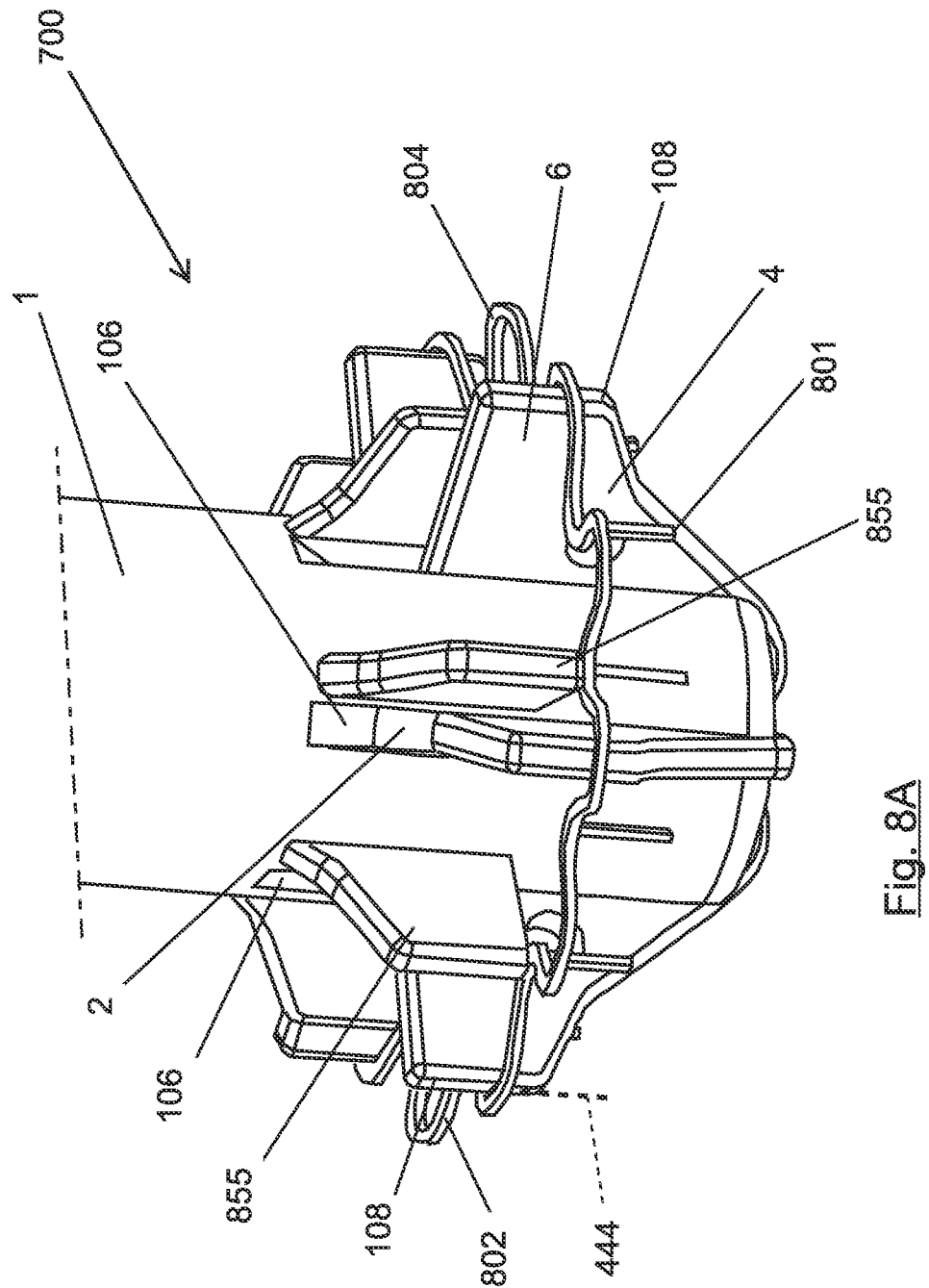
FIG. 8a shows a condition in which the manipulator carries the ring prosthesis.

If the ring prosthesis 800 is loaded onto the applicator 700 shown in FIG. 8, the fingers 4 (see FIG. 8a) will move with their free ends from the inside against the peak 804 of the wave. The pins attached to the waved ring 802 at the midpoint of the peak 804 (see the pin 444 indicated for this purpose by broken lines on the left in FIG. 8a, which presents a pin from the ring prosthesis shown in FIG. 9) will then, as shown in FIG. 8a with the dashed-line pin 444, lie against the outside 108 of the free end 6 of a finger 4. If the ring prosthesis sits higher on the fingers 4, the pin 444 will no longer project under the axial outer edge 108 of the finger 4 and therefore be protected from the environment by the axial outside 108 of a finger 4. A pin 444 can thus be prevented from prematurely being able to prick into tissue or being able to remain caught up in tissue if the applicator, or at least the distal end thereof, viewed from the perspective of the operator, is moved through the patient to the intervention location. If the pin 444 bends radially inwards in its final position, it is advantageous if a bend of this type can be temporarily held in place by the axial outside 108 of the finger 4. In the case of the ring prosthesis as shown in FIG. 8, the pins lie on the inside of the ring prosthesis, as a result of which the risk of them remaining caught up in tissue or pricking prematurely into tissue during the delivery to the intervention location is much smaller. In this case, it is advantageous if the fingers 855 are extended distally on the underside thereof, said extension not being shown in this drawing, in such a way that an extension of this type lies in the longitudinal direction along the inside of the pin 801, in order to prevent this pin 801 temporarily from bending radially inwards. A distal extension of this type of the finger 855 could then be disposed at some distance from the periphery of the finger 855, so that the underside of the periphery of the finger 855 can maintain contact from above with the upper side of the ring. In this case, the fingers 4 may also have a peripheral extension which grips from above on the ring. Implantation of the ring will then be such that, due to the distal displacement of the fingers 4, the ring is displaced distally, wherein the distal extensions of the fingers 855 act as a guide for the pins 801. As soon as these pins 801 no longer have contact with these distal extensions of the fingers 855, the pins 801 may possibly bend in a radially inward direction.

During the delivery to the intervention location, the waved ring 802 stretched out on the applicator 700 may have a smaller diameter than shown in FIG. 8a. The second rod 2 will then be retracted in a proximal direction in relation to the fingers 4. The waved ring can therefore be delivered more easily to the intervention location in the patient in a condition with a relatively smaller diameter, in particular if narrow passages must be passed through. The risk of the free ends of the pins 801 of the ring 802 inadvertently damaging a tissue or remaining caught up therein during the delivery to the intervention location can therefore also be (further) reduced.

If the ring 802 is delivered to the intervention location in the reduced-diameter condition, the ring can be modified there to the required diameter by expanding it by means of the fingers to the condition shown in FIG. 8A, by shifting the second rod 2 in the distal direction in relation to the fingers 4/tube 1. It is noted that it is also possible to deliver the ring 802 to the intervention location in the expanded condition shown in FIG. 8a.

Figure 8B:
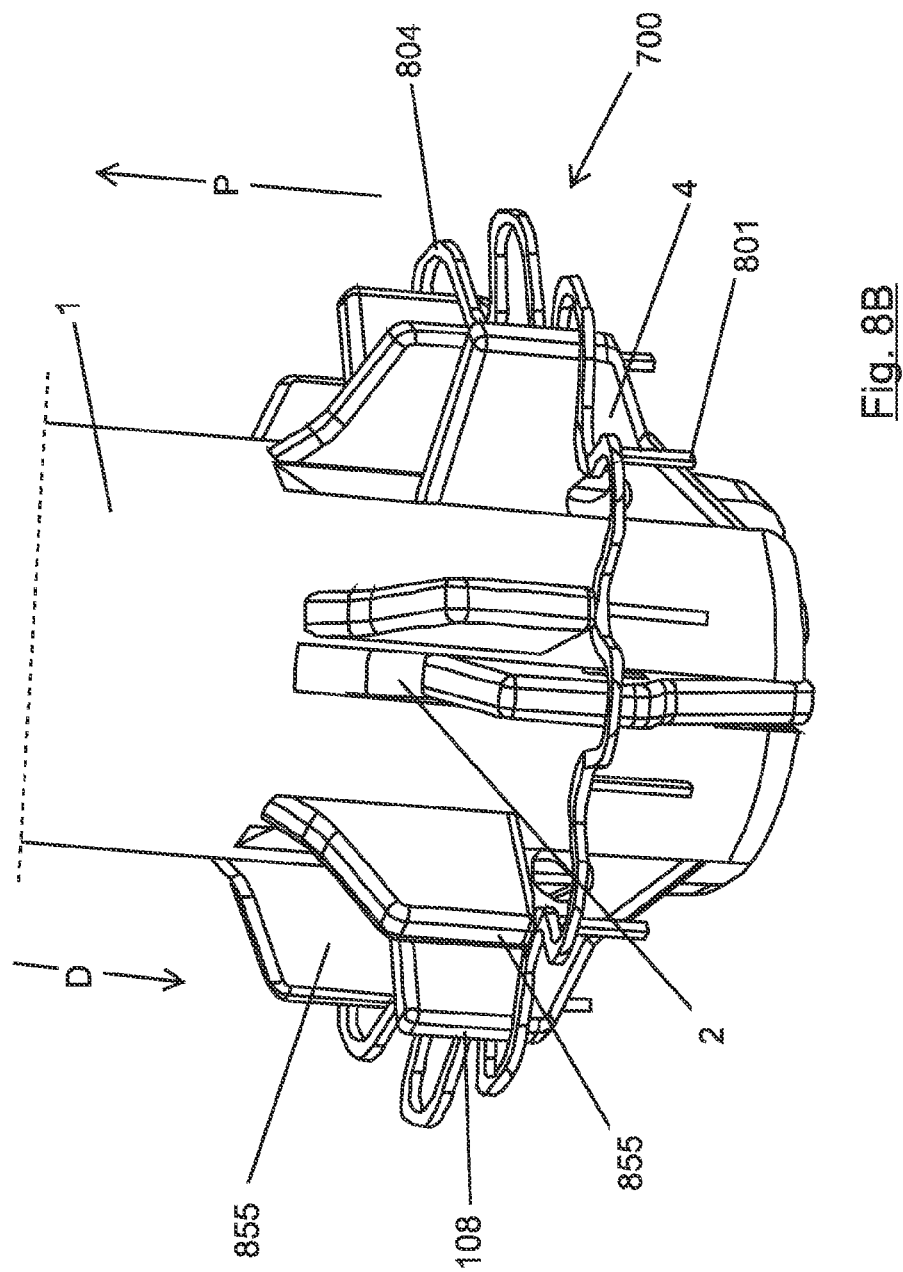
FIG. 8b shows a condition in which the manipulator has detached the ring prosthesis.

Having arrived at the intervention location, the fingers 4 can be retracted in a radial direction by retracting the second rod 2 in the proximal direction P in relation to the fingers. As shown in FIG. 8B, the fingers 4 then come to lie free from the waved wire 802. Subsequently (or simultaneously with or prior to the radial retraction of the fingers 4), the ring prosthesis can be pushed down in the distal direction D by means of the fingers 855 in order to drive the pins 801 (or 444) into tissue, such as valve annulus tissue). Once the ring prosthesis is attached to the tissue, the instrument 700 can be retracted in the proximal direction, as shown in FIG. 8C.

In the case of a ring prosthesis according to FIG. 9, the pins 444, from the time that they come free from the outsides 108 of the fingers 4, if the pins 444 are pre-tensioned for this purpose, will, corresponding to arrow Z (FIG. 8C) pivot inwards over a shorter or longer distance. The inwardly-pivoted condition can be seen in FIG. 9B (and FIG. 8C, to the left of the dashed-line pin 444). The anchoring in the tissue is thus improved and the risk of the ring prosthesis coming loose from that tissue is reduced. In order to prevent the pins 444 from prematurely pivoting inwards here, the fingers 4 will possibly be retracted radially only after the ring prosthesis has been attached in the tissue.

FIG. 10 shows a medical instrument 900 according to an eighth embodiment of the first aspect. This medical instrument 900 is, in particular, suitable as an applicator for a ring prosthesis 1000 according to a further aspect of this application. Further details of this ring prosthesis can be found in FIG. 11, which shows a second design of the ring prosthesis according to the second aspect. With reference to the previously described embodiments of a medical instrument according to the first aspect, corresponding items are again denoted here with corresponding reference numbers and symbols. From the eighth embodiment according to FIG. 10, only a distal part of the medical instrument is in turn shown. The proximal part which is not shown may be designed in the same manner as in the embodiment according to FIGS. 1 and 2.

The applicator 900 is designed in virtually the same way as the applicator as shown in FIGS. 1 and 2. The difference lies in the shape of the fingers 904, which is different from that of the fingers 4 in FIGS. 1 and 2. The difference in shape is that the fingers 904 continue at 906 in a radial, outward direction, whereas the fingers 4 in FIGS. 1 and 2 continue there roughly parallel to the longitudinal centre line 3 to come to a point. The fingers 904 have a recess 905 at their free ends 6 in order to grip on a prosthesis, in this case the ring prosthesis 1000.

The ring prosthesis 1000 is formed, just as the ring prosthesis 800, from a wire 802 which has a waved pattern of wave troughs 803 and wave peaks 804. The ring prosthesis 1000 also has pins 801 for anchoring in tissue. However, in the case of the ring prosthesis, the pins 801 are attached to the wave troughs 803. This offers the advantage that, if the pins 801 are pricked into the annulus tissue of a valve, the remainder of the ring prosthesis 1000 will lie essentially outside the passage through which blood flows. The waved wire 802 may rest on the annulus. A further difference is that the ring prosthesis 1000 is provided with ring segments 806. In a first condition, adjacent ring segments 806 lie at a distance from one another. In a second condition with a smaller diameter, these ring segments 806 may lie with their ends against one another, thereby defining a minimum diameter for the ring prosthesis 1000. Thus, this ring prosthesis cannot further narrow beyond this minimum diameter. A completely different function of the ring segments is that they can serve to support a further prosthesis which is to be implanted in or near the ring prosthesis and/or to affix a further prosthesis of this type. The limiting function with regard to the minimum diameter may even be dispensed with in this support/attachment function, or the ring segments do not in fact have to be provided in such a way that they can form an essentially closed second ring. It is noted that the ring segments are optional in the case of the ring prosthesis, and may therefore also be absent, and that, if required, ring segments 806 of this type may also be provided in the ring prosthesis 800.

Just as in the ring prosthesis 800, the pins 801 can pivot inwards over a shorter or long distance. However, it is noted that in both the ring prosthesis 800 and the ring prosthesis 1000, the pins 801 can also pivot or bend in a different direction in order to improve the anchoring in surrounding tissue. A different direction of this type may, for example, be in a radially outward direction and/or in a tangential direction. Adjacent pins can also bend towards one another in both the ring prosthesis 800 and the ring prosthesis 1000 in order to form a clamp together.

Returning to FIG. 10, it can be seen that the applicator 900 can hold the ring prosthesis in place when the latter has a larger diameter, as shown in FIG. 10a, as well as when the latter has a smaller diameter. This diameter change can be imposed in a forced manner with the aid of the applicator 900 by displacing the fingers from the position shown in FIG. 10a to the position shown in FIG. 10b or vice versa by displacing the fingers from the position shown in FIG. 10b to the position shown in FIG. 10a. The waved wire 802 makes it possible for the ring prosthesis to vary in diameter here. Thus, it is possible, for example, to deliver the ring prosthesis with a smaller diameter (FIG. 10b) to the intervention location and to increase it in diameter there before attaching it to surrounding tissue. Separately herefrom or in addition hereto, the applicator 1000 can also be used, after the ring prosthesis 1000 has been attached to the surrounding tissue, to force it to be reduced in diameter. After the ring prosthesis has been attached to the surrounding tissue and has possibly been reduced in diameter by means of the applicator 1000, the ring prosthesis 900 can be detached by retracting the applicator in the proximal direction P.

Figure 12A:
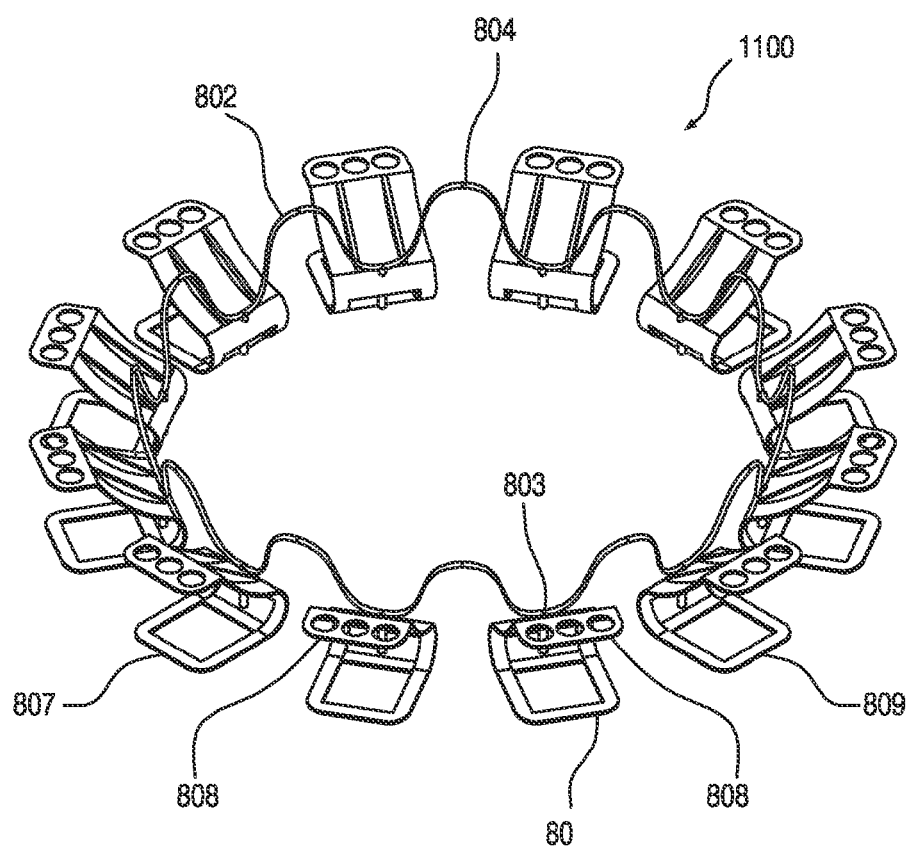
FIG. 12a shows a view obliquely from above and FIG. 12b shows a view of the side edge of the ring (with the so-called clamping mouths in FIG. 12b substantially schematized)
Figure 12B:
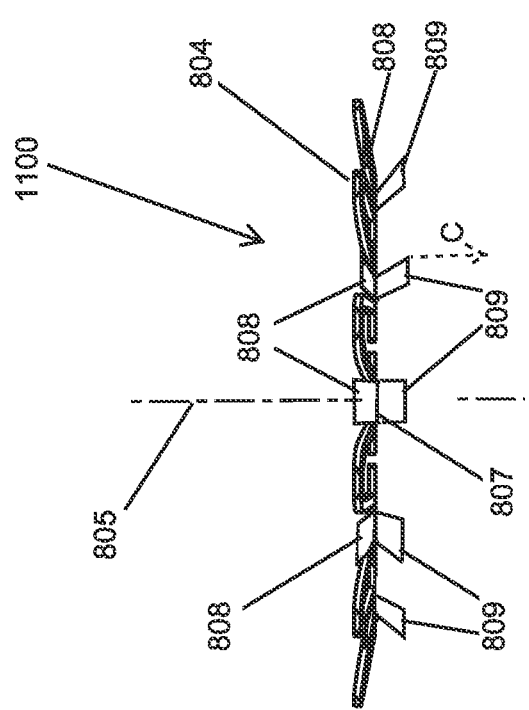

FIG. 12 shows a third design of a ring prosthesis 1100 according to the second aspect. FIG. 12A shows the ring prosthesis 1100 in a perspective view from above with the clamping mouths (to be discussed below) shown in the closed position and FIG. 12B in a perspective view from the side edge with the clamping mouths 807 (to be discussed below), shown in schematized form, in a similarly closed position. This ring prosthesis 1100 differs from the ring prostheses 800 and 1000 in that the anchoring elements are clamping mouths 807 rather than pins 801. Each clamping mouth 807 comprises a first jaw part 808 and a second jaw part 809 which is movable in relation to the first jaw part 808. In this design, the first jaw part 808 is immovable, and extends essentially parallel to the surface defined by the waved pattern. The second jaw part 809 is shown in the more or less completely closed position, but is movable under the influence of a temperature treatment so that it can extend in the direction of the arrow C, in the direction of the longitudinal axis across the ring, in order to attain an opened position. In the shown closed position, the second jaw part 809 is tilted towards the first jaw part 808—the condition shown—in order to clamp tissue between the first jaw part and the second jaw part. If the tissue to be clamped is thinner, the clamping mouths will close even further than shown in FIG. 12. The clamping mouths 807 are attached to the wave troughs 803 of the waved wire 802. Furthermore, the clamping mouths 807 are made from a memory material, such as a previously mentioned memory plastic or a previously mentioned memory metal. In the design shown, the clamping mouths are made from nitinol and, in FIG. 12a, are in the virtually closed condition. In the event of further heating and exceeding of a threshold temperature, the second jaw parts 809 will then tilt, under the influence of a pre-tension, even further towards the first jaw parts 808.

FIG. 12 shows the clamping mouths 807 as attached to the wave troughs. If required, the clamping mouths can also be attached to the wave peaks. It is furthermore noted that, instead of both jaw parts 808 and 809 being movable, it is also very readily possible for only the jaw parts 808 or only the jaw parts 809 to be movable, while the other jaw parts 809 and 808 respectively are immovable. Furthermore, the clamping mouths may, if required, be provided with teeth for better anchoring in the tissue to be clamped in the clamping mouths. Furthermore, an open structure of the clamping mouths, as can be seen in case of the clamping mouths 809 in FIG. 12a, can also contribute to an improved anchoring in the tissue to be clamped.

Figure 13A:
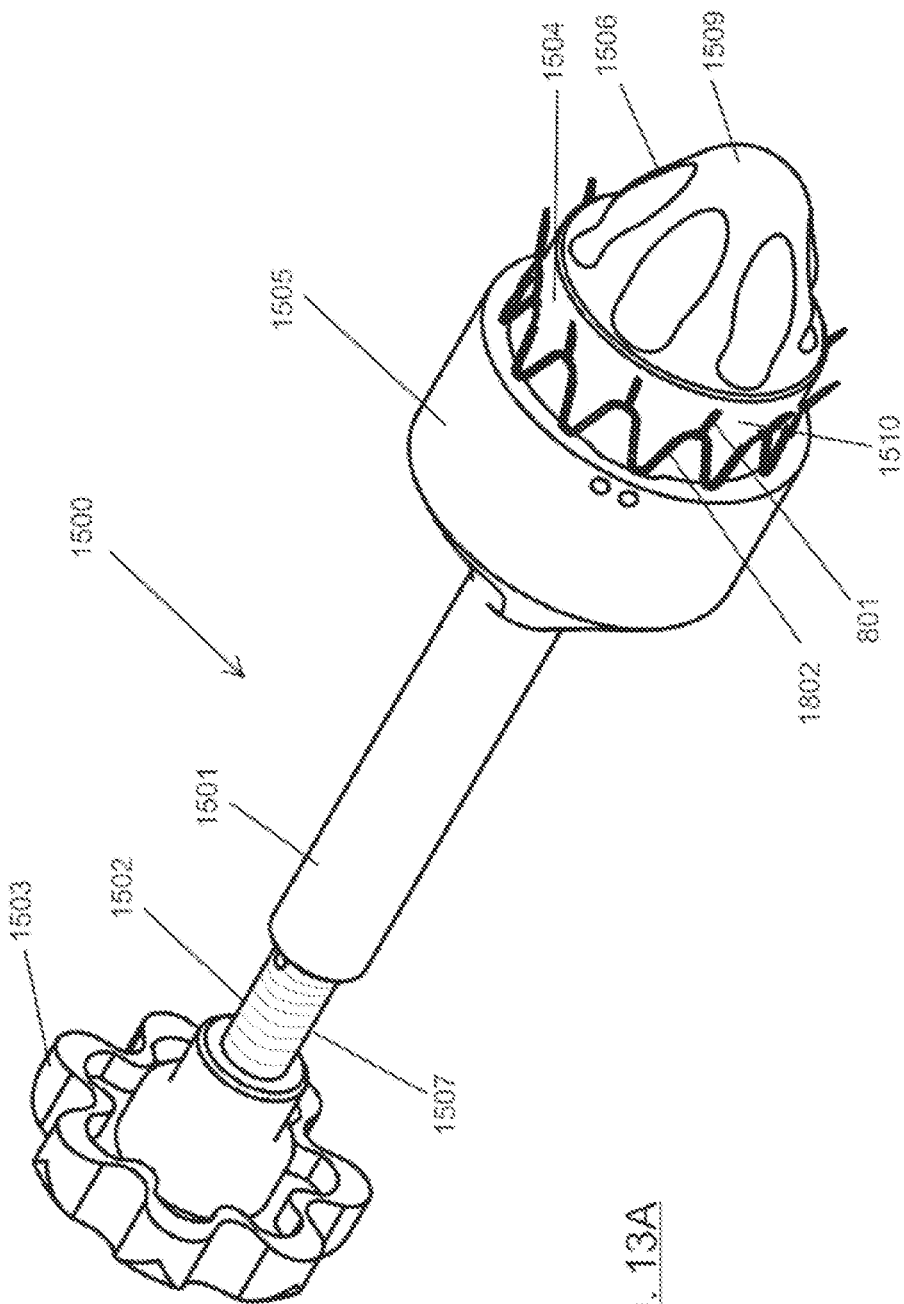
FIG. 13a shows a perspective view and FIG. 13b shows a longitudinal section view of the distal part of this applicator.
Figure 13B:
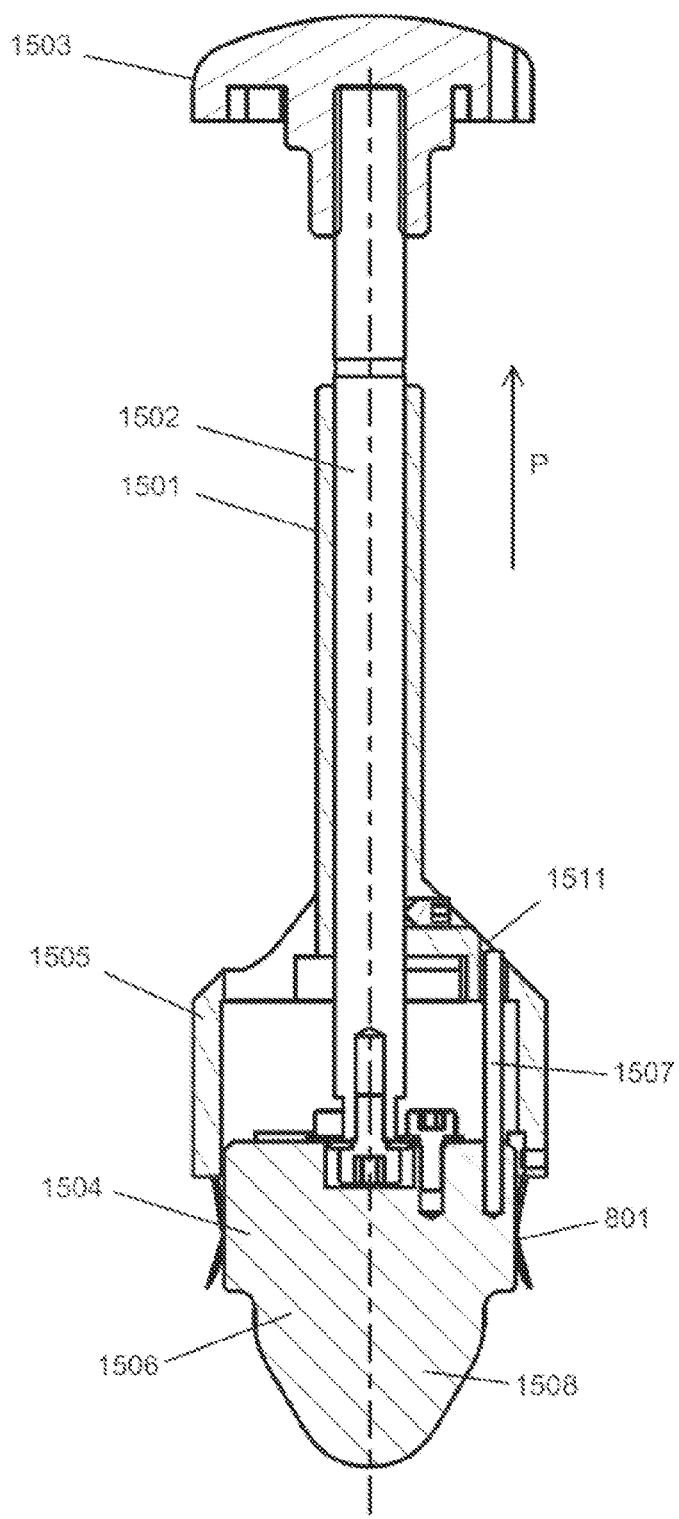

FIG. 13 shows an applicator 1500 according to the fifth aspect of this application. This applicator 1500 is essentially constructed from four components, i.e. a tube 1501, a pin 1502, a sheathing 1505 and a carrier 1504. The pin 1502 is provided with an outer screw thread 1507. This screw thread may extend over the entire length of the pin, but it generally suffices if this outer screw thread extends over only a part of the length. In order to be able to rotate the pin 1502 with ease, said pin is provided on the proximal end with an operating button 1503 which is connected in a rotation-resistant manner to the pin. The pin 1502 projects into the tube 1501 and extends through the entirety of this tube so that it projects from the tube 1501 at both the proximal end and the distal end. The carrier 1504 is attached to the pin at the distal end of the pin 1502. Here, the carrier 1504 is rotatable in relation to the pin 1502 around the longitudinal centre line 1508 of the pin, so that, if the pin is rotated by means of the operating button 1503, the carrier can be prevented from rotating with it.

The tube 1501 is provided at a given location with an inner screw thread which mates with the outer screw thread 1507. It can thus be achieved that, when the pin 1502 rotates in relation to the tube 1501, the tube and the pin move in an axial direction in relation to one another. The tube 1501 is provided with a sheathing 1505 on the distal end. This sheathing is attached to the tube 1501. This may be a rotation-resistant attachment, but an attachment rotatable around the longitudinal centre line 1508 is possibly also conceivable. When the pin 1502 is rotated—in the correct direction—in relation to the tube 1501, the carrier 1504 will slide inwards into the sheathing in the proximal direction P. Here, the axial guide 1507 prevents the carrier 1504 from rotating in relation to the sheathing 1505. The axial guide is designed here as a pin 1507 which is shiftable through the bore 1511. However, this can also be done differently, for example by means of a rib on the inside of the sheathing which grips into a slot in the outside of the carrier 1504.

The carrier 1504 has a carrier surface 1510 facing radially outwards, on which the prosthesis can be attached. Here, a ring prosthesis is shown which is very similar to the ring prosthesis as shown in FIG. 8c. The main difference is that, in FIG. 8c, the wave-shaped pattern is roughly radially oriented, whereas the wave pattern in FIG. 13 is almost completely axially oriented. The ring prosthesis with the waved wire 802 and pins 801 is clamped here on the carrier surface 1510.

As shown in FIGS. 13a and b, the outer contour of the carrier surface 1510 is essentially the same as the inner contour of the sheathing 1505, so that the carrier surface can be accommodated more or less without play in the sheathing.

If the carrier 1504 then slides inwards into the sheathing 1505, the prosthesis 801, the prosthesis 802 slides away from the carrier in the distal direction.

In order to be able to insert the applicator easily through channels or passages in the patient, the carrier is provided on the distal end with a nose part 1506 with a rounded point 1509.

The ring prosthesis according to the second aspect can be used for more applications than only the constriction of a dilated valve. Examples of such other applications are:

- The ring prosthesis according to the second aspect can be integrated with a valve prosthesis comprising valve flaps. The ring prosthesis can then draw the tissue from around the outside against the valve prosthesis in order thereby to prevent leakage outside along the valve prosthesis.
- The ring prosthesis according to the second aspect can be used as a support and/or mounting point for a valve prosthesis comprising valve flaps. The ring prosthesis will then first be implanted, followed by the valve prosthesis comprising valve flaps. According to the second aspect, this application therefore also relates to a method for carrying out a heart valve repair, wherein a ring prosthesis according to the second aspect is first implanted and thereafter a valve prosthesis is attached to the implanted ring prosthesis. In a step preceding these two steps, the old, diseased heart valve can first be removed if it had not yet been removed.
- The ring prosthesis according to the second aspect is also usable as a closing system for closing an access port made in a human or animal organ. When carrying out an intervention on the heart, the surgeon may, for example, make an access port through the heart wall. This is done, inter alia, at the apex. This access port must be closed once more in order to prevent leakage from the heart. This can be done by implanting a ring prosthesis according to the second aspect around the port made in the heart wall (such as at the apex) and then reducing the ring prosthesis in diameter. The tissue is then drawn inwards and the port is closed. The tightly drawn tissue can then usually expand once more to result in a complete seal.

FIG. 14 shows a medical instrument 1200 according to a ninth embodiment of the first aspect. This medical instrument 1200 is suitable in particular for cutting away surrounding material or for punching a passage. FIG. 14 shows a double-headed design with a distal head 1202 and a proximal head 1201. The distal head 1202 is designed on the additional cutting means 1205, 1206 in the same way as the head from FIGS. 1 and 2. The proximal head 1201 is designed as the mirror image of the distal head 1202, on the understanding that the additional cutting means 1203, 1204, are designed differently. With reference to the previously described embodiments of medical instruments according to the first aspect, corresponding items are again denoted here with corresponding reference numbers and symbols. From the ninth embodiment according to FIG. 14, only a distal part of the medical instrument is in turn shown. The proximal part which is not illustrated may be designed in a manner comparable to the embodiment according to FIGS. 1 and 2 or FIGS. 5 and 6.

The proximal head 1201 with the second plurality of fingers 94 carries a cutting element 1203. The cutting element 1203 is designed as a cylindrical part which is variable in diameter in order to be able to expand from the position shown in FIG. 14a to the position shown in FIG. 14b if the second plurality of fingers 94 are spread. The cutting element 1203 is designed in particular to be stretchable, such as elastically stretchable, in order to allow this expansion. This example can also be implemented by designing the cutting element 1203 as a spiral-type knife, formed, for example, from a plate material bent into a spiral-type configuration. A spiral-type knife of this type will have two overlapping ends, viewed in the circumferential direction. In the case of a smaller diameter, the overlap of the end parts will be greater than in the case of a larger diameter. The cutting element 1203 has a cutting edge 1204, with which it can cut into tissue. This cutting can be done by rotating the medical instrument 1200 around its longitudinal centre line 3 and/or, in the manner of punching, by displacing the cutting organ 1203 in the distal direction D in relation to the material to be cut. The cutting element 1203 is suitable, inter alia, for creating or widening passages through a vascular wall or through other tissue, but can also be used to remove deposits or bulges on the inside of a vascular wall or organ, or to cut into or remove a diseased heart valve. In the condition shown in FIG. 14a, the cutting element 1203 lies, as it were, sunk into the medical instrument 1200, so that it cannot damage surrounding tissue. At the intervention location, the third rod 91 can be displaced in the distal direction in relation to the first rod 1 which is designed as a tube in order to spread the fingers from the condition shown in FIG. 14a to the condition shown in FIG. 14b.

In the case of the distal head 1202, each finger 4 is provided with a cutting edge 1205 on the radial outside. This cutting edge optionally ends at the free finger ends 6 in a sharp end 1206, in particular a sharp point. Viewed from the free finger end 6, the cutting edge extends over the entire area 1207 or a part thereof. The fingers 4 may also optionally have a cutting edge 1208 on the radial inside 1208 which extends from the free finger end 6 over some distance in the direction of the finger end 5. In the condition shown in FIG. 14a, the cutting edges 1205 and sharp ends 1206 of the fingers 4 lie sunk into the slotted element 34 or otherwise in the medical instrument 1200 so that it cannot damage surrounding tissue. At the intervention location, the second rod 2 can be displaced in the proximal direction in relation to the first rod 1, which is designed as a tube, in order to spread the fingers from the condition shown in FIG. 14a to the condition shown in FIG. 14b. The fingers 4 with cutting edges 1205 are usable to create or widen a passage in a vascular wall or other tissue. The fingers 4 with cutting edges are also usable to remove deposits or bulges on the inside of a vascular wall or organ, or to cut into a diseased heart valve so that it can be removed more easily.

To illustrate different designs, the medical instrument 1200 is shown with differently designed heads 1201 and 1202. It will thus be clear that, in the case of a double-headed design, the distal head 1202 and the proximal head 1201 can both be designed in the same way, for example both with a cutting element 1203 or both with cutting edges 1205 on the fingers. The advantage of a double-headed design is that tissue or other material can be cut simultaneously or non-simultaneously from two opposite sides. It is furthermore noted that both the cutting element 1203 and cutting edges 1205 can also be very readily used in the case of a single head. This may then be the proximal head 1201 or the distal head 1202. If only a proximal head 1201 is provided with cutting means (in the absence of a distal head), it is possible to form a passage through tissue which was entirely closed prior to the intervention.

With reference to the medical instrument 1200, it is noted that, if the proximal head 1201 and the distal head 1202, at least in particular the free finger ends of the fingers thereon, are placed closer to one another, the plurality of fingers on the one head can be used as an anvil which interworks with the plurality of fingers of the other head which are provided with cutting elements. Counter-pressure can then be applied during the cutting. The finger ends may thereby overlap one another to produce a pincer effect. The fingers on both heads may also be provided here with cutting elements.

With reference to the various medical instruments shown above according to the first aspect of the application, it will be clear that they could also be used to measure the diameter of a passage or to measure the pressure of and/or tension and/or tissue resilience in tissue surrounding a passage. By allowing the fingers to expand in a controlled manner by means of the operating button and by providing a graduated scale in the operating button, the rotation of the operating button is indicative of the width of the fingers. Pressure sensors may also be provided on the fingers in order to measure the resilience and/or pressure and/or tension of tissue surrounding the fingers. The design according to FIG. 14 is also usable for this purpose, possibly following removal of the cutting elements. Measurements can thus be carried out which are much more accurate than those carried out with conventional measurements, wherein use is made of a balloon or indirect measurement on the basis of a CT scan, echo and the like.

FIG. 15 shows a first design of the fourth aspect of this application. This first design relates to a prosthesis 1300 for the performance of an end-to-side (=ETS) anastomosis. This FIG. 15 is based on FIG. 10a from WO 00/24339, on the understanding that the figure has been modified to show the fourth aspect of the application. The modifications relating to the fourth concept will be discussed below. Further details and also variants of the design shown, which were also present in the design according to WO 00/24339 and are also applicable to the fourth aspect of this application can be found in this WO 00/24339. Memory metal, such as nitinol, has the favourable property that it can be deformed from a first condition to a second condition, and can be fixed in this second condition. By exceeding or understepping a specific threshold temperature, the fixing can be undone, after which a reverse deformation from the second condition to the first condition takes place. However, restrictions apply to this deformation and reverse deformation. If memory metal, such as nitinol, is deformed with an abrupt transition, as in the case of a sharp crease, permanent deformations occur. As a result of these permanent deformations, the final condition remaining after reverse deformation differs from the original first condition. It is even possible that little or no deformation takes place. The memory then functions, so to speak, less effectively or not at all. To prevent this, it is customary to avoid sharp bends by using a concave shape, at the location of a sharp bend, so to speak in the axil thereof, which makes the bend much more gradual. In the case of 'prostheses of the previously defined tubular type', a sharp bend is often required in the axil, resulting in a concave cavity which reduces the clamping force required for anchoring to the tissue at the location of the axil. The fourth aspect of this application is also intended to offer a solution to this problem.

The prosthesis 1300 comprises a tubular element 1301 formed from memory material, in this case a nitinol alloy, with a distal flange 1320 and a proximal flange 1330. At 1312, a graft vessel 1310 is attached to the tubular element. This attachment may be carried out in the manner described in WO 00/24339, but can also be done in a different manner, such as through adhesion, and/or at a location other than at 1312.

The distal flange and proximal flange or both shown here in the radial position, in which they extend in a radially outward direction in relation to the tubular element. The distal flange 1320 is formed by a plurality of distal flange feet 1302, which are disposed in a distributed manner over the circumference of the tubular element 1301. The distal flange feet are releasable from an extended position indicated schematically with broken lines to tilt to the radial position (arrow E). In the radial position, the distal flange feet, together with the proximal flange, around a passage formed in the receiving vessel, clamp the surrounding tissue 1311 of the wall of the receiving vessel.

The surrounding tissue 1311 of a receiving vessel in the case of an ETS anastomosis is usually quite thin. This is illustrated in FIG. 15 by showing the distal flange and the proximal flange in the radial position with an intermediate space between them. It will be clear that, in reality, the distal flange and proximal flange 1320 and 1330 must lie in the radial position against the tissue 1311 in order to clamp it.

By way of departure from the knowledge disclosed by WO 00/24339, the distal flange feet are provided at the ends thereof which are attached to the tubular element with a filling 1305. In the radial position, this filling results in an increased clamping force of the distal flange and proximal flange, in particular at the location of the filling 1305. As a secondary effect, the increased clamping force also results in an improved seal. According to a further design of the fourth aspect, the distal flange feet 1320 are provided with a concave-curved part 1304 which follows on from the ends of the distal flange feet attached to the tubular element. The filling 1305 is disposed here in the hollow side of the concave-curved part 1304 facing towards the proximal flange. The distal flange feet can optionally have a straight part 1306 which connects the concave-curved part 1304 to the free end of the distal flange feet.

As described in WO 00/24339, it is very readily possible in the case of an ETS anastomosis to design the proximal flange 1330 as a fixed flange which is permanently in the radial position. According to the fourth aspect, a filling 1308 can be provided in this case also on the inside of the proximal flange, and the proximal flange can optionally be provided with a concave-curved part 1307. However, it is also very readily possible according to the fourth aspect of this application to design the proximal flange 1330 corresponding to the distal flange 1320 with proximal flange feet 1303 which, corresponding to the distal flange feet 1302, can tilt from an extended position to a radial position, and which, corresponding to the distal flange feet, are provided with a filling 1308 which may optionally be housed in the cavity of a concave-curved part 1307, and which may optionally have a straight part 1309.

It is noted that the principle of the filling, according to the fourth aspect of this application, is applicable to essentially all designs as described and shown in WO 00/24339. For this reason, this WO 00/24339 is deemed to be included in full in this application.

FIG. 16 shows a second design of the fourth aspect of this application. This second design relates to a prosthesis 1400 for attaching a heart prosthesis to surrounding tissue, such as a valve annulus. This FIG. 16 is based on FIG. 2 from WO 00/44311, on the understanding that the figure has been modified to show the fourth aspect of the application. The modifications relating to the fourth concept will be discussed below. Further details and also variants of the design shown in FIG. 16, which were also present in the design according to WO 00/44311 and are also applicable to the fourth aspect of this application, can be found in this WO 00/44311.

The prosthesis 1400 comprises a tubular element 1401 formed from memory material, in this case a nitinol alloy, with a distal flange 1420 and a proximal flange 1430. According to the fourth aspect, a valve prosthesis with a heart valve can be attached, if required, to the tubular element 1401. This can be done in many different ways already known from WO 00/44311.

The distal flange and proximal flange are both shown here in FIG. 16b in the radial position, in which they extend in a radially outward direction in relation to the tubular element 1401. The distal flange 4020 is formed by a plurality of distal flange feet 1402, which are disposed in a distributed manner over the circumference of the tubular element 1401 with intermediate spaces 1415 between them. The proximal flange 1430 is similarly formed by a plurality of proximal flange feet 1403, which are disposed in a distributed manner over the circumference of the tubular element 1401 with intermediate spaces 1416 between them. The distal and proximal flange feet 1402, 1403 are releasable from the extended position shown in FIG. 16a to tilt to the radial position (Arrow E). In the radial position, the distal flange feet 1402, together with the proximal flange feet 1403, clamp firmly on a valve annulus 1411.

By way of departure from the knowledge disclosed in WO 00/44311, the distal flange feet 1402 and proximal flange feet 1403 are provided at the ends thereof which are attached to the tubular element 1401 with a filling 1405 and 1408 respectively. In the radial position, these fillings result in an increased clamping force of the distal flange and proximal flange on the annulus 1411, in particular at the location of the fillings 1405 and 1408. As a secondary effect, the increased clamping force also results in an improved seal. According to a further design of the fourth aspect, the distal and proximal flange feet 1420 and 1430 are provided with a concave-curved part 1404 and 1407 respectively, which follows on from the ends of the distal and proximal flange feet attached to the tubular element 1401. The fillings 1405 and 1408 are disposed here in the hollow side of the concave-curved part 1404 and 4007 facing towards the proximal flange.

As described in WO 00/44311, it is very readily possible in the case of a prosthesis of this type to design the proximal flange 1430 as a fixed flange which is permanently in the radial position. In this case also, according to the fourth aspect, a filling 1408 can also be provided on the inside of the proximal flange.

It is noted that the principle of the filling, according to the fourth aspect of this application, is essentially applicable to all designs as described and shown in WO 00/44311, in particular sections 1.1, 2.1, 3.1, 4.1 and associated FIGS. 1-14. For this reason, the sections 1.1, 2.1, 3.1, 4.1 and associated FIGS. 1-14 of this WO 00/44311 are deemed to be included in their entirety in this application.

Figure 17:
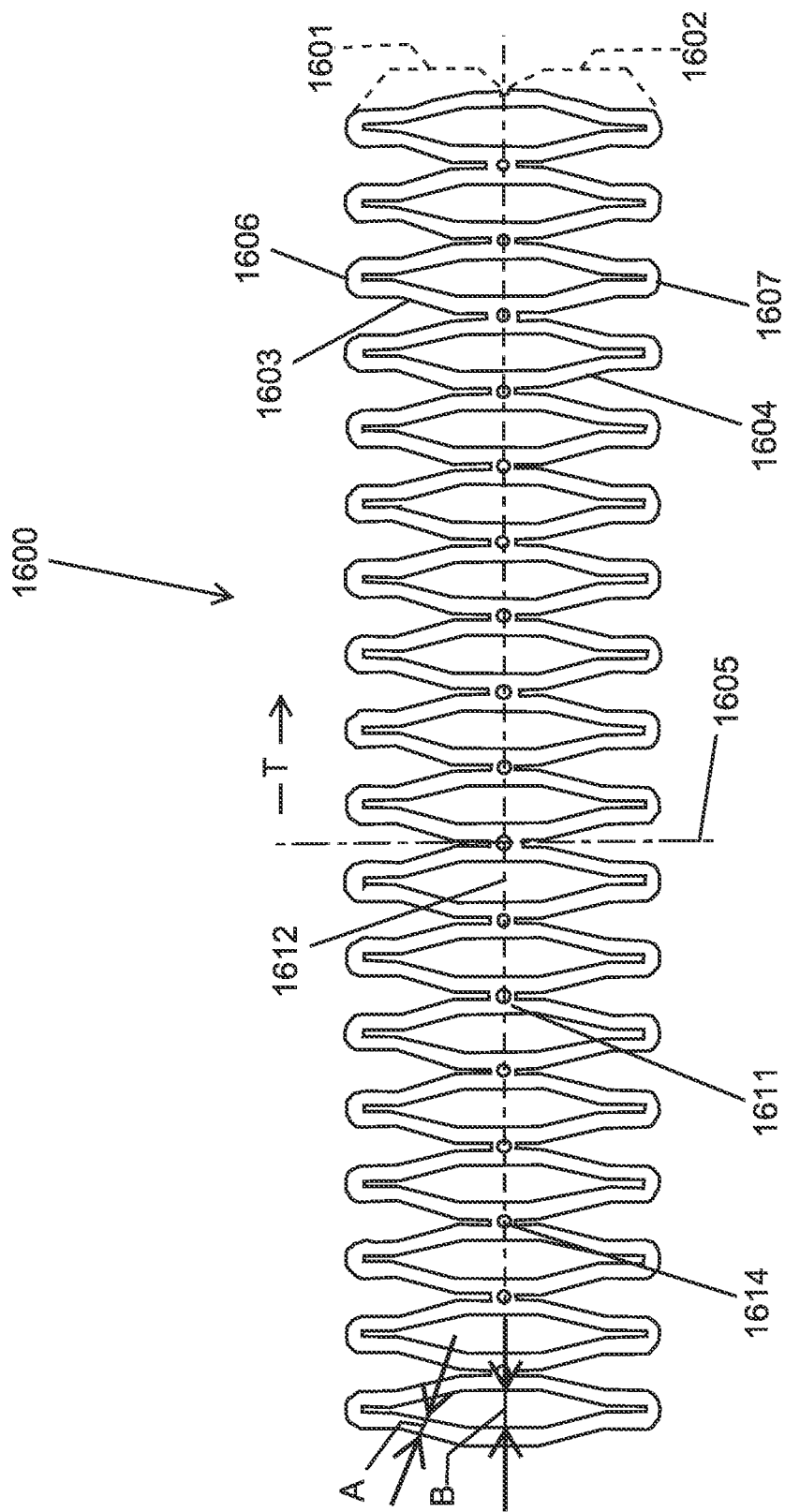
FIG. 17 shows an opened, flatly laid out view of a ring structure according to the sixth aspect.
Figure 18:
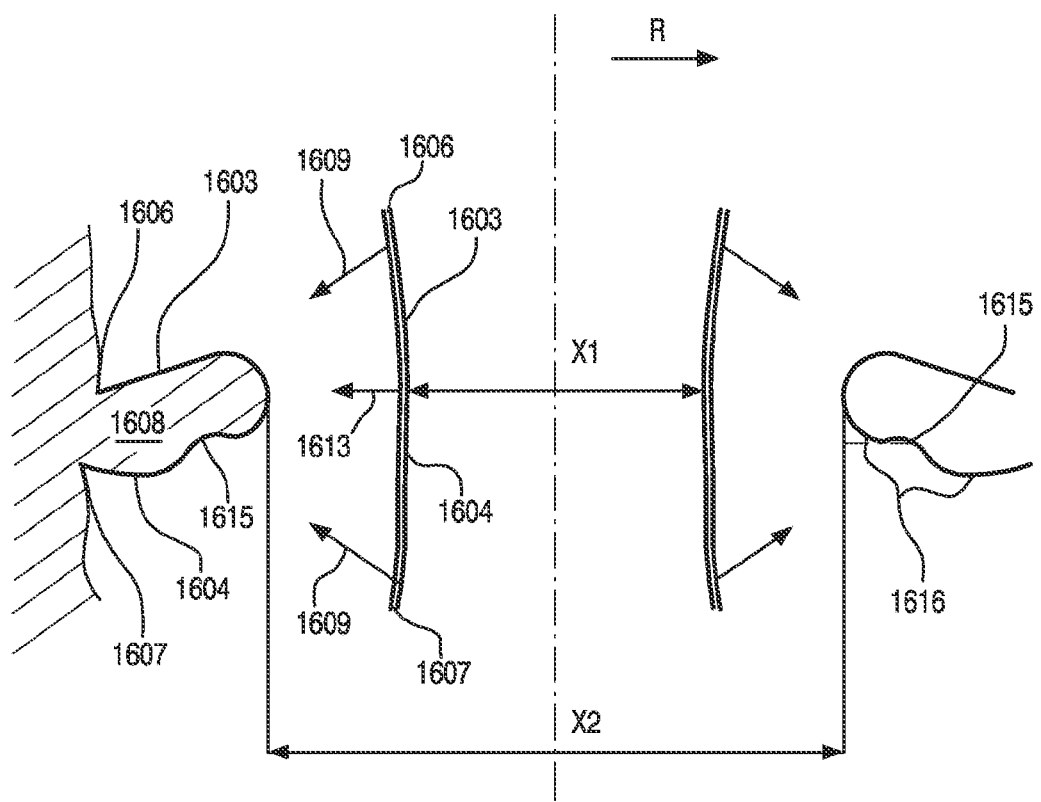
FIG. 18 shows a schematic side view in cross-section of the ring structure shown in FIG. 17, wherein the ring structure is shown in both the contracted position and in the expanded position.
Figure 19:
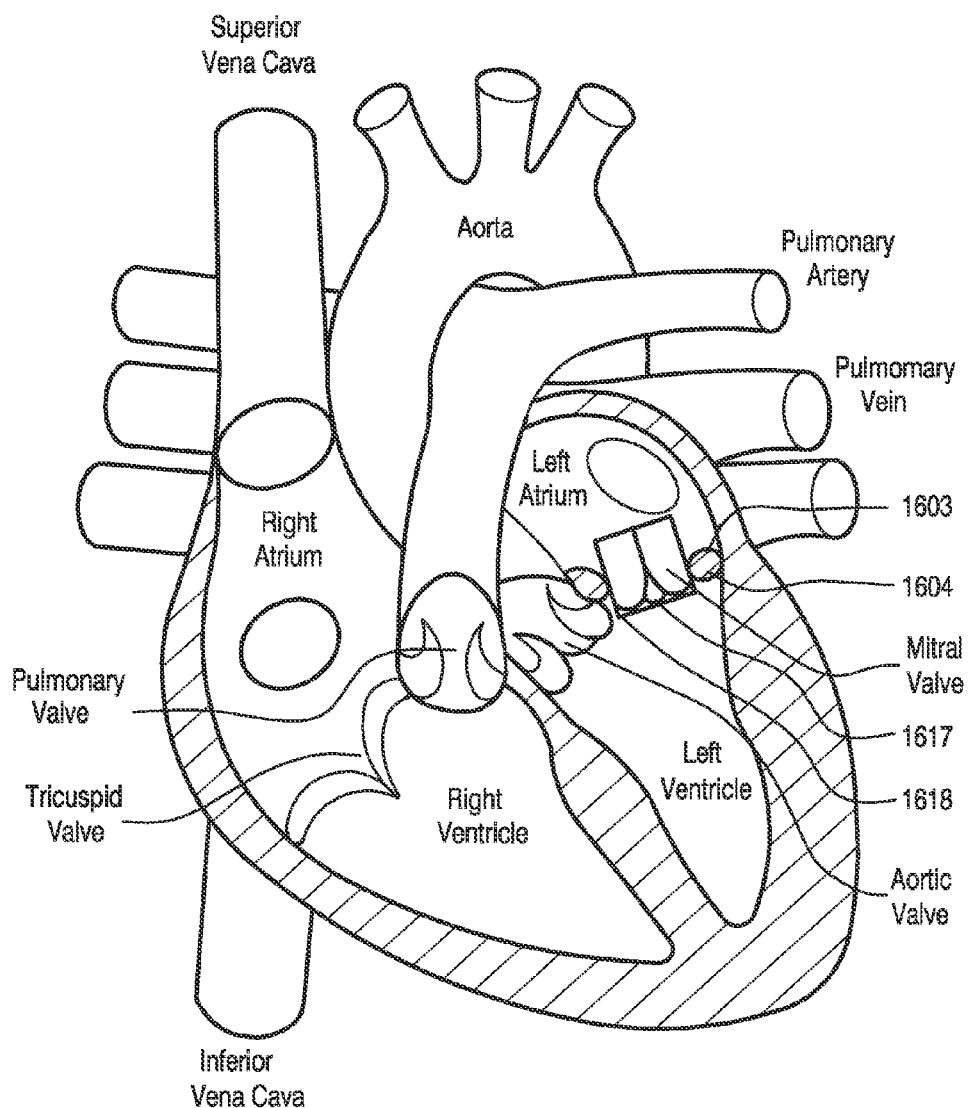
FIG. 19 shows a schematic cross-section view of the heart, with an assembly of a ring structure and a valve stent implanted therein in the mitral valve position.

FIGS. 17, 18 and 19 show a ring structure (1600) according to the sixth aspect of this application.

FIG. 17 shows the ring structure in an opened, flatly laid out view. Here, the ring shape can be obtained by attaching the left end and the right end of the illustration to one another and by forming the structure flatly laid out in the illustration into a ring.

The ring structure has an axial direction represented by the axial centre line 1605 and a radial direction R disposed across it (FIG. 18). The ring structure is constructed from a series of elongated loops 1610, the longitudinal direction of which extends in FIG. 17 in the axial direction, and the lateral direction of which extends in the tangential direction T (circumferential direction) of the ring structure 1600.

Adjacent loops 1610 are connected roughly at the midpoint of the long sides of the loop in each case via a junction 1611 to the respective adjacent loop. The imaginary centre line 1612 which interconnects these junctions forms a ring and divides each loop globally into a first half 1601 and a second half 1602.

The first half 1601 of each loop in each case forms a proximal flange foot and the second half 1602 of each loop in each case forms a distal flange foot. These flange feet are shown in FIG. 17 in the so-called extended condition, i.e. the condition in which they are oriented primarily in an axial direction. As shown in FIG. 18, in the non-expanded condition with diameter X1, the free ends 1606 and 1607 of the flange feet point, in the extended position, in the axial direction, but the flange feet 1603 and 1604 do not have to run purely axially in the extended position.

The proximal flange feet 1603 and the distal flange feet can bend outwards from the extended condition to a radial position. In the radial position, the free ends 1606 and 1607 of the flange feet point in the radial direction R. This outward bending occurs automatically, since the flange feet have been pre-tensioned for this purpose with a force (represented by curved arrows 1609 in FIG. 18) which is inclined to bend these flange feet to the radial position. This pre-tension may be a frozen temporary condition of a memory material. The ring structure may be made from a memory metal, such as a nitinol alloy, for this purpose. The pre-tension may also be a normal resilience (e.g. if the ring structure is made from a spring-steel type of material). In this latter case, a mechanical obstacle, such as a sleeve or obstacle elements according to the seventh aspect, will be used to hold the flange feet stretched.

FIG. 17 shows the ring structure in an expanded condition. The loops are spread in the lateral direction in such a way that they have an inner width which in this case corresponds to 2× the thickness of the loop. It will thus be clear that by, as it were, closing the loops (making the inner width zero by pressing the longitudinal sides against one another), a circumferential reduction of 50% can be implemented.

FIG. 17 furthermore shows that each junction 1611 is provided with one (or more) radial bores 1614. By means of these radial bores, a stent, heart valve or other biological or otherwise prosthesis can be attached in the ring structure, for example simply by means of a suture.

FIG. 18 shows that the ring structure can be extended from a compressed condition with diameter X1, which may, for example, be 13.3 mm, to an expanded condition with diameter X2, which may, for example, be 26.6 mm. FIG. 18 furthermore shows that, after the expanded condition has first been reached, the flange feet 1603 and 1604 are bent to the radial position in order to clamp annulus tissue 1608 or other tissue between them. In order to improve the fixing near or on the annulus of the mitral or tricuspid valve, the flange feet 1604 (lowermost in FIG. 18) are provided with a bulge 1615. This bulge 1615 is located in the half 1616 of the relevant flange foot 1604 which follows on from the junction. This bulge 1615 is adapted to the natural anatomy of the mitral or tricuspid annulus.

FIG. 18 furthermore shows by means of the arrow 1613 that the ring structure, if it is in the compressed condition, is under a radial pre-tension, which allows the expansion to occur automatically following release of the pre-tension. However, it is noted that it is also conversely possible for the ring structure to be under a radially inwardly directed pre-tension in the expanded condition. The ring structure is then usable, inter alia, as a constriction ring or as a sealing ring which draws the surrounding tissue inwards to provide a seal against a prosthesis implanted therein.

FIG. 19 shows, as an example, a use of the ring structure 1600 as a fixing means for the fixing on the annulus of a mitral valve of a stent 1618 with a heart valve 1617 of biological material, a so-called valved stent, therein.

Figure 20:
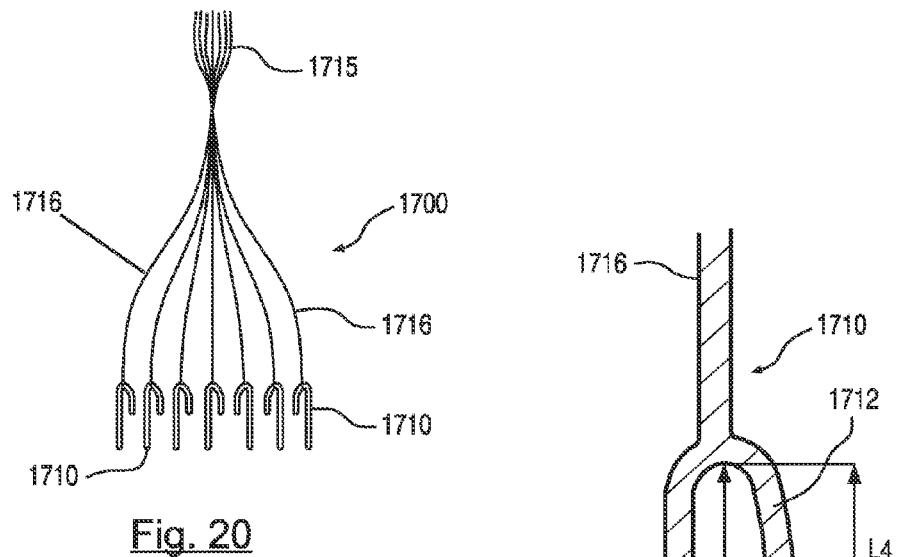
FIG. 20 shows a very schematic representation of a manipulator according to the eighth aspect for the release of a prosthesis.

FIG. 20 shows a manipulator 1700 according to the seventh aspect. This manipulator is intended for a prosthesis with distal and proximal flange feet, which are both to be brought into an extended axial condition in which they are under pre-tension which is inclined to bend these flange feet to a radial position. The proximal and distal flange feet are provided on a ring or tubular element 1720 (of which only a very small part is shown in FIG. 21). The manipulator according to the seventh aspect is able to hold these flange feet in the extended position and to release them so that they can bend to the radial position.

The manipulator 1700 is constructed from a plurality of U-shaped obstacle elements 1710 which are attached via cords 1716 to an operating element 1715. Each obstacle element has a first leg 1711 and a second leg 1712, the free ends 1713, 1714 of which point in the distal direction. The first leg 1711 has a first length L2 and the second leg 1712 has a fourth length L4.

Figures 21A, 21B:
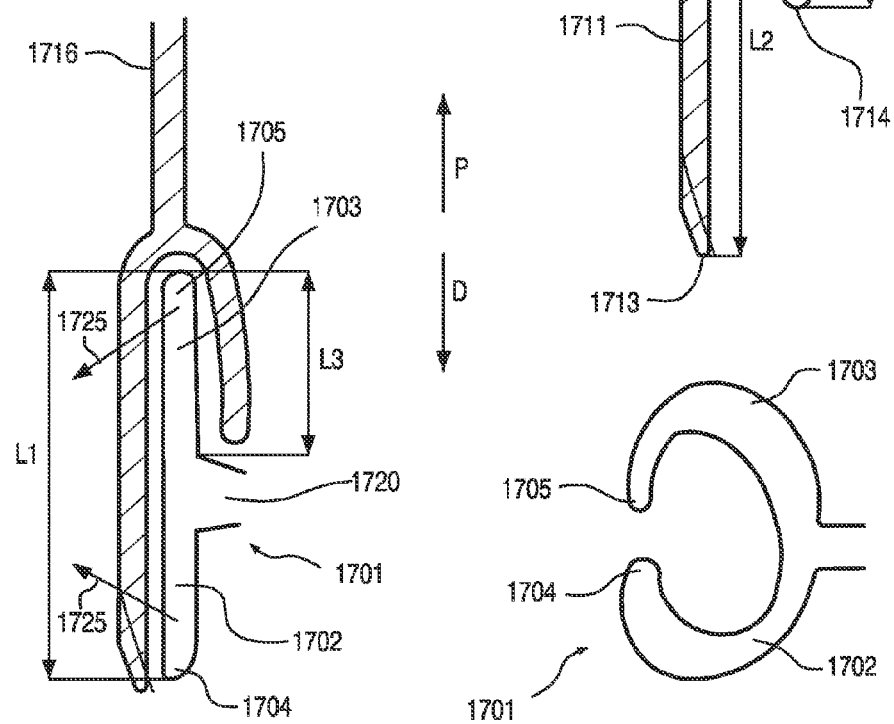
FIG. 21A shows the obstacle element in the condition in which a proximal and distal flange foot are held extended.
FIG. 21B shows the condition in which these flange feet have been released.

In the extended condition, the proximal flange feet 1703 have a third length L3. The distance between the free ends 1704 and 1705 of the proximal flange feet and the distal flange feet, in the extended condition of the flange feet, is L1. FIG. 21A shows that L2 is longer here than L1 and that L3 is shorter than L4. By taking L4 as slightly shorter than L3, the second leg 1712 can be prevented from touching a prosthesis mounted in the ring or tubular part 1720.

In FIG. 21A, the flange feet 1702 and 1703 are shown in the extended condition. The proximal flange foot extends into the cavity between the first leg 1711 and the second leg 1712. The first leg 1711 is longer than the second leg 1712. The first leg extends along the radial outside of the prosthesis 1701, so that it holds in place the flange feet 1702 and 1704, which, as a result of the pre-tension according to the arrows 1725, are inclined to bend outwards. The short leg 1712 thereby ensures that the long leg is not pushed aside. The proximal flange foot 1703 may, under the influence of the pre-tension, brace itself between the short leg 1712 and the long leg. This bracing may be sufficient to prevent the U-shaped obstacle elements 1712 from prematurely coming loose from the flange feet. If the prosthesis is at its intended location and the flange feet can be released, the manipulator is drawn away in the proximal direction P by means of the operating element 1715 which carries the obstacle elements 1710 along with it via the cords 1716. The flange feet then bend outwards, for example to the curved shape as shown in FIG. 21B.

Given that the cords 1716 are flexible, the obstacle elements 1710 can simply move along with the prosthesis if the latter is expanded or compressed. The release of the flange feet can therefore be implemented independently from the expansion condition of the prosthesis. The obstacle elements 1710 and/or the cords 1716 may furthermore be interconnected by means of further cords (not shown here) or otherwise, as long as the free mobility in the radial and axial direction of the obstacle elements is not thereby hindered.

Figure 22:
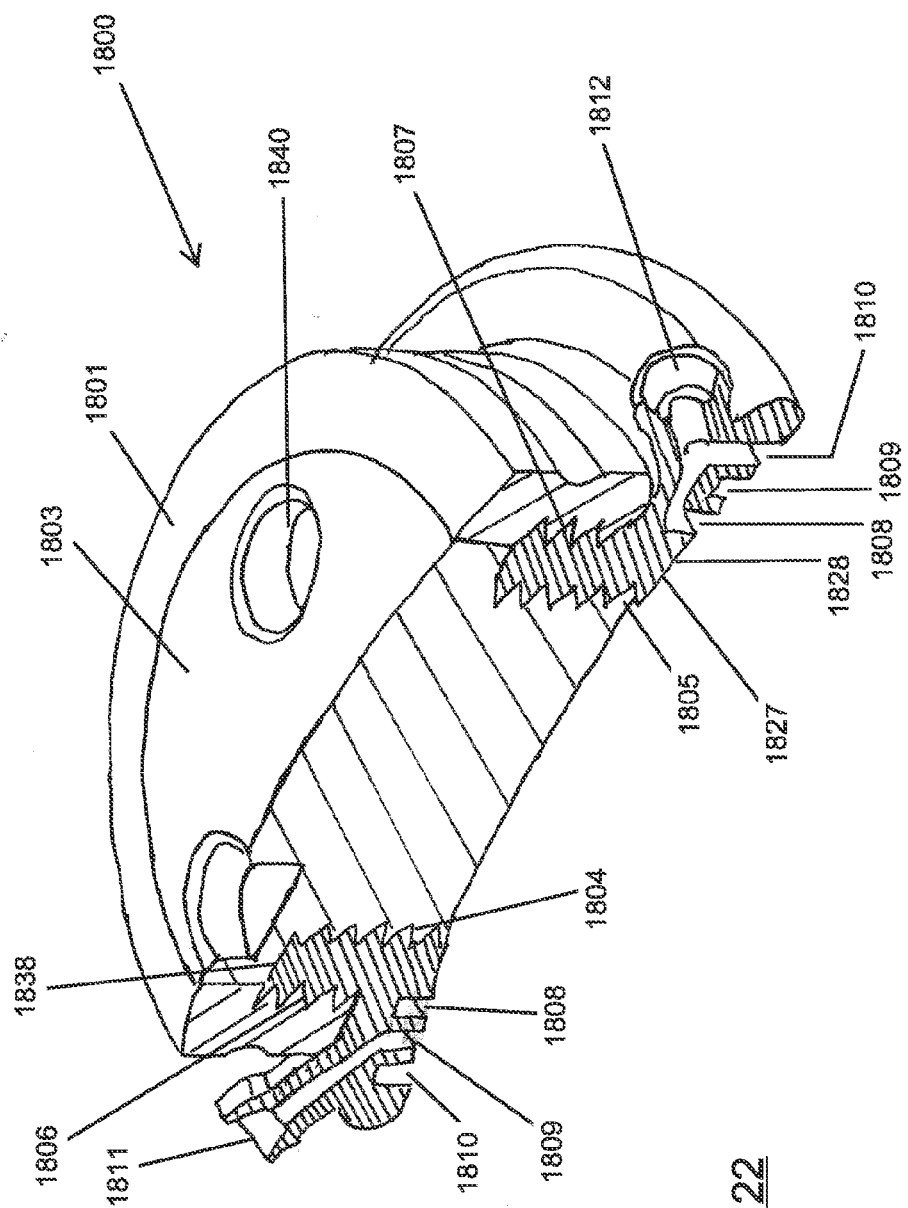
FIG. 22 shows a perspective view of a longitudinal section of a port assembly according to the eighth aspect.
Figure 23:
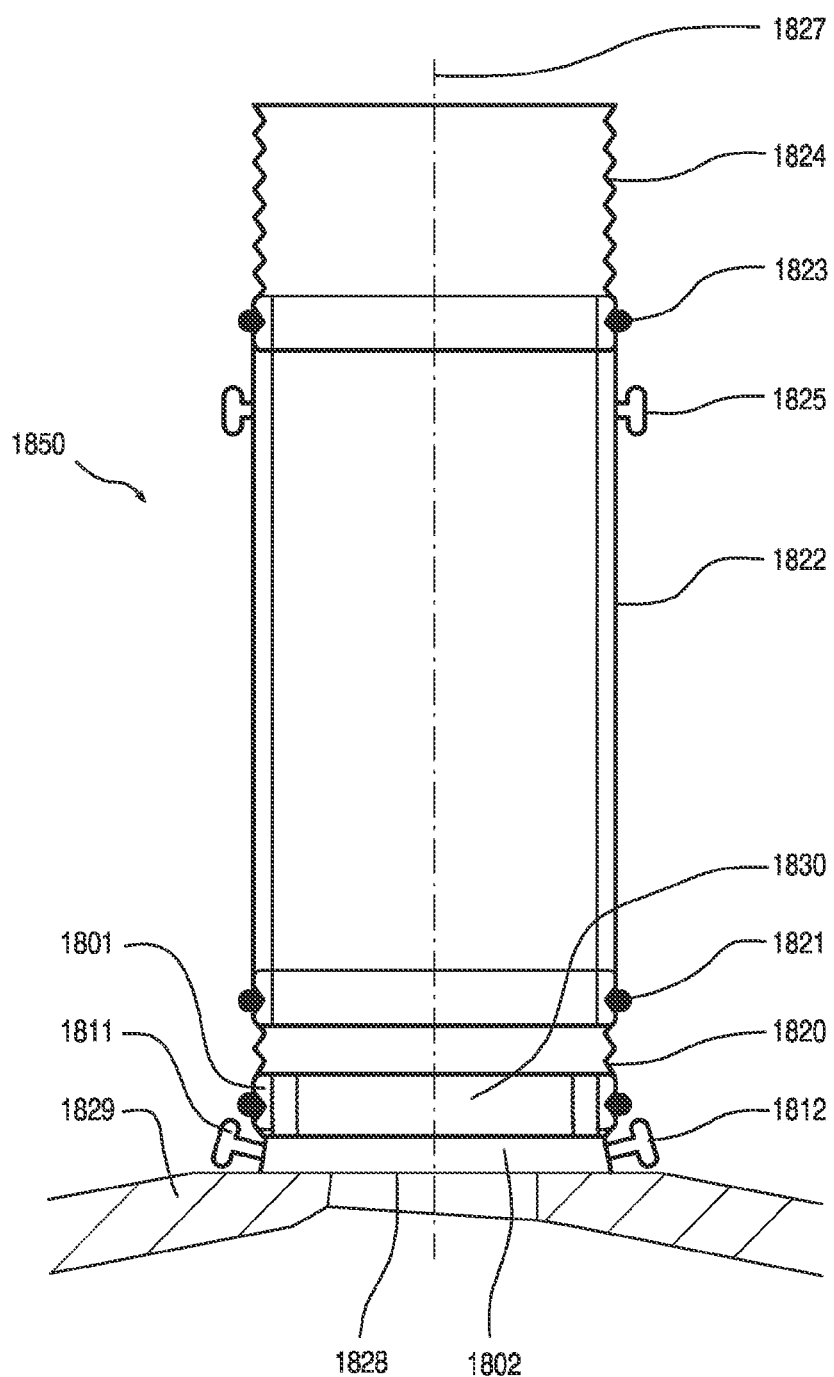
FIG. 23 shows a very schematic longitudinal section of a further port assembly according to the eighth aspect.

FIGS. 22 and 23 show port assemblies according to the eighth aspect.

FIG. 22 shows a first port assembly 1800. The first port assembly 1800 comprises a connector 1802 and a closing cap 1803. FIG. 22 furthermore shows the lowermost part of a work channel 1801 which can be attached to the connector.

The connector 1802 is provided with an inner screw thread 1804 and the cap is provided with an outer screw thread 1805, with which the cap can be screwed firmly into the connector. Recesses 1840 are provided in the top of the cap in order to grip hereon with a tool for rotating the cap.

The connector 1802 is furthermore provided with an outer screw thread 1807. A work channel 1801 provided with a mating inner screw thread 1806 can thus be attached to the connector.

The connector is provided on the second end 1828 with a crosswise surface with 3 concentric annular slots 1808, 1809 and 1810 therein, which extend completely around the port passage 1830. The inner slot 1810 and the outer slot 1808 are connected via a channel to a connection stub 1812, and the middlemost slot 1809 is separated from the inner and outer slot and opens out into its own connection stub 1811. The connection stub 1812 can be connected to a source for tissue adhesive, whereas the connection stub 1811 can be connected to a suction source in order to be able to generate a suction force in the slot 1809, or vice versa. The connector can thus be sucked firmly onto the wall 1829 of tissue and can be adhered firmly thereto by means of tissue adhesive and can be effectively sealed thereon.

A work channel 1820, 1822 is connectable to the first connector end 1838. The work channel has a stiff or stiffened channel part 1822 and a flexible channel part 1820. The flexible channel part 1820 is attached by means of the part 1801 to the connector and by means of the attachment 1821 to the stiff channel part 1822. The flexible channel part is shown here as a vascular prosthesis, but may equally consist of other flexible materials, such as, for example, rubber, silicone or plastics and other artificial materials, but also other curved or otherwise, hardened metal or plastic parts, which are reciprocally shiftable, twistable or rotatable. The stiff channel part is provided on its upper end with a closure 1824 which can close the work channel on the one hand and, on the other hand, can allow instruments herein. The closure may, for example, be a vascular prosthesis or hose which can easily be squeezed tight. The connections 1801, 1821, and 1823 are shown here as recesses over which a piece of vascular prosthesis is placed over which in turn a ligature or adhesion or ring or band or the like is placed, said last tying means not being shown here, but essentially any form of mechanical connection can be used. The work channel 1822 is furthermore provided with a connection 1825 and 1826. Gassing or degassing, for example, can be carried out via the one connection. Fluid can be fed in or out, for example, via the other connection. The connections 1825 and 1826 can also be used to guide instruments inside.

The connections 1825, 1826, 1811 and 1812 may, for example, be Luer connections.

The flexible channel part 1820 makes it possible, in a manner of speaking, to bend the longitudinal centre line 1827 of the work channel without bending the stiff channel part. The length of the stiff channel part will be more than 10× that of the flexible channel part.

Figure 24A:
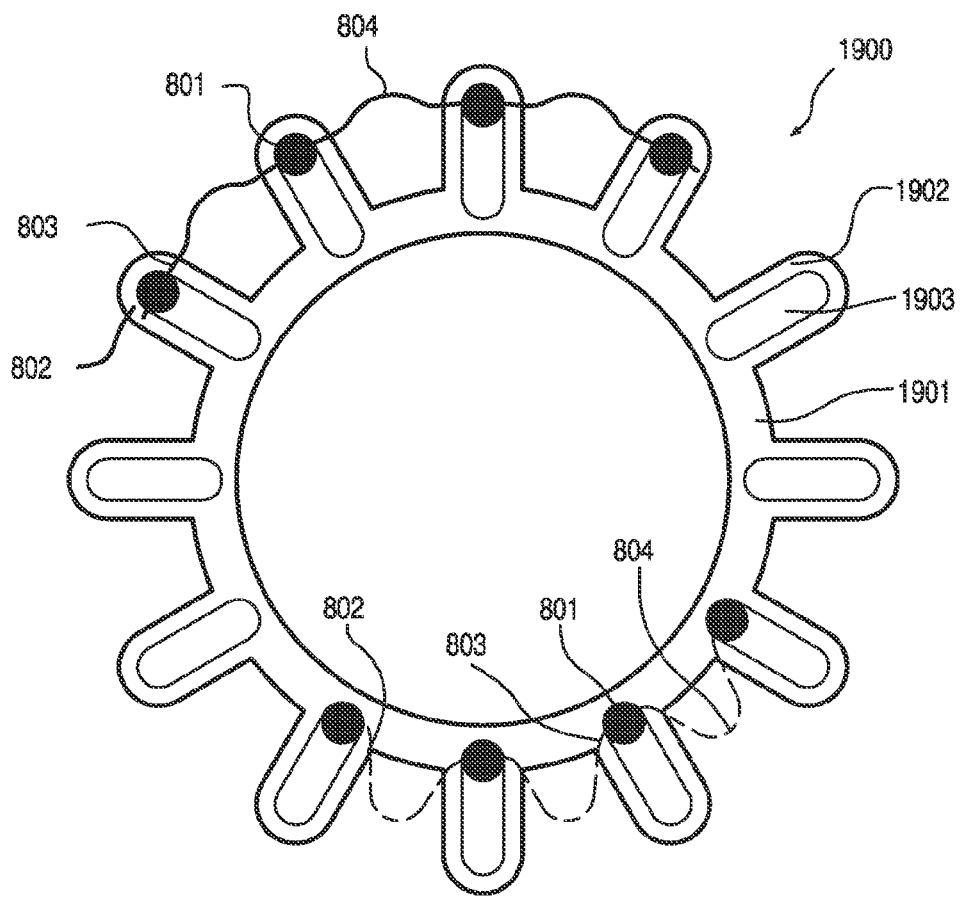
FIG. 24A shows a top view and FIG. 24B shows, as a detail, a cross-section view.
Figure 24B:
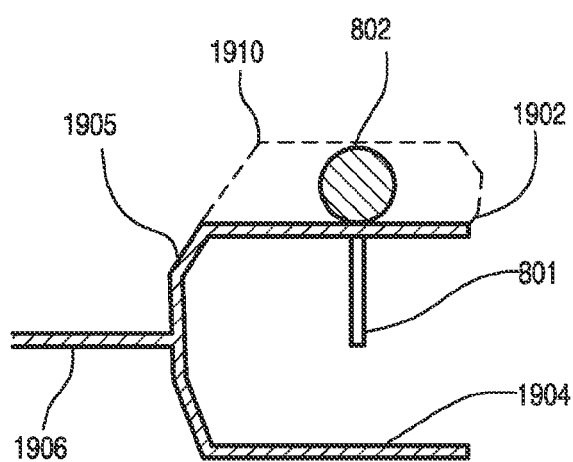

FIG. 24 shows very schematically an assembly 1900, for example for using the method according to the ninth aspect. FIG. 24A shows a top view and FIG. 24B shows, as a detail, a cross-section view, viewed in the tangential direction of the assembly.

This assembly comprises, on the one hand, a heart prosthesis, such as a heart valve prosthesis, the heart valve of which is shown very schematically with 1906 (FIG. 24B). The heart valve prosthesis comprises an annular or tubular edge part 1905, with uppermost flange feats 1902 and lowermost flange feet 1904. Annulus tissue can be clamped between these flange feet. This heart valve prosthesis may, in principle, be of any type, such as, inter alia, those known from the prior art. WO 00/44311 of the inventor, for example, can be cited as an example, which designates various suitable heart valve prostheses with movable lowermost and/or uppermost flange (feet). Although not necessary, radial slots 1903 are provided in the uppermost flange (possibly also in the lowermost flange).

The assembly for use of the ninth aspect furthermore comprises a ring prosthesis according to the second aspect of this application. This ring prosthesis is not shown in its entirety in FIG. 24A, but two ring sections of around 120° are shown. The one ring section, the wire of which is shown with unbroken lines, is in the expanded condition. The other ring section, the wire of which is shown by a broken line, is in the contracted condition. The ring prosthesis comprises a waved wire 802, with wave peaks 804, wave troughs 803 and pins 801. The pins 802 are shown here as attached to the wave troughs 803. However, the pins may also be attached to the wave peaks 804 or elsewhere between the wave troughs 803 and wave peaks 804.

The pins 801 of the ring prosthesis project through the radial slots 1903 and can move backwards and forwards through the slots in a radial direction. The implantation and attachment of the valve prosthesis can take place here prior to or simultaneously with the implantation of the ring prosthesis. However, the ring prosthesis may be integrated in advance with the valve prosthesis, and preferably with the upper flange thereof. This integration could comprise the attachment of the ring prosthesis to the proximal side or to the distal side of the upper flange, wherein, in the latter case, the pins of the ring prosthesis project through the radially positioned slots of the upper flange. It is also possible to design the upper flange as double-walled, as indicated schematically by means of broken lines 1910 in FIG. 24B. The ring prosthesis is then located between the two walls and the pins of the ring prosthesis project through radially positioned slots. It will be clear that a radial spring, which in each case pre-tensions a pin in a radially inward direction, can also very readily be inserted in the hollow space which is created in the case of a double-walled design. If the ring prosthesis is pre-tensioned in order to draw the pins in a radially inward direction, i.e. is pre-tensioned to reduce in diameter, the ring prosthesis then ensures that the tissue, such as the valve annulus, which is located between the lowermost flange 1904 and the uppermost flange 1902, is drawn in a radially inward direction. The tissue is thus drawn against the outside of the annular or tubular edge part 1905. The sealing of the tissue on the ring prosthesis can thus be improved and the bypass of blood outside along the valve prosthesis can be prevented. It will be clear that a different type of ring prosthesis with radially inwardly pre-tensioned pins is also possible. The ring prosthesis could, for example, comprise a fixed-diameter ring with springs radially mounted thereon and projecting outwards or inwards, which, on the other end, will be the pins which are oriented in an axial direction. It is also conceivable here to dispense with a separate ring and to attach the aforementioned springs directly to the outer flange or inner flange of the heart valve prosthesis. The assembly can thus be replaced with a heart valve prosthesis with at least one flange, said at least one flange being provided with radial slots, wherein pins, which are axially oriented and driven (pushed and/or pulled) radially inwards by means of a spring, project through the radial slots. Finally, it is noted that, wherever a spring is mentioned in this paragraph, this may also be a radially oriented zigzag wire made from a memory metal, such as nitinol, the pre-tension of which is released in the event of heating to above a threshold temperature.

The various designs of the nine aspects of this application can also be formulated in the clauses below:

1. Medical instrument, comprising:
   a first rod (1);
   a second rod (2) which extends along the first rod (1);
   a longitudinal centre line (3) defined by the direction in which the first rod (1) and the second rod (2) extend; and
   a manipulator;
   wherein the manipulator comprises at least a plurality of fingers (4; 94; 144), each with a first finger end (5) and a second finger end (6); wherein the second finger ends (6) are free ends (6);
   wherein the first finger ends (5) of this aforementioned plurality of fingers are supported on the second rod (2) in such a way that the fingers (4; 94; 144) of this aforementioned plurality of fingers, by moving the second rod (2) in relation to the first rod (1), are operable to be displaced from a first position to a second position; and
   wherein the distance from the free ends (6) of the fingers (4) to the longitudinal centre line (3) in the first position is different compared with the second position.

2. Medical instrument according to one of the preceding clauses, wherein the first rod (1) and the second rod (2) are movable in relation to one another in the longitudinal direction of the longitudinal centre line (3) for the aforementioned operation of the fingers (4; 94; 144).

3. Medical instrument according to one of the preceding clauses, wherein the first rod (1) and the second rod (2) are rotatable in relation to one another around the longitudinal centre line (3) for the aforementioned operation of the fingers (4; 94; 144).

4. Medical instrument according to one of the preceding clauses, wherein, in the second position or the first position, the distance from the free ends (6) of the fingers (4) to the second rod (2) is at most 90%, in particular at most 80%, such as at most 75% or at most 70%, of the distance from the free ends (6) of the fingers (4; 94; 144) to the second rod (2) in the other of these two positions.

5. Medical instrument according to one of the preceding clauses, wherein the plurality of fingers (4; 94; 144) is disposed in a distributed manner over the circumference of the longitudinal centre line (3).

6. Medical instrument according to one of the preceding clauses, wherein the free, second finger ends (6) are provided with a hook (60) with a hook opening (61) which opens in the direction of the first finger ends (5).

7. Medical instrument according to one of the preceding clauses, further comprising a tensioning system (62) acting on the fingers (4; 94; 144) in order to pre-tension the latter for displacement from the first position to the second position.

8. Medical instrument according to clause 7, wherein the tensioning system comprises a resilient element (62) provided in the circumferential direction of the instrument along the fingers.

9. Medical instrument according to one of the preceding clauses, wherein the distance from the free ends (6) of the fingers (4) to the longitudinal centre line (3) is greater in the first position than in the second position.

10. Medical instrument according to one of the preceding clauses 1-9, wherein the fingers (4; 94; 144) are movable from the first position to the second position and from the second position to a third position, wherein the distance from the free ends (6) of the fingers (4) to the longitudinal centre line (3) in the first position is greater than in the second position, and wherein the distance from the free ends (6) of the fingers (4) to the longitudinal centre line (3) in the third position is less than in the second position.

11. Medical instrument according to one of the preceding clauses, wherein the fingers (4) are attached at the first finger ends (5) in a pivotable manner via a pivot attachment (32, 33) to the second rod (2).

12. Medical instrument according to clause 11, wherein the distance from the pivot attachment (32, 33) of the first finger ends (5) to the longitudinal centre line (3) is unchanging.

13. Medical instrument according to one of the preceding clauses, wherein the pivot attachment comprises a hinge (32, 33).

14. Medical instrument according to clause 13, wherein the hinge comprises a convex part (32) and a corresponding concave receptacle (33) for the convex part (32).

15. Medical instrument according to clause 14, wherein the fingers (4; 94; 144) are in each case provided with an aforementioned concave receptacle (33).

16. Medical instrument according to one of the preceding clauses,
wherein each finger (4; 94; 144) further comprises an inner longitudinal side (7) facing towards the longitudinal centre line (3), and an outer longitudinal side (8) facing away from the longitudinal centre line (3);
wherein the medical instrument further comprises:
   an inner guide (51; 36) provided between the longitudinal centre line (3) and the inner longitudinal side (7) of the fingers (4); and
   an outer guide (52; 37), wherein the fingers (4) are provided between the outer guide (52; 37) and the longitudinal centre line (3);
wherein the first rod (1) carries the inner guide (51; 36) and the outer guide (52; 37);
wherein each finger (4; 94; 144) has a first curved zone (9) which defines a first finger part (10) which extends from the first finger end (5) to the first curved zone (9) and a second finger part (11) which extends from the first curved zone (9) to the free end (6) of the finger (4; 94; 144);
wherein, viewed from the first finger ends (5) to the second finger ends (6), the fingers (4; 94; 144) in the first curved zone (9) bend away from the longitudinal centre line (3);
wherein, in the second position, the outer guide (52) grips on the outer longitudinal side (8) of the second finger part (11) of the fingers (4; 94; 144).

17. Medical instrument according to clause 16, wherein, in the first position, the inner guide (51; 36) grips on the inner longitudinal side (7) of the first finger part (10) of the fingers (4; 94; 144).

18. Medical instrument according to one of clauses 16-17, wherein, in the second position, the inner longitudinal side (7) of the second finger part (11) of the fingers (4; 94; 144) lies free from the inner guide (51; 36).

19. Medical instrument according to one of clauses 16-18, wherein, in the first position, the outer longitudinal side (8) of the first finger part (10) of the fingers (4; 94; 144) lies free from the outer guide (52; 37).

20. Medical instrument according to one of clauses 16-19, wherein, in the first position, the outer guide (52; 37) grips on the outer longitudinal side (8) of the first finger part (10) of the fingers (4; 94; 144).

21. Medical instrument according to clause 20, wherein, in the first position, the outer longitudinal side (8) of the second finger part (11) of the fingers (4; 94; 144) lies free from the outer guide (52; 37).

22. Medical instrument according to one of clauses 16-21, wherein, in the second position, the inner guide (51; 36) grips on the inner longitudinal side (7) of the first finger part (10) and/or the second finger part (11) of the fingers (4; 94; 144).

23. Medical instrument according to clause 22, wherein, in the second position, the inner longitudinal side (7) of the first finger part (10) of the fingers (4; 94; 144) lies free from the inner guide (51; 36).

24. Medical instrument according to one of clauses 16-23, wherein the fingers (4; 94; 144), in the aforementioned first curved zone (9), show a curve of at least 30°, in particular a curve of at least 45°, such as a curve of 50° or more.

25. Medical instrument according to one of clauses 16-24, wherein the fingers (4; 94; 144) show a kinked shape in the first curved zone (9), at least on the inner longitudinal side (7) of the fingers (4; 94; 144).

26. Medical instrument according to one of clauses 16-25, wherein the inner guide (51; 36) and the outer guide (13; 37) are immovable in relation to one another.

27. Medical instrument according to one of clauses 16-26, wherein the inner guide (51; 36) is designed, in order to guide the free ends (6) of the fingers (4) in a radially outward direction and in relation to the longitudinal centre line (3), when the aforementioned movement of the first rod (1) in relation to the second rod (2) takes place, in such a way that the fingers (4; 94; 144) move to the first position.

28. Medical instrument according to one of clauses 16-27, wherein the outer guide (13) is formed by a side of an annular edge (37) provided on the first rod (1) and facing towards the free ends (6) of the fingers (4).

29. Medical instrument according to one of clauses 16-28, preferably in combination with at least clause 27, wherein, in the first position, a slit is located between the fingers (4; 94; 144) and the inner guide (51; 36) with a radial size such that, with the aforementioned movement of the first rod (1) in relation to the second rod (2) in such a way that the fingers (4; 94; 144) move in the direction of the first position, the free ends (6) of the fingers (4; 94; 144) approach the prosthesis (40; 80) from the inside thereof.

30. Medical instrument according to one of clauses 16-29, wherein the outer guide (13; 37) extends around the longitudinal centre line (3) and, preferably, has a diameter smaller than the inner diameter of the prosthesis (40; 80).

31. Medical instrument according to one of the preceding clauses,
wherein the second rod (2) has a first conical guide surface (101);
wherein the fingers (4; 94; 144) of the aforementioned plurality of fingers, at the first finger ends (5), have a guide part (102) which can be displaced along and in contact with the first conical guide surface (101) in order to displace the fingers (4; 94; 144) from this first position to this second position, wherein the distance from the guide parts (102) to the longitudinal centre line in the first position is different compared with the second position.

32. Medical instrument according to clause 31, wherein the guide part (102) of an aforementioned finger (4; 94; 144) and the remainder of an aforementioned finger (4; 94; 144) are rigid in relation to one another.

33. Medical instrument according to one of clauses 31-32, wherein the distance from the fingers (4; 94; 144) to the longitudinal centre line (3) in the second position is greater than in the first position.

34. Medical instrument according to one of clauses 31-33, wherein the fingers (4; 94; 144) can be slid back from the second position, along and in contact with the guide surface, in the direction of the first position.

35. Medical instrument according to one of the preceding clauses 31-34, wherein the fingers (4; 94; 144) extend parallel to the longitudinal centre line (3).

36. Medical instrument according to one of the preceding clauses 31-35, wherein the instrument further comprises:
a second conical guide surface (103);
a second plurality of fingers (94), each with a first finger end (5) and a second finger end (6);
wherein the second finger ends (6) of the second plurality of fingers (94) are free ends;
wherein the fingers (94) of the second plurality of fingers, at the first finger ends (5), have a guide part (102) which is shiftable along and in contact with the second conical guide surface (103) from a first position to a second position, in which the distance from the guide parts (102) of the second plurality of fingers (94) to the longitudinal centre line is different compared with the first position;
wherein the first and second conical guide surfaces (101, 103) are mirrored in relation to one another, such as facing towards one another; and
wherein the free ends (6) of the first plurality of fingers (4) are pointed towards the free ends (6) of the second plurality of fingers (94) and the free ends (6) of the second plurality of fingers (94) are pointed towards the free ends (6) of the first plurality of fingers (4).

37. Medical instrument according to clause 36, wherein the first rod (2) is connected to the first (4) and/or second (94) plurality of fingers for the operation thereof.

38. Medical instrument according to one of clauses 36-37, further comprising a third rod (91) which extends along the second rod (2) and is connected to the second plurality of fingers (94) for the operation thereof.

39. Medical instrument according to one of the preceding clauses,
wherein the first rod (1) is provided with a slotted element (34) with slots (35) which extend in the longitudinal direction of the first rod (1);
wherein the fingers (4; 94; 144) of an aforementioned plurality of fingers extend in each case through an aforementioned slot (35);
wherein, in the one of the aforementioned first and second positions, the free ends (6) of these fingers (4; 94; 144) project outwards from the slots; and
wherein, in the other of the aforementioned first and second positions, the free ends (6) of these fingers (4; 94; 144) are sunk entirely into the slots (35).

40. Medical instrument according to clause 39, wherein the slots (35) have slot bases (36) which are designed as guide surfaces to guide the free finger ends (6) in a radial direction in the event of displacement of the second rod (2) in relation to the first rod (1).

41. Medical instrument according to one of clauses 39-40, wherein, in the one of the aforementioned first and second positions, in which the free finger ends (6) contact the outside of a hollow prosthesis provided on the instrument, a slit is provided between the fingers (4; 94; 144) and the slot bases (36) with a radial size such that, in the event of movement of the fingers (4; 94; 144) from the other of the aforementioned first or second positions in the direction of the one of the aforementioned first or second positions, the free finger ends (6) approach the hollow prosthesis provided on the instrument from the inside.

42. Medical instrument according to one of the preceding clauses, wherein the instrument further comprises a stop (39), such as a support ring, which, in the case of a prosthesis provided on the instrument, is located proximally from the prosthesis and is designed to prevent displacement of the prosthesis in the proximal direction along the instrument.

43. Medical instrument according to clause 42, wherein the stop is a support ring (39), which is attached to the first rod (1) by means of a number, such as 2 or 3, of carrier arms (46) disposed in a distributed manner over the circumference of the first rod (1).

44. Medical instrument according to one of the preceding clauses, wherein the instrument comprises, in use, a proximal end pointed away from the patient and, in use, a distal end pointed towards the patient, and wherein the plurality of fingers (4; 94; 144) is provided at the distal end.

45. Medical instrument according to clause 44, wherein the plurality of fingers comprises a first plurality of fingers (4), the first finger ends (5) of which face towards the distal end of the instrument and the free, second finger ends (6) of which face towards the proximal end of the instrument; and wherein the distance from the free ends (6) of the fingers (4) of the first plurality of fingers (4) to the second rod (2) in the first position is greater than in the second position.

46. Medical instrument according to clause 45, preferably in combination with the following clause 67 or 68, wherein, in the second position, the largest diameter defined by the first plurality of fingers (4) is smaller than the inner diameter of the prosthesis, in particular smaller than the inner diameter which the prosthesis has after it has been detached from the instrument.

47. Medical instrument according to one of clauses 45-46, wherein the second rod (2) is displaceable in a distal direction in relation to the first rod (1) for the aforementioned operation of the fingers (4) of the first plurality of fingers.

48. Medical instrument according to one of clauses 45-47, wherein the fingers (4) of the first plurality of fingers, viewed from the first finger end (5) to the free, second finger end (6), are kinked in a second curved zone (70) in a radially inward direction, wherein this second curved zone is, in particular, such that the part of the fingers (4) of the first plurality of fingers, which is located on the side of the second curved zone facing towards the second finger end (6), can extend parallel to the longitudinal direction of the instrument, whereas, viewed from the first finger ends (5) of the first plurality of fingers (4) in the direction of the second curved zone (70), the part of the fingers of the first plurality of fingers which is located on the side of the second curved zone facing towards the first finger end (5) protrudes in a radially outward direction.

49. Medical instrument according to one of clauses 45-48, wherein the free, second finger ends (6) of the first plurality of fingers (4) are provided with a hook with a hook opening which opens in the direction of the first finger ends.

50. Medical instrument according to one of clauses 44-49, wherein the plurality of fingers comprises a second plurality of fingers (94), the first finger ends (5) of which face towards the proximal end of the instrument and the second finger ends (6) of which face towards the distal end of the instrument, and wherein the instrument may further comprise a third rod (91), which extends along the first rod (1).

51. Medical instrument according to clause 50, wherein the distance from the free ends (6) of the fingers (94) of the second plurality of fingers to the longitudinal centre line (3) in the first position is greater than in the second position.

52. Medical instrument according to clause 50 or 51, preferably in combination at least clause 67 or 68, wherein, in the second position, the largest diameter defined by the second plurality of fingers (94) is smaller than the inner diameter of the prosthesis, in particular smaller than the inner diameter which the prosthesis has after it has been detached from the instrument.

53. Medical instrument according to one of clauses 50-52, wherein the third rod (91) is displaceable in relation to the first rod (1) in the longitudinal direction of the centre line (3) for the aforementioned operation of the fingers (94) of the second plurality of fingers.

54. Medical instrument according to one of clauses 50-53, wherein the fingers (94) of the second plurality of fingers, viewed from the first finger end (5) to the free, second finger end (6), are kinked in a second curved zone (70) in a radially inward direction, wherein this second curved zone (70) is, in particular, such that the part of the fingers (94) of the second plurality of fingers, which is located on the side of the second curved zone (70) facing towards the second finger end (6), can extend parallel to the longitudinal direction of the instrument, whereas, viewed from the first finger ends (5) of the second plurality of fingers (94) in the direction of the second curved zone (70), the part of the fingers (94) of the second plurality of fingers which is located on the side of the second curved zone (70) facing towards the first finger end (5) protrudes in a radially outward direction.

55. Medical instrument according to one of clauses 50-54, wherein the free, second finger ends (6) of the second plurality of fingers (94) are provided with a hook (60) with a hook opening (61) which opens in the direction of the first finger ends (5) thereof.

56. Medical instrument according to one of clauses 44-45, wherein the plurality of fingers comprises a third plurality of fingers (144), the first finger ends (5) of which face towards the proximal end of the instrument and the free, second finger ends (6) of which face towards the distal end of the instrument; and wherein the distance from the free ends (6) of the fingers (144) of the third plurality of fingers to the longitudinal centre line (3) in the first position is greater than in the second position.

57. Medical instrument according to clause 56, preferably in combination with the following clause 67 or 68, wherein, in the second position, the largest diameter defined by the third plurality of fingers (144) is smaller than the inner diameter of the prosthesis, in particular smaller than the inner diameter which the prosthesis has after it has been detached from the instrument.

58. Medical instrument according to one of clauses 56-57, wherein the second rod (2) is displaceable in relation to the first rod (1) in the longitudinal direction of the centre line (3) for the aforementioned operation of the fingers (144) of the third plurality of fingers.

59. Medical instrument according to one of clauses 56-58, wherein the fingers (144) of the third plurality of fingers, viewed from the first finger end (5) to the free, second finger end (6), are kinked in a first curved zone (9) in a radially outward direction.

60. Medical instrument according to one of clauses 56-59, wherein the free, second finger ends (6) of the third plurality of fingers (144) are provided with a hook (60) with a hook opening (61) which opens in the direction of the first finger ends (5).

61. Medical instrument according to one of clauses 56-59, wherein the fingers (144) of the third plurality of fingers, viewed from the first finger end (5) to the free, second finger end (6), are kinked in a second curved zone (70) in a radially inward direction, and wherein this second curved zone (70) is, in particular, such that the part of the fingers (144) of the third plurality of fingers, which is located on the side of the second curved zone (70) facing away from the first finger end (5), can extend parallel to the longitudinal direction of the instrument, whereas, viewed from the first finger ends (5) of the third plurality of fingers (144) in the direction of the second curved zone (70), the part of the fingers (144) of the third plurality of fingers which is located on the side facing towards the first finger ends (5) adjacent to the second curved zone (70) protrudes in a radially outward direction.

62. Medical instrument according to one of the preceding clauses, wherein the instrument is sterile.

63. Medical instrument according to one of the preceding clauses, wherein the instrument is made from one or more medically acceptable materials.

64. Medical instrument according to one of the preceding clauses, wherein the first rod (1) has a carrier part (28) to carry a prosthesis (40, 80, 90, 96, 800), and wherein the fingers (4; 94; 144) of the at least one plurality of fingers are movable in relation to the carrier part (28).

65. Medical instrument according to one of the preceding clauses, wherein the instrument is intended for the implantation of a prosthesis (40, 80, 90, 96, 800).

66. Medical instrument according to one of the preceding clauses, further comprising a prosthesis (40, 80, 90, 96, 800), wherein the free ends (6) of the fingers (4), in the one of the aforementioned first and second positions, grip on the prosthesis and, in the other of the aforementioned first and second positions, preferably lie free from the prosthesis.

67. Medical instrument according to one of clauses 64-66, wherein the prosthesis (40, 80, 90, 96) has a tubular element.

68. Medical instrument according to one of clauses 64-65, wherein the prosthesis (40, 80, 90, 96) is a 'prosthesis of the type with a tubular element' (42) with a distal (43) and proximal (41) flange which extend along the circumference of the tubular element, wherein the distal and/or proximal flange has flange feet (44) which are bendable from an extended position extending in an axial direction to a radial position extending in a radial direction.

69. Medical instrument according to one of clauses 67 of 68, wherein the carrier part (28) is designed to grip on the inside of the tubular element (198) or organ (96).

70. Medical instrument according to one of clauses 64-69, wherein biological tissue is located between the prosthesis (40, 80, 90, 96) and the instrument.

71. Medical instrument according to one of clauses 64-70, wherein the prosthesis (40, 80, 90, 96, 800) is a heart prosthesis, such as a heart valve prosthesis or ring prosthesis.

72. Medical instrument, wherein the prosthesis is one from the group of:
 a ring prosthesis (800) according to one of clauses 75-100; and/or
 a stent (90, 96) according to one of the following clauses 101-111; and/or
 a stented valve prosthesis; and/or
 a 'prosthesis of the type with a tubular element'.

73. Medical instrument according to one of the preceding clauses, wherein the first rod and/or second rod and/or third rod are designed as flexible, such as bendable or kinkable, over at least a part of the length thereof, in such a way that the longitudinal centre line of the respective rod(s) is flexible, such as bendable or kinkable.

74. Medical instrument according to clause 73, wherein the first rod and/or second rod and/or third rod, over at least a part of the length thereof, are designed from superelastic material, such as nitinol designed in superelastic form; and/or wherein the first rod and/or second rod and/or third rod are designed, over at least a part of the length thereof, as a wire, such as steel wire.

75. Ring prosthesis (800) for the constriction of the through-flow passage of a heart valve, wherein the ring prosthesis (800) comprises:
   a first ring (802); and
   anchoring elements (801) to attach the first ring (802) to tissue surrounding the through-flow passage to be constricted, wherein each anchoring element (801) is attached to the first ring (802);
wherein the first ring is formed from a wire (802) which, viewed in the circumferential direction of the first ring, extends along a waved pattern in such a way that the diameter of the ring prosthesis (800) is constrictable from a first condition to a second condition, wherein the wave lengths (L) of the waves of the waved pattern in the aforementioned first condition are greater than in the aforementioned second condition.

76. Ring prosthesis (800) according to clause 75, wherein the waved wire is in the first position and the ring, in this first position, is under a pre-tension, as a result of which the ring is inclined to constrict to the second position.

77. Ring prosthesis (800) according to clause 75 or 76, wherein the anchoring elements comprise pins (801).

78. Ring prosthesis (800) according to clause 77, wherein the pins (801) extend in the axial direction of the first ring (802).

79. Ring prosthesis (800) according to one of the preceding clauses 77-78, wherein at least a part of the pins (801) is pre-tensioned in order to displace the free ends, once the pre-tension has been released, in relation to the ends of the pins attached to the ring prosthesis.

80. Ring prosthesis (800) according to clause 79, wherein the pins, or at least a part thereof, are pre-tensioned in order, following release with the free ends, to
   to be displaced in a radially inward direction; and/or
   to be displaced in a radially outward direction; and/or
   to be displaced in a tangential direction; and/or
   to be displaced in pairs towards one another.

81. Ring prosthesis (800) according to one of the preceding clauses 75-80, wherein the anchoring elements (801) are disposed in a distributed manner, such as evenly distributed, over the circumference of the first ring (802).

82. Ring prosthesis (800) according to one of the preceding clauses 75-81, further comprising a plurality of segments (806) disposed in a distributed manner over the circumference of the first ring (802), wherein each segment (806) is attached to the first ring (802).

83. Ring prosthesis (800) according to clause 82, wherein segments adjacent in the circumferential direction may, in the first condition, lie at a distance from one another leaving an intermediate space free, and, in the second position, lying against one another, may form an essentially closed second ring which prevents further constriction.

84. Ring prosthesis (800) according to one of the preceding clauses 75-83, wherein the amplitude of the waved pattern extends in the radial direction of the ring.

85. Ring prosthesis (800) according to clause 84, wherein the amplitude of the waved pattern extends at an angle of 30° to 90° in relation to the axial direction (805) of the first ring (802).

86. Ring prosthesis (800) according to one of clauses 75-85, wherein the position of the amplitude of the waved pattern in relation to the axial direction of the first ring, viewed along the circumference of the first ring, varies.

87. Ring prosthesis (800) according to one of the preceding clauses 75-86, wherein the ring prosthesis (800) comprises at most one aforementioned anchoring element (801) for each wave cycle of the waved pattern.

88. Ring prosthesis (800) according to one of the preceding clauses 75-87, wherein the anchoring elements (801) are attached to the first ring (802) in each case in the same part of the wave cycle of the waved pattern.

89. Ring prosthesis (800) according to clause 87 or 88, wherein the anchoring elements (801) are attached to the inward-facing troughs (803) of the waved pattern, in particular at the midpoint of these troughs.

90. Ring prosthesis (800) according to clause 87 or 88, wherein the anchoring elements (801) are attached to the outward-facing peaks (804) of the waved pattern, in particular at the midpoint of these peaks.

91. Ring prosthesis (801) according to one of the preceding clauses 75-90, wherein the waved pattern is a sinusoidal pattern.

92. Ring prosthesis (801) according to one of the preceding clauses 75-91, wherein the waved pattern comprises 8, 9, 10, 11, 12, 13, 14 or 15 wave cycles, wherein the first ring (802) has a diameter in the 15 mm to 55 mm range.

93. Ring prosthesis (801) according to one of the preceding clauses 75-92, wherein, viewed in the direction of the wave height (H), the distance between the peaks (804) and troughs (803) of the waves lies in the 0.5 mm to 20 mm range, such as in the 0.5 to 3 mm range.

94. Ring prosthesis (800) according to one of the preceding clauses 75-93, wherein the anchoring elements comprise clamping mouths with a first jaw part (808) and a second jaw part (809) which is movable in relation to the first jaw part in order to clamp tissue between the jaw parts.

95. Ring prosthesis (800) according to clause 94, wherein the clamping mouths are brought from a closed condition against spring action to an open condition, and can be returned from the opened condition to the closed condition under the influence of said spring action.

96. Ring prosthesis (800) according to clause 95, wherein the clamping mouths comprise a memory material which provides the aforementioned spring action, and wherein the clamping mouths are fixed in the opened condition by means of a temperature treatment in order to be able to return to the closed position if a threshold temperature is exceeded or understepped.

97. Ring prosthesis (800) according to one of clauses 94-96, wherein the clamping mouths are provided on the outer circumference of the ring prosthesis and are pointed with the mouth opening in a radially outward direction.

98. Ring prosthesis according to one of clauses 94-97, wherein the clamping mouths comprise one or more teeth which are attached, in particular, to a jaw part and point towards the opposite jaw part.

99. Ring prosthesis (800) according to one of clauses 75-98, wherein an imaginary line, which forms the midpoint between the wave troughs and wave peaks, defines a basic shape of the ring prosthesis, and wherein this basic shape, viewed in the axial direction of the ring prosthesis, is bean-shaped or kidney-shaped.

100. Ring prosthesis (800) according to one of clauses 75-99, wherein an imaginary line, which forms the midpoint between the wave troughs and wave peaks, defines a basic shape of the ring prosthesis, and wherein this basic shape is a 3-dimensional shape, such as a sinusoidal shape.

101. Stent (96), comprising
  a tubular element (198) which is expandable in a radial direction from a compressed condition to an expanded condition, and which has a proximal and distal end;
  a proximal flange (83) of proximal flange feet provided around the tubular element (196); and
  a distal flange (82) of distal flange feet provided around the tubular element (196);
wherein the distal (82) and proximal (83) flange feet are attached with a fixed end to the tubular element (196) and have another end which is free;
wherein the distal and proximal flange feet have a radial position, in which the free ends of the flange feet point in a radial direction for anchoring with surrounding tissue;
wherein the distal flange feet (82) are pivotable from an extended position, in which the distal flange feet (82) lie in the longitudinal direction of the tubular element (196), to a radial position extending in a radial direction; and
wherein the distal flange feet (82) are provided distally from the proximal flange feet (83).

102. Stent (96) according to clause 101, wherein the proximal flange feet (83) are pivotable from an extended position, in which the proximal flange feet (83) lie in the longitudinal direction of the tubular element (198), to a radial position extending in a radial direction.

103. Stent (96) according to one of clauses 101-102, wherein the fixed ends of the distal flange feet (82) are located at a distance from the distal end of the tubular element (196) which is greater than 2× the length of the distal flange feet (82); and
wherein the fixed ends of the proximal flange feet (83) are located at a distance from the proximal end of the tubular element (196) which is greater than 2× the length of the proximal flange feet (83).

104. Stent (96) according to one of clauses 101-103, further comprising a heart valve provided in the tubular element (196).

105. Stent (96) according to clause 104, wherein the heart valve is a natural donor valve, such as from an animal or human.

106. Stent (96) according to clause 105, wherein the donor valve is a biological valve chosen from the group of:
  porcine valves; and/or
  bovine valves; and/or
  equine valves; and/or
  human valves; and/or
  kangaroo valves.

107. Stent (96) according to one of clauses 101-106, wherein the separate flanges, or parts thereof, or the separate flange feet of the separate flanges have an unequal shape and/or length and/or width in relation to one another, and/or angle in relation to the longitudinal axis, and/or fillings.

108. Stent (96) according to one of clauses 101-107, wherein the fillings of the separate flanges, or the separate flange feet of the separate flanges, have an unequal shape and/or length and/or width in relation to one another, and/or angle in relation to the longitudinal axis, and/or consistency and/or material properties.

109. Stent (96) according to one of clauses 101-108, wherein the fillings of the separate flange feet extend beyond the circumference of a flange foot, and/or in a lateral and/or radial direction therefrom.

110. Stent (96) according to one of clauses 101-109, wherein the fillings of the separate flange feet are interconnected in such a way that a continuity arises between all or a number of fillings of the flange feet of one or both flanges.

111. Stent according to one of clauses 101-106, further comprising a ring structure according to one of clauses 136-162, which provides the proximal and distal flange feet.

112. Prosthesis for attachment in a passage surrounded by tissue,
wherein the prosthesis comprises a tubular element formed from memory material with a proximal and distal flange which extend around the tubular element;
wherein the distal and proximal flange have a radial position, in which they project from the tubular element in a radially outward direction in order to clamp tissue surrounding the passage between the distal and proximal flange;
wherein the distal flange consists of distal flange feet, which are bendable from the radial position, against a pre-tension created by the memory material, to an extended position, in which the distal flange feet extend in the longitudinal direction of the tubular element and which are fixable in this extended position, in order to return to the radial position under the influence of the pre-tension once the fixing has been undone;
wherein the distal flange feet, at the ends attached to the tubular element, are provided on the side facing the proximal flange with a filling which is designed, in the radial position of the distal and proximal flange, to increase the clamping force with which the distal and proximal flange clamp the tissue in situ.

113. Prosthesis according to clause 112, wherein the distal flange feet have a concave-curved part which follows on from the ends of the distal flange feet attached to the tubular element, wherein the hollow side of the concave-curved part faces towards the proximal flange, and wherein the filling is provided in the hollow side of the concave-curved part.

114. Prosthesis according to clause 113, wherein the filling projects from the concave-curved part in the direction of the opposite flange feet.

115. Prosthesis according to clause 114, wherein the filling is compressible, in such a way that, if the flange feet are in the radial position, the part of the filling projecting from the cavity can be compressed.

116. Prosthesis according to one of clauses 112-115, wherein the concave-curved part of the distal flange feet, on the side thereof facing towards the free ends of the distal flange feet, viewed in the radial direction and radial position, changes to a straight part.

117. Prosthesis according to one of clauses 112-116, wherein the proximal flange consists of proximal flange feet, which are bendable from the radial position, against a pre-tension created by the memory material, to an extended position, in which the proximal flange feet extend in the longitudinal direction of the tubular element and which are fixable in this extended position, in order to return to the radial position under the influence of the pre-tension once the fixing has been undone;
wherein the proximal flange feet, at the ends attached to the tubular element, are provided on the side facing the distal flange with a filling which is designed, in the radial position of the distal and proximal flange, to increase the clamping force with which the distal and proximal flange clamp the tissue in situ.

118. Prosthesis according to clause 117, wherein the proximal flange feet have a concave-curved part which follows on from the ends of the proximal flange feet attached to the tubular element, wherein the hollow side of the concave-curved part faces towards the distal flange, and wherein the filling is provided in the hollow side of the concave-curved part.

119. Prosthesis according to one of clauses 117-118, wherein the concave-curved part of the proximal flange feet, on the side thereof facing towards the free ends of the proximal flange feet, viewed in the radial direction and radial position, changes to a straight part.

120. Prosthesis according to one of clauses 112-119, wherein the filling is made from a material other than the material from which the tubular element, the distal flange and the proximal flange are made.

121. Prosthesis according to one of clauses 112-120, wherein the filling is made from a foam-like material and/or a textile and/or a plastic.

122. Prosthesis according to one of clauses 112-121, wherein the memory material is a memory metal.

123. Prosthesis according to clause 122, wherein the memory metal is a nitinol alloy.

124. Prosthesis according to one of clauses 112-123, wherein the separate flanges, or parts thereof, or the separate flange feet of the separate flanges have an unequal shape and/or length, or width in relation to one another, and/or angle in relation to the longitudinal axis, and/or fillings.

125. Prosthesis according to clauses 112-124, wherein the fillings of the separate flanges, or the separate flange feet of the separate flanges, may have an unequal shape and/or length and/or width in relation to one another, and/or angle in relation to the longitudinal axis, and/or consistency and/or material properties.

126. Prosthesis according to clause 112-125, wherein the fillings of the separate flange feet extend beyond the circumference of a flange foot, and/or in a lateral and/or radial direction therefrom.

127. Prosthesis according to clause 112-126, wherein the fillings of the separate flange feet are interconnected in such a way that a continuity arises between all or a number of fillings of the flange feet of one or both flanges.

128. Applicator (1500) for the implantation of a hollow prosthesis with an open distal end and an open proximal end, comprising:
   a tube (1501) with an inner screw thread over at least a part of the length thereof;
   a pin (1502) extending through the tube (1501) with, over at least a part of the length thereof, an outer screw thread (1507) which mates with the aforementioned inner screw thread;
wherein the tube (1501) carries a sheathing (1505) on the distal end thereof;
wherein the pin (1502) is equipped, on the distal end thereof, with a carrier (1504) for a prosthesis (802), said carrier (1504), on the one hand, being rotatable in relation to the pin (1502) around the longitudinal centre line of the pin and, on the other hand, being shiftable from a position pushed out from the sheathing (1505) in the proximal direction in relation to the sheathing (1505) to a position entirely or partially retracted into the sheathing, by rotating the tube (1501) in relation to the pin; and
wherein the applicator further comprises an axial guide (1507) which is designed, on the one hand, to prevent rotation of the carrier (1504) in relation to the sheathing (1505) around the longitudinal centre line (1508) of the pin (1502) and, on the other hand, to allow axial shifting of the carrier (1504) in relation to the sheathing (1505).

129. Applicator according to clause 128, wherein the carrier (1504), on the distal end thereof, comprises a nose part (1506) tapering in the distal direction with a rounded point (1509).

130. Applicator according to one of clauses 128-129, wherein the carrier part has a carrier surface facing radially outwards, the outer contour of which matches the inner contour of the sheathing.

131. Applicator according to one of clauses 128-130, wherein the tube (1501) and the pin (1502) are designed to be flexible, such as bendable or kinkable, over at least a part of the length thereof, in such a way that the longitudinal centre line of the tube (1501) and pin (1502) is flexible, such as bendable or kinkable.

132. Applicator according to one of clauses 128-131, wherein the tube (1501) and the pin (1502), over at least a part of the length thereof, are designed from superelastic material, such as nitinol designed in superelastic form; and/or wherein the tube (1501) and the pin (1502), over at least a part of the length thereof, are designed as a wire, such as steel wire.

133. Assembly comprising, on the one hand, an applicator according to one of clauses 128-132 and, on the other hand, an aforementioned hollow prosthesis, in particular a heart prosthesis, wherein the prosthesis is provided on the carrier in a manner carried by the carrier.

134. Assembly according to clause 133 in combination with at least clause 132, wherein the prosthesis is clamped on the carrier surface (1510).

135. Assembly according to clause 133 or 134, wherein the prosthesis is one from the group of:
   a ring prosthesis according to one of clauses 75-100; and/or
   a stent according to one of clauses 101-111; and/or
   a 'prosthesis of the type with a tubular element'.

136. Variable-diameter ring structure (1600) with distal (1604) and proximal (1603) flange feet,
wherein the ring structure has an axial direction (1605) and a radial direction (R) transverse to the axial direction;
wherein the distal and proximal flange feet (1604, 1603) have a radial position, in which the free ends (1606, 1607) of the flange feet point in the radial direction for anchoring with surrounding tissue (1608);
wherein the distal flange feet (1604) have an extended position, in which the distal flange feet extend in the axial direction; and
wherein the distal flange feet (1604), if they are in the extended position, are under a pre-tension (1609), which, when released, bends the distal flange feet from the extended position to the radial position; and
wherein the ring structure (1600) is constructed from a series of elongated closed loops (1610) lying next to one another which, in each case, at the midpoint of the longitudinal sides thereof, are attached laterally to one another via a junction (1611) to form this ring structure, in such a way that, on the one hand, the imaginary line (1612) through all junctions (1611) forms a closed ring and divides each loop (1610) into an aforementioned distal flange foot (1601) and an aforementioned proximal flange foot (1602) and, on the other hand, the ring structure is expandable and/or compressible.

137. Ring structure (1600) according to clause 136, wherein the distal flange feet (1604) are bendable from the radial position to the extended position against a resilience which builds up the aforementioned pre-tension (1609).

138. Ring structure (1600) according to one of clauses 136-137, wherein the proximal flange feet (1603) have an extended position, in which the proximal flange feet extend in the axial direction (1605); and
wherein the proximal flange feet, if they are in the extended position, are under a pre-tension (1609), which, when released, bends the proximal flange feet (1603) from the extended position to the radial position.

139. Ring structure (1600) according to clause 138, wherein the proximal flange feet (1603) are bendable from the radial position to the extended position against a resilience which builds up the aforementioned pre-tension (1609).

140. Ring structure (1600) according to one of clauses 136-139, wherein the ring structure is made from a memory material.

141. Ring structure (1600) according to clause 140, wherein the memory material is a memory metal, such as a nitinol alloy.

142. Ring structure (1600) according to one of clauses 136-140, wherein the ring structure is expandable from a first condition (X1) to a second condition (X2), and wherein the ring structure, when it is in the first condition, is under a radial pre-tension (1613), which, when released, causes the ring structure to expand in the direction of the second condition.

143. Ring structure (1600) according to one of clauses 136-141, wherein the ring structure is expandable from a first condition (X1) to a second condition (X2), and wherein the ring structure, when it is in the second condition, is under a pre-tension, which, when released, causes the ring structure to contract in the direction of the first condition (X1).

144. Ring structure (1600) according to one of clauses 137-143, wherein one or more of the junctions (1611) is provided with one or more radial bores (1614).

145. Ring structure (1600) according to clause 144, wherein at least 3, such as 4 or 8, junctions (1611) lying over the circumference of the ring structure have one or more aforementioned radial bores (1614).

146. Ring structure (1600) according to clause 144 of 145, wherein all junctions have one or more aforementioned radial bores (1614).

147. Ring structure (1600) according to one of clauses 134-146,
wherein the distal flange feet (1604), in the radial position, show a bulge (1615) facing towards the proximal flange feet (1603);
or
wherein the proximal flange feet, in the radial position, show a bulge facing towards the distal flange feet;

148. Ring structure (1600) according to clause 147, wherein these bulges (1615) are provided in the halves (1616) of the respective flange feet adjacent to the junction (1611).

149. Ring structure (1600) according to one of clauses 136-148, wherein the ring structure comprises a single piece of material.

150. Ring structure (1600) according to clause 149, wherein the ring structure is made from a piece of tubular or otherwise plate material.

151. Ring structure (1600) according to one of clauses 136-150, wherein the ring structure is sterile.

152. Ring structure (1600) according to one of clauses 136-151, wherein the ring structure is made from one or more medically acceptable materials.

153. Ring structure (1600) according to one of clauses 136-152, wherein one or more of the flange feet comprise one or more pins on the sides facing towards one another.

154. Ring structure (1600) according to one of clauses 136-153, wherein the ring structure or one or more flanges thereof, or one or more flange feet thereof are totally or partially coated in a sealing manner with tissue, such as pericardium, or materials, such as textile or plastics which can be tolerated by the body, such as Dacron and Teflon, which prevent the passage of blood or other fluids.

155. Ring structure (1600) according to one of clauses 136-153, wherein one or both flanges, or the flange feet of one or both flanges thereof, differ from one another in length and/or in width and/or in shape and/or in angle in relation to the longitudinal axis, and/or manner of coating and/or filling.

156. Ring structure (1600) according to one of clauses 136-155, wherein the separate flanges, or parts thereof, or the separate flange feet of the separate flanges have an unequal shape and/or length and/or width in relation to one another, and/or angle in relation to the longitudinal axis, and/or fillings.

157. Ring structure (1600) according to clauses 136-156, wherein the fillings of the separate flanges, or the separate flange feet of the separate flanges, may have an unequal shape and/or length and/or width in relation to one another, and/or angle in relation to the longitudinal axis, and/or consistency and/or material properties.

158. Ring structure (1600) according to clauses 136-157, wherein the fillings of the separate flange feet extend beyond the circumference of a flange foot, and/or in a lateral and/or radial direction therefrom.

159. Ring structure (1600) according to clauses 136-158, wherein the fillings of the separate flange feet are interconnected in such a way that a continuity arises between all or a number of fillings of the flange feet of one or both flanges.

160. Assembly comprising a ring structure (1600) according to one of clauses 132-149, and a heart valve (1617) mounted therein.

161. Assembly according to clause 150, wherein the heart valve (1617) is a natural donor valve, such as from an animal or human.

162. Assembly according to clause 150 or 151, wherein the heart valve (1617) comprises a biological material, which is chosen from the group of:
porcine valves; and/or
bovine valves; and/or
equine valves; and/or
human valves; and/or
kangaroo valves.

163. Manipulator (1700) for releasing a prosthesis (1701), wherein the prosthesis has a plurality of distal (1702) and proximal (1703) flange feet, which:
have a radial position, in which the free ends (1704, 1705) of the flange feet point in the radial direction for anchoring with surrounding tissue (1706);
have an extended position, in which the flange feet extend in the radial direction; and,
if they are in the extended position, are under a pre-tension, which, when released, bends the distal flange feet from the extended position to the radial position;
wherein the manipulator (1700) comprises:
a plurality of U-shaped obstacle elements (1710) with a first leg (1711) and a second leg (1712), the free ends (1713, 1714) of which point in the distal direction (0);
an operating element (1715);
for each obstacle element (1714), a cord (1716), one end of which is attached to the obstacle element (1710) and the other end of which is connected to the operating element (1715) in such a way that, when the operating element (1715) is displaced in the proximal direction (P), the obstacle elements (1710) are retracted in the proximal direction.

164. Manipulator (1700) according to clause 163,
wherein a first length (L1) is defined as the axial distance, in the extended condition of the flange feet, between the free ends (1704 and 1705) of the distal and proximal flange feet;

wherein the first legs (1711) of the obstacle elements have a second length (L2); and wherein the second length (L2) is at least 75%, such as at least 90%, of the first length (L1).

165. Manipulator (1700) according to clause 164, wherein the second length (L2) is greater than the first length (L1).

166. Manipulator (1700) according to one of clauses 163-165, wherein the second legs (1712) are shorter than the first legs (1711).

167. Manipulator (1700) according to one of clauses 163-166, wherein the proximal flange feet have a third length (L3), wherein the second legs (1712) have a fourth length (L4); and wherein the fourth length (L4) is at most equal to the third length (L3).

168. Manipulator (1700) according to clause 167, wherein the fourth length (L4) is at least 75% of the third length (L3).

169. Assembly comprising a manipulator (1700) according to one of clauses 163-168 and a prosthesis (1701), wherein the prosthesis has a plurality of distal (1702) and proximal (1703) flange feet, which:

have a radial position, in which the free ends (1704, 1705) of the flange feet point in the radial direction for anchoring with surrounding tissue (1706);

have an extended position, in which the flange feet extend in the axial direction; and, if they are in the extended position, are under a pretension, which, when released, bends the distal flange feet from the extended position to the radial position.

170. Assembly according to clause 169, wherein a heart valve is mounted in the prosthesis.

171. Assembly according to clause 170, wherein the heart valve is a natural donor valve, such as from an animal or human.

172. Assembly according to clause 170 or 171, wherein the heart valve comprises a biological material, which is chosen from the group of:

porcine valves; and/or
bovine valves; and/or
equine valves; and/or
human valves; and/or
kangaroo valves.

173. Assembly according to one of clauses 169-172, wherein the prosthesis is one from the group of:

a ring prosthesis (800) according to one of clauses 75-100; and/or
a stent (90, 96) according to one of clauses 101-111; and/or
a ring structure according to one of clauses 136-162; and/or
a stented valve prosthesis; and/or
a 'prosthesis of the type with a tubular element'.

174. Assembly according to one of clauses 166-170, wherein the assembly further comprises a sleeve with a diameter smaller than the maximum or expanded diameter of the prosthesis.

175. Port assembly (1800), comprising:

an annular connector (1802) which surrounds a port passage (1830); and
a sealing cap (1803) to seal the port passage;
wherein the port passage extends from a first connector end (1828) to a second connector end (1827);
wherein the second connector end comprises a crosswise contact surface (1828) to lie against a wall (1829) of an organ;
wherein, in the crosswise contact surface, at least one adhesive slot (1808, 1810), such as two adhesive slots, is provided, which extends around the port passage (1830) and which is connectable via a feed channel (1812) which opens out into this slot to a source for tissue adhesive; and wherein, in the crosswise contact surface (1828), at least one ring, such as two rings, of one or more suction mouths (1809) is provided, said ring extending around the port passage and being connectable via a suction channel (1811) to a suction source to suck the crosswise contact surface firmly against the wall of the organ.

176. Port assembly (1800) according to clause 175, wherein the connector (1802) and sealing cap (1803) are provided with a first mating interlocking mechanism (1804, 1805), such as a bayonet connection or screw thread, with which the connector and sealing cap are attachable to one another in a manner which seals the port passage.

177. Port assembly (1800) according to clause 176, wherein the first mating interlocking mechanism comprises an inner screw thread (1805) provided on the connector (1802) and an outer screw thread (1804) provided on the closing cap (1803).

178. Port assembly (1800) according to one of clauses 175-177, wherein the at least one ring of suction mouths comprises at least one suction slot (1809), such as two suction slots, which extend around the port passage (1830).

179. Port assembly (1800) according to one of the preceding clauses 175-178, further comprising an adhesive source for tissue adhesive and/or a suction source to generate a suction force in the at least one ring of one or more suction mouths (1808).

180. Port assembly (1800) according to one of the preceding clauses 175-179, further comprising a work channel (1820, 1822) which is connectable in a disconnectable manner to the connector (1802).

181. Port assembly (1800) according to clause 180, wherein the work channel comprises a stiff or stiffened channel part (1822) and a flexible channel part (1820) which is provided between the connector (1802) and the stiff channel part (1822) in such a way that the stiff channel part is pivotable in relation to the connector.

182. Port assembly (1850), comprising:

an annular connector (1802) which surrounds a port passage (1830), said port passage extending from a first connector end (1828) to a second connector end (1827); and
a work channel (1820, 1822) which is connectable in a disconnectable manner to the connector (1802);
wherein the second connector end (1827) comprises a crosswise contact surface (1828) to lie against a wall (1829) of an organ;
and
wherein the work channel comprises a stiff or stiffened channel part (1822) and a flexible channel part (1820) which is provided between the connector (1802) and the stiff channel part (1822) in such a way that the stiff channel part (1822) is pivotable in relation to the connector (1802).

183. Port assembly (1850) according to clause 182, wherein the assembly further comprises a closing cap (1803) to close the port passage (1830).

184. Port assembly (1800, 1850) according to one of clauses 180-183, wherein the connector (1802) and the work channel (1820, 1822) are provided with a second mating interlocking mechanism (1806, 1807), such as a bayonet connection or screw thread, with which the connector and the work channel are attachable to one another in a sealing manner.

185. Port assembly (1800, 1850) according to clause 184, wherein the second mating interlocking mechanism comprises an outer screw thread (1806) provided on the connector and an inner screw thread (1807) provided on the closing cap.

186. Port assembly (1800, 1850) according to one of clauses 180-185, wherein the end of the work channel facing away from the connector is provided with a seal (1824) which is designed, on the one hand, to seal the access to the passage surrounded by the work channel and, on the other hand, to allow through an instrument which is to be inserted inwards into the work channel, while maintaining the seal.

187. Port assembly (1800, 1850) according to one of the preceding clauses 180-186, wherein the work channel is provided with at least one connection, such as two, three or four connections, for gassing and/or degassing and/or irrigation and/or drainage of the passage surrounded by the work channel.

188. Port assembly (1800, 1850) according to one of the preceding clauses 180-187, wherein one or more valves are provided in the work channel.

189. Port assembly (1800, 1850) according to one of the preceding clauses 175-188, wherein the connector is made from soluble, so-called 'bioabsorbable' or 'biodegradable' materials.

190. Port assembly (1800, 1850) according to one of clauses 175-189, wherein the cap is coated on the crosswise side with anti-thrombotic materials or chemical components to prevent blood clotting in situ; or
wherein the cap is covered on the crosswise side with a piece of a vascular prosthesis, human pericardium, or other material to promote the growth of endothelial tissue in situ.

191. Port assembly (1800, 1850) according to one of clauses 175-190, wherein the connector is provided with one or more contact and/or pressure sensors on the crosswise edge.

192. Method for implanting a valve prosthesis in a passage through which blood flows, comprising the following steps:
   the insertion into the passage and attachment to surrounding tissue of a ring prosthesis which, under pre-tension, is held in a first diameter, wherein the pre-tension tends to constrict the ring prosthesis to a smaller, second diameter;
   the insertion into the passage of the valve prosthesis;
   the release of the pre-tensioned ring prosthesis in such a way that, under the influence of the pre-tension, it draws the tissue surrounding the passage against the valve prosthesis.

193. Method according to clause 192, wherein the step of implantation and attachment of the ring prosthesis in the passage takes place prior to the step of implantation of the valve prosthesis in the passage.

194. Method according to clause 192, wherein the step of implantation of the valve prosthesis in the passage takes place prior to the step of implantation and attachment of the ring prosthesis in the passage.

195. Method according to clause 192, wherein the steps of, on the one hand, implantation and attachment of the ring prosthesis in the passage and, on the other hand, of implantation of the valve prosthesis in the passage take place simultaneously.

196. Method according to clause 195, wherein the ring prosthesis and valve prosthesis are implanted and attached as a pre-assembled unit.

197. Method according to one of clauses 192-196, wherein the valve prosthesis is implanted within the lumen surrounded by the ring prosthesis or is provided within the lumen surrounded by the ring prosthesis.

198. Method according to one of clauses 192-197, wherein the ring prosthesis is one from the group comprising: ring prostheses according to one of clauses 75-100; or ring structures according to one of clauses 136-159.

199. Valve prosthesis, such as a heart valve prosthesis, comprising:
   at least a first radial flange provided with radial slots;
   pins which project in an axial direction through the slots;
   a tensioning mechanism designed to be able to pre-tension the pins in order to move through the slots in a radially inward direction; and
   a valve, such as a heart valve.

200. Valve prosthesis according to clause 199, further comprising a ring prosthesis according to one of clauses 75-100, wherein the pins are mounted on the waved wire of this ring prosthesis, and wherein the waved wire can be pre-tensioned in order to drive the pins in a radially inward direction through the slots.

201. Valve prosthesis according to one of clauses 199-201, wherein the tensioning mechanism comprises, for each slot, a radially oriented spring which grips on an aforementioned pin.

202. Valve prosthesis according to one of clauses 199-201, wherein the first flange is constructed from a plurality of flange feet with an aforementioned slot.

203. Valve prosthesis according to one of clauses 199-202, wherein the tensioning mechanism is housed in a cavity formed in the first flange, or cavities formed in flange feet and, and wherein the slots open out into this cavity/these cavities.

204. Valve prosthesis according to clause 203, wherein the cavity is formed by designing the first flange as double-walled (or the cavities are formed by designing the flange feet as double-walled).

205. Valve prosthesis according to one of clauses 199-204, wherein the first flange is movable from an extended position, in which the first flange is axially oriented and the pins are radially oriented, to a radial position, in which the first flange is radially oriented and the pins are axially oriented.

206. Valve prosthesis according to one of the preceding clauses 199-205, further comprising a second radial flange in order to be able to grip, together with the first radial flange, on tissue, such as annulus tissue, located between the first and second flange, and wherein, if the first flange and second flange are radially oriented, the pins extend from the first flange in the direction of the second flange.

207. Valve prosthesis according to clause 206, wherein the second flange is movable from an extended position, in which the second flange is axially oriented, to a radial position, in which the second flange is radially oriented.

The invention claimed is:
1. A stent, comprising:
   a tubular element with an open grid structure which is radially expandable from a compressed condition to an expanded condition, and which has a proximal and distal end; and
   a ring structure provided around the tubular element,
   wherein the tubular element and ring structure are interconnected,
   wherein the ring structure is a variable-diameter ring structure with distal and proximal flange feet,
   wherein the ring structure has an axial direction and a radial direction disposed transverse to the axial direction,
   wherein the ring structure is constructed from a series of elongated closed loops lying next to one another which, in each case, at the midpoint of the longitudinal sides of the loops, are attached laterally to one another via a junction to form the ring structure, in such a way that a) an imaginary center line through all junctions forms a closed ring and divides each loop into a distal flange foot of said distal flange feet and a proximal flange foot of said proximal flange feet, and b) the ring structure is expandable, wherein the distal and proximal flange feet each have a fixed end arranged at the imaginary center line and a free end pointing away from the imaginary center line, wherein the distal and proximal flange feet have a radial position, in which the free ends of the flange feet point in the radial direction, wherein the distal and proximal flange feet have an extended position, in which the distal and proximal flange feet extend in the axial direction, wherein the distal flange feet and the proximal flange feet lie in a longitudinal direction of the tubular element when the tubular element is in the compressed condition and the distal and proximal flange feet are in the extended position, wherein the distal and proximal flange feet, when in the extended position, are under a pre-tension, which, upon release, bends the distal and proximal flange feet from the extended position to the radial position, wherein, in the extended position, the free ends of the distal flange feet point in the distal direction whilst the free ends of the proximal flange feet point in the proximal direction such that, after the distal and proximal flange feet have bent from the extended position to the radial position, the distal and proximal flange feet interact to clamp surrounding tissue between the distal and proximal flange feet, and wherein the distal flange feet, at the fixed ends of the distal flange feet, have a concave-curved part including a hollow side facing toward the proximal flange feet, and in the hollow side of the concave-curved part, a filling is provided that is configured to increase a clamping force with which the distal and proximal flange feet clamp the tissue in situ when the distal and proximal flange feet are in the radial position.

2. The stent according to claim 1, wherein the separate distal flange feet have an unequal shape and/or length and/or width in relation to one another, and/or angle in relation to the longitudinal direction, and/or fillings.

3. The stent according to claim 1, wherein the tubular element has a first and second zone, wherein the diameter in the first zone is smaller than in the second zone, and wherein the proximal and/or distal flange feet may be provided in the first and/or second zone.

4. The stent according to claim 1, wherein the stent further comprises a heart valve provided in the tubular element.

5. The stent according to claim 1, wherein the fillings of the separate distal flange feet have, in relation to one another, an unequal shape and/or length and/or width and/or consistency and/or material properties.

6. The stent according to claim 1, wherein the fillings of the separate distal flange feet extend beyond the circumference of the respective flange feet and/or in a lateral and/or radial direction therefrom.

7. The stent according to claim 1, wherein the fillings of the separate distal flange feet are interconnected in such a way that a continuity arises between all or a number of fillings of the distal flange feet.

8. The stent according to claim 1, wherein the fixed ends of the distal flange feet are located at a distance from the distal end of the tubular element whilst the fixed ends of the proximal flange feet are located at a distance from the proximal end of the tubular element.

9. An assembly, comprising a stent according to claim 1 and an applicator,
wherein the applicator comprises:
a rod system having a first rod and a second rod which extends along the first rod;
a longitudinal centre line defined by the direction in which the first rod and the second rod extend; and
a manipulator,
wherein the manipulator comprises a first and second plurality of fingers, each with a first finger end and a second finger end,
wherein the second finger ends are free ends,
wherein the first finger ends of said pluralities of fingers are supported on the rod system in such a way that the fingers of said plurality of fingers, by moving rods of the rod system in relation to each other, are operable to be displaced from a first position to a second position,
wherein the distance from the free ends of the fingers to the longitudinal centre line is in the first position smaller than in the second position, and
wherein the free, second ends of the first plurality of fingers point towards the free second ends of the second plurality of fingers and the first ends of the first plurality of fingers face in a direction opposite to the first ends of the second plurality of fingers.

10. An assembly comprising a stent according to claim 1, further comprising:
a manipulator for releasing the stent,
wherein the distal and proximal flange feet, if they are in the extended position, are under a pre-tension, which, when released, bends the flange feet from the extended position to the radial position, and
wherein the manipulator comprises
a plurality of U-shaped obstacle elements with a first leg and a second leg, the free ends of which point in the distal direction,
an operating element, and
for each obstacle element, a cord, one end of which is attached to the obstacle element and the other end of which is connected to the operating element in such a way that, when the operating element is displaced in the proximal direction, the obstacle elements are retracted in the proximal direction.

11. A method for implanting a stent according to claim 1, the method comprising the following steps:
bringing the stent to its location in the body of the patient, whilst the tubular element is in the compressed condition and the distal and proximal flange feet are in the extended position;
allowing the tubular element to expand whilst maintaining the distal and proximal flange feet in the extended position; and
after the tubular element has been expanded, releasing the distal and proximal flange feet from the extended position to pivot into the radial position.

12. A method for removing or repositioning an expanded stent, comprising the following steps:
providing an assembly according to claim 9;
allowing the stent to expand by displacing the first and second plurality of fingers from the first to the second position;
following said expansion of the stent, compressing the stent by displacing the first and second plurality of fingers; and
subsequently removing the stent from the body of the patient or repositioning the stent in the body of the patient.

13. A stent, comprising:
a tubular element with an open grid structure which is radially expandable from a compressed condition to an expanded condition, and which has a proximal and distal end; and
a ring structure provided around the tubular element,
wherein the tubular element and ring structure are interconnected,
wherein the ring structure is a variable-diameter ring structure with distal and proximal flange feet,
wherein the ring structure has an axial direction and a radial direction disposed transverse to the axial direction,
wherein the ring structure is constructed from a series of elongated closed loops lying next to one another which, in each case, at the midpoint of the longitudinal sides of the loops, are attached laterally to one another via a junction to form the ring structure, in such a way that a) an imaginary center line through all junctions forms a closed ring and divides each loop into a distal flange foot of said distal flange feet and a proximal flange foot of said proximal flange feet, and b) the ring structure is expandable,
wherein the distal flange feet and the proximal flange feet each have a fixed end arranged at the imaginary center line and a free end pointing away from the imaginary center line,
wherein the distal and proximal flange feet have a radial position, in which the free ends of the flange feet point in the radial direction,
wherein the distal and proximal flange feet have an extended position, in which the distal and proximal flange feet extend in the axial direction,
wherein the distal flange feet and proximal flange feet lie in a longitudinal direction of the tubular element when the tubular element is in the compressed condition and the distal and proximal flange feet are in the extended position,
wherein the distal and proximal flange feet, when in the extended position, are under a pre-tension, which, upon release, bends the distal and proximal flange feet from the extended to the radial position,
wherein, in the extended position, the free ends of the distal flange feet point in the distal direction whilst the free ends of the proximal flange feet point in the proximal direction such that, after the distal and proximal flange feet have bent from the extended position to the radial position, the distal and proximal flange feet interact to clamp surrounding tissue between the distal and proximal flange feet, and
wherein the proximal flange feet, at the fixed ends of the proximal flange feet, have a concave-curved part including a hollow side facing toward the distal flange feet, and provided in the hollow side of the concave-curved part is a filling which is configured to increase the clamping force with which the distal and proximal flange feet clamp the tissue in situ when the distal and proximal flange feet are in the radial position.

14. The stent according to claim 13, wherein the tubular element and the ring structure are formed of a single piece of material.

15. The stent according to claim 13, wherein the tubular element and the ring structure are separate components, which are subsequently interconnected.

16. The stent according to claim 15, wherein the tubular element and the ring structure are interconnected by welds.

17. The stent according to claim 15, wherein the tubular element and the ring structure are interconnected by sutures.

18. The stent according to claim 15, wherein one or more of said junctions are provided with one or more radial bores.

19. The stent according to claim 13, wherein the ring structure is formed of a memory material.

20. The stent according to claim 19, wherein the memory material is a memory metal.

21. The stent according to claim 13,
wherein the ring structure is expandable from a first condition to a second condition, and
wherein the ring structure, when in the first condition, is under a radial pre-tension, which, upon release, causes the ring structure to expand in the direction of the second condition.

22. The stent according to claim 13, wherein the distal flange feet, when in the radial position, show a bulge facing towards the proximal flange feet.

23. The stent according to claim 22, wherein the bulges are provided in halves of the distal flange feet adjacent to the junction.

24. The stent according to claim 13, wherein the proximal flange feet, when in the radial position, show a bulge facing towards the distal flange feet.

25. The stent according to claim 24, wherein the bulges are provided in halves of the proximal flange feet adjacent to the junction.

26. The stent according to claim 13, wherein the distal flange feet, at the fixed ends of the distal flange feet, have a concave-curved part including a hollow side facing toward the proximal flange feet, and provided in the hollow side of the concave-curved part is a filling which is configured to increase the clamping force with which the distal and proximal flange feet clamp the tissue in situ when the distal and proximal flange feet are in the radial position.

27. The stent according to claim 13, wherein the ring structure is formed of a memory material.

28. The stent according to claim 13, wherein the stent further comprises a heart valve provided in the tubular element.

29. The stent according to claim 13, wherein the fillings of the separate proximal flange feet have, in relation to one another, an unequal shape and/or length and/or width and/or consistency and/or material properties.

30. The stent according to claim 13, wherein the fillings of the separate proximal flange feet extend beyond the circumference of the respective flange feet and/or in a lateral and/or radial direction therefrom.

31. The stent according to claim 13, wherein the fillings of the separate proximal flange feet are interconnected in such a way that a continuity arises between all or a number of fillings of the proximal flange feet.

32. The stent according to claim 13, wherein the fixed ends of the distal flange feet are located at a distance from the distal end of the tubular element whilst the fixed ends of the proximal flange feet are located at a distance from the proximal end of the tubular element.

33. The stent according to claim 13, wherein the fillings of the proximal flange feet are made from a material other than the material from which the tubular element, the distal flange feet and the proximal flange feet are made.

34. The stent according to claim 13, wherein, viewed in the radial direction and radial position, the concave-curved part of the proximal flange feet, on a side of the concave curved part facing towards the free ends of the proximal flange feet, changes to a straight part.

35. The stent according to claim 13, wherein the separate proximal flange feet have an unequal shape and/or length and/or width in relation to one another, and/or angle in relation to the longitudinal direction, and/or fillings.

36. A method for implanting a stent according to claim 13, the method comprising the following steps:
- bringing the stent to its location in the body of the patient, whilst the tubular element is in the compressed condition and the distal and proximal flange feet are in the extended position;
- allowing the tubular element to expand whilst maintaining the distal and proximal flange feet in the extended position; and
- after the tubular element has been expanded, releasing the distal and proximal flange feet from the extended position to pivot into the radial position.

\* \* \* \* \*